US006933276B1

(12) United States Patent
Hohn et al.

(10) Patent No.: US 6,933,276 B1
(45) Date of Patent: Aug. 23, 2005

(54) METHODS OF TREATING PERIPHERAL NEUROPATHIES USING NEUROTROPHIN-3

(75) Inventors: Andreas Hohn, Munich (DE); Yves-Alain Barde, Munich (DE); Hans Thoenen, Munich (DE); Ronald M. Lindsay, Briarcliff Manor, NY (US); George Yancopoulos, New York, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 08/342,457

(22) Filed: Nov. 18, 1994

Related U.S. Application Data

(63) Continuation of application No. 08/132,167, filed on Oct. 5, 1993, now abandoned, which is a continuation of application No. 07/570,189, filed on Aug. 20, 1990, now abandoned, which is a continuation-in-part of application No. 07/490,004, filed on Mar. 7, 1990, now abandoned, which is a continuation-in-part of application No. 07/400,591, filed on Aug. 30, 1989, now Pat. No. 5,180,820.

(51) Int. Cl.$^7$ .............................................. A61K 38/18
(52) U.S. Cl. ........................ 514/12; 514/866; 514/903; 514/2
(58) Field of Search ............................ 514/2, 12, 866; 514/903; 530/350, 399

(56) References Cited

U.S. PATENT DOCUMENTS

| 4,414,150 A | 11/1983 | Goeddel ............. 260/112.5 R |
| 4,699,875 A | 10/1987 | Appel ........................... 435/4 |
| 5,169,764 A | 12/1992 | Shooter et al. |
| 5,180,820 A | 1/1993 | Barde et al. |

FOREIGN PATENT DOCUMENTS

| EP | 0 121 338 | 10/1984 |
| EP | 0 386 752 | 12/1990 |
| JP | 1-58983 | 3/1989 |
| JP | 1-127710 | 5/1989 |
| JP | 1-193654 | 7/1989 |
| JP | 1-263613 | 10/1989 |

OTHER PUBLICATIONS

Chaudry et al., Muscle Nerve, 23(2):189–92, 2000.*
Apfel, Clinical Chemistry and Laboratory Medicine, 39(4):351–355, 2001.*
Apfel, American Journal of Medicine, 107(2B):34S–42S.*
Barinaga, M., Science, 264:772–774, 1994.*
Kanje et al. Brain Research 486:396–398 (1989).*
Ullrich et al., "Human β–nerve growth factor gene sequence highly homologous to that of mouse," 1983, Nature 303:821–5.
Scott et al., "Isolation and nucleotide sequence of a cDNA encoding the precursor of mouse nerve growth factor." 1983, Nature 302:538–40.

Liebrock et al., "Molecular cloning and expression of brain derived neurotrophic factor.", 1989, Nature 341:149–52.

Lindsay and Peters, "Spinal cord contains neurotrophic activity for spinal nerve sensory neurons. Late developmental appearance of a survival factor distinct from nerve growth factor.", 1984, Neurosci. 12:45–51.

Lindsay and Rohrer, "Placodal sensory neurons in culture. Nodose ganglion neurons are unresponsive to NGF, lack NGF receptors, but are supported by a liver–derived neurotrophic factor.", 1985, Develop. Biol. 112:30–48.

Edwards et al., "Processing of the native nerve growth factor precursor to form biologicaly active nerve growth factor.", 1988, J. Biol. Chem. 263:6810–6815.

Edwards et al., "Processing and secretion of nerve growth factor: Expression in mammalian cells with a vaccinia virus vector.", 1988, Mol. Cell. Biol. 8:2456–64.

Selby et al., "Cobra nerve growth factor: Structure and evolutionary comparison.", 1987, J. Neurosci. Res. 18:293–8.

Davies et al., "Different factors from the central nervous systems and periphery regulate the survival of sensory neurons.", 1986, Nature, 319:497–499.

Aruffo & Seed, "Molecular cloning of a CD28 cDNA by a high–efficiency COS cell expression system.", 1987, Proc. Natl. Acad. Sci. USA, 84:8573–8577.

Radeke et al., "Gene transfer and molecular cloning of the rat nerve growth factor receptor.", 1987, Nature, 325:593–597.

Altman, "Autoradiographic and Histological Studies of Postnatal Neurogenesis," 1966, J. Comp. Neur., 128:431–474.

(Continued)

Primary Examiner—Marianne P. Allen
(74) Attorney, Agent, or Firm—Valeta Gregg, Esq.

(57) ABSTRACT

The present invention relates to neurotrophin-3 (NT-3), a newly discovered member of the BDNF gene family. It is based, in part, on the identification of regions of nucleic acid sequence homology shared by BDNF and NGF (U.S. patent application Ser. No. 07/400,591, filed Aug. 30, 1989, incorporated by reference herein). According to the present invention, these regions of homology may be used to identify new members of the BDNF/NGF gene family; such methodology was used to identify NT-3. The present invention provides for the genes and gene products of new BDNF/NGF related neurotrophic factors identified by these methods. According to the invention, NT-3 may be used in the diagnosis and/or treatment of neurologic disorders, including, but not limited to, Alzheimer's disease and Parkinson's disease. Because NT-3 has been observed to exhibit a spectrum of activity different from the spcificities of BDNF or NGF, NT-3 provides new and valuable options for enducing regrowth and repair in the central nervous system.

11 Claims, 35 Drawing Sheets

OTHER PUBLICATIONS

Figure 4A:
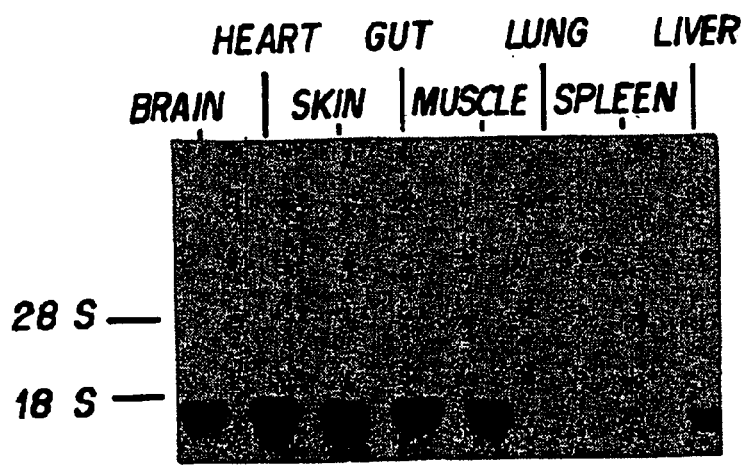

Schlesinger et al. "An Autoradiographic Study of the Time of Origin and the Pattern of Granule Cell Migration in the Dantate Gyrus of the Rat.", 1975, *J. Comp. Neur., 159*:149–176.

Large et al., "Nerve Growth Factor Gene Expression in the Developing Rat Brain.", 1986, *Science 234*:352–355.

Koh and Loy, "Localization and Development of Nerve Growth Factor–Sensitive Rat Basal Forebrain Neurons and Their Afferent Projections to Hippocampus and Neocortex.", 1989, *J. Neurosci. 9*:2999–3018.

Ernfors et al. "Expression of Nerve Growth Factor Receptor mRNA is Developmentally Regulated and Increased after Axotomy in Rat Spinal Cord Motoneurons.", 1989, *Neuron 2*:1605–1613.

Clegg et al., "Regulation of Nerve Growth Factor mRNA Levels in Developing Rat Heart Ventricle is Not Altered by Sympathectomy.", 1989, *Dev. Biol. 134*30–37.

Darling et al., "The Biosynthesis and Processing of Proteins in the Mouse 7S Nerve Growth Factor Complex.", 1983, *Cold Spring Harbor Symp. Quant. Biol. 1*:427–34.

Kaisho et al., "Cloning and expression of a cDNA encoding a novel human neurotrophic factor.", Jun. 1990, *FEBS Letters 266*(1,2):187–191.

Rosenthal et al. "Primary structure and biological activity of a novel human neurotrophic factor.", May 1990, *Neuron 4*:767–773.

Hu, G.L. et al., "Expression of the DNA for mouse β–nerve growth factor protein in *Escherichia coli*." 1988, *Gene 70*:57–65.

Appel, S.H. et al., "Neuropeptides and Alzheimer's disease: potential role of neurotrophic factors.", 1985, *Chemical Abstracts 102*:401, abstract No. 43871b.

Appel, S.H. et al., "New approaches to Alzheimer's disease: Neurotrophic factors.", 1985, *Chemical Abstracts 102*:418, abstract No. 147008s.

Uchida, Y. et al., "Neurotrophic factors in Alzheimer's disease brain.", 1989, *Chemical Abstracts 111*:203, abstract No. 229882X. Abstract of a review article: *Shinkei Seishiu Yakuri*, 1989 11(8), 633–9 (not in possession of Applicants). See also, enclosed *Medline* printout showing abstracts discussing this author's hypothesis.

Hallböök et al., "Production and characterization of Biologically Active Recombinant Beta Nerve Growth Factor.", Jan. 1988, *Molecular and Cellular Biology, 8*(1):452–456.

Erlich, H. et al., "Specific DNA Amplification.", Feb. 1988, *Nature 331*:461–462.

Pauli, U. et al., "Porcine tumor necrosis factor alpha: cloning with the polymerase chain reaction and determination of the nucleotide sequence.", Sep. 1989, *Gene 81*: 185–191.

Finn Hallböök, Carlos F. Ibáñez and Häkan Persson, 1991, "Evolutionary Studies of the Nerve Growth Factor Family Reveal a Novel Member Abuntdantly Expressed in Xenopus Ovary" Neuron 6:845–858.

Nancy Y. Ip, Carlos F. Ibáñez, Steven H. Nye, Joyce McClain, Pamela F. Jones, David R. Gies, Leonardo Belluscio, Michelle M. Le Beau, Rafael Espinosa III, Stephen P. Squinto, Häkan Persson and George D. Yancopoulos "Mammalian neurotrophin–4: Structure, chromosomal localization, tissue distribution, and receptor specificity." Proc. Natl. Acad. Sci. USA 89:3060–3064.

Lucy R. Berkemeier, John W. Winslow, David R. Kaplan, Karoly Nikolics, David V. Goeddel and Arnon Rosenthal "Neurotrophin–5: A Novel Neurotrophic Factor That Activates trk and trkB" Nov., 1991, Neuron 7(5):857–866.

Geoffrey M. Wahl, Shelby L. Berger, and Alan R. Kimmel, 1987, "Molecular Hybridization of Immobilized Nucleic Acids: Theoretical Concepts and Practical Considerations" Chapter 43, Methods in Enzymology, vol. 152, *Guide to Molecular Cloning Techniques*, Ed. Shelby L. Berger and Lan R. Kimmel.

R. Bruce Wallace and C. Garrett Miyada, 1987, "Oligonucleotide Probes for the Screening of Recombinant DNA Libraries" Chapter 43, Methods in Enzymology, vol. 152, *Guide to Molecular Cloning Techniques*, Ed. Shelby L. Berger and Lan R. Kimmel.

Maisonpierre et al., "Human and Rat Brain–Derived Neurotrophin Factor and Neurotrophin–3: Gene Structures, Distributions, and Chromosomal Localizations", Genomics 10:558–568 (1991).

Hohn et al., Nature 344:339–341 (1990).

Maisonpierre et al., Science 247:1446–1451 (1990).

Klein et al., trkB, a Novel Tyrosine Protein Kinase Receptor Expressed During Mouse Neural Development, EMBO J. 8(12):3701–3709 (1989).

Klein et al., "The trkB Tyrosine Protein Kinase is a Receptor for Brain–Derived Neurotrophic Factor and Neurotrophin–3", Cell 66:395–403 (1991).

Olsen et al., "Intraputiminal Infusion of Nerve Growth Factor to Support Adrenal Medullary Autografts in Parkinson's Disease", Arch. Neurol. 48:373–381 (1991).

Stromberg et al., "Rescue of Basal Forebrain Cholinergic Neurons After Implantation of Genetically Modified Cells Producing Recombinant NGF", J. Neurosci. Res. 25:405–411 (1990).

Ernfors et al., "Molecular Cloning and Neurotrophic Activities of a Protein with Structural Similarities to Nerve Growth Factor: Developmental and Topographical Expression in the Brain", PNAS USA 87:5454–5458 (1990).

Lamballe et al., "trkC, a New Member of the trk Family of Tyrosine Protein Kinases, Is a Receptor for Neurotrophin–3", Cell 66:967–979 (1991).

Middlemas et al., "trkB, a Neural Receptor Protein–Tyrosine Kinase: Evidence for a Full–Length and Two Truncated Receptors",Mol. Cel. Biol. 11:143–153 (1991).

Cordon–Cardo et al., "The trk Tyrosine Protein Kinase Mediates the Mitogenic Properties of Nerve Growth Factor and Neurotrophin–3", Cell 66:173–183 (1991).

Soppet et al., "The Neurotrophic Factors Brain–Derived Neurotrophic Factor and Neurotrophin–3 Are Ligands for the trkB Tyrosine Kinase Receptor", Cell 65:895–903 (1991).

Squinto et al., "trkB Encodes a Functional Receptor for Brian–Derived Neurotrophic Factor and Neurotrophin–3 but Not Nerve Growth Factor", Cell 65:885–893 (1991).

Knusel et al., "Promotion of Central Cholinergic and Dopaminergic Neuron Differentiation by Brain–Derived Neurotrophic Factor But Not Neurotrophin 3", PNAS USA 88:961–965 (1991).

Maisonpierre et al., "NT–3, BDNF, and NGF in the Developing Rat Nervous System: Parallel as well as Reciprocal Patterns of Expression", Neuron 5:501–509 (1990).

* cited by examiner

```
HSDPARRGELSVCDSISEWVIAADKKTAVDMSGGTVTVLEKVPVSKGQLKQYFYETKCNP    pig BDNF
SSSHPIFHRGEFSVCDSVSVWV**GDKTTATDIKGKEVMVLGEVNINNSVFKQYFFETKCRD  human NGF
SSSHPVFHRGEFSVCDSISVWV**GDKTTATDIKGKEVMVLGEVNINNSVFKQYFFETKCRD  bovine NGF
SSTHPYFHMGEFSVCDSVSVWV**ADKTTATDIKGKEVTVLAEVNVNNNVFKQYFFETKCRD  g. pig NGF
SSTHPVFHMGEFSVCDSVSVWV**GDKTTATDIKGKEVTVLAEVNINNSVFRQYFFETKCRA  mouse NGF
TAHPVLHRGEFSVCDSVSMWV**GDKTTATDIKGKEVTVLGEVNINNNVFKQYFFETKCRD   chick NGF
EDHPVHNLGEHSVCDSVSAWV***TKTTATDIKGNTVTVMENVNLDNKVYKQYFFETKCKN   snake NGF MGYTKEGCRGIDKRHWNSQCRTTQSYVRALTMDSKKRIGWRFIRIDTSCVCILTIKRGR     pig BDNF
PNPVDSGCRGIDSKHWNSYCTTTHTFVKALTMDGKQ*AAWRFIRIDTACVCVLSRKAVRRA   human NGF
PNPVDSGCRGIDAKHWNSYCTTTHTFVKALTMDGKQ*AAWRFIRIDTACVCVLSRKTGQRA   bovine NGF
PSPVESGCRGIDSKHWNSYCTTTHTFVKALTTDNKQ*AAWRFIRIDTACVCVLNRKAARRG   g. pig NGF
SNPVESGCRGIDSKHWNSYCTTTHTFVKALTTDEKQ*AAWRFIRIDTACVCVLSRKATRRG   mouse NGF
PRPVSSGCPGIDAKHWNSYCTTTHTFVKALTMGGKQ*AAWRFIRIDTACVCVLSRKSGRP    chick NGF
PNPEPSGCRGIDSSHWNSYCTETDTFIKALTMEGNQ*ASWRFIRIETACVCVITKKKGN     snake NGF
```

FIG. 1

```
                              GGAAACCCCG CCCGCTATAA ATAACAGGGA GGAGTTTACC      40
TCATTTGTTA GACTGGTGGT ACCCTCTCCT CACTCTCAGA TTGTCAGCCT CGGTGGCTGA TGCCAGAATG     110
ACAGGGGCTC TTCCGGCCAG CTGTTAACAC CTGTGTTTCC TTTTTTCAGA TCTTACAGGT GAACAAGGTG    180

1                                        10                                        20
Met Ser Ile Leu Phe Tyr Val Ile Phe Leu Ala Tyr Leu Arg Gly Ile Gln Gly Asn Ser
ATG TCC ATC TTG TTT TAT GTG ATA TTT CTT GCT TAT CTC CGT GGC ATC CAA GGC AAC AGC  240
                                  30                                        40

Met Asp Gln Arg Ser Leu Pro Glu Asp Ile Leu Ser Leu Asn Ser Lys Leu Ile Ile Gln
ATG GAT CAA AGG AGT TTG CCG GAA GAC ATA TCC AAT AGC CTC ATC AAG CTG ATC CAG      300
                                  50                                        60

Ala Asp Ile Leu Lys Asn Lys Leu Ser Lys Gln Met Val Asp Val Lys Glu Asn Tyr Gln
GCG GAT ATC TTG AAA AAC AAG CTT TCC AAA CAG ATG GTG GAT GTT AAG GAA AAT TAC CAG  360
                                  70                                        80

Ser Thr Leu Pro Lys Ala Glu Ala Pro Arg Glu Pro Glu Gln Gly Glu Ala Thr Arg Ser
AGC ACC CTG CCC AAA GCA GAG GCA CCC AGG GAA CCA GAG CAG GGA GAG GCC ACC AGG TCA  420
                                  90                                       100

Glu Phe Gln Pro Met Ile Ala Thr Asp Glu Leu Leu Arg Gln Arg Arg Tyr Asn
GAG TTC CAG CCA ATG ATT GCA ACG GAC GAG CTA CTA CGG CAA CAG AGA CGC TAC AAT      480
                                 110                                       120

Ser Pro Arg Val Leu Leu Ser Asp Ser Thr Pro Leu Glu Pro Pro Leu Tyr Leu Met
TCG CCC CGG GTC CTG CTG AGT GAC AGC ACC CCT TTG GAG CCC CCT TTA TAC CTA ATG      540
                                 130                                       140

Glu Asp Tyr Val Gly Asn Pro Val Val Ala Asn Arg Thr Ser Pro Arg Arg Lys Arg Tyr
GAG GAT TAT GTG GGC AAC CCG GTA GCC AAT AGA ACC TCA CCA CGG AGG AAA CGC TAT      600
```

FIG.2

```
                                            150                                     160
Ala Glu His Lys Ser His Arg Gly Glu Tyr Ser Val Cys Asp Ser Glu Ser Leu Trp Val
GCA GAA CAT AAG AGT CAC CGA GGA GAG TAC TCA GTG TGT GAC AGT GAG AGC CTG TGG GTG     660
                                                170                                     180
Thr Asp Lys Ser Ser Ala Ile Asp Ile Arg Gly His Gln Val Thr Leu Gly Glu Ile
ACC GAC AAG TCC TCA GCC ATT GAC ATT CGG GGA CAC CAG GTC ACA GTG CTG GGG GAG ATC     720
                                                190                                     200
Lys Thr Gly Asn Ser Pro Val Lys Gln Tyr Phe Tyr Glu Thr Arg Cys Lys Glu Ala Arg
AAA ACC GGT AAC TCT CCT GTG AAA CAA TAT TTT TAT GAA ACG AGA TGT AAA GAA GCC AGG     780
                                                210                                     220
Pro Val Lys Asn Gly Cys Arg Gly Ile Asp His Trp Asn Ser Gln Cys Lys Thr
CCG GTC AAA AAC GGT TGC AGG GGG ATT GAT AAA CAC TGG AAC TCT CAG TGC AAA ACT         840
                                                230                                     240
Ser Gln Thr Tyr Val Arg Ala Leu Thr Ser Glu Asn Asn Lys Leu Val Gly Trp Arg Trp
TCG CAA ACC TAT GTC CGA GCA CTG ACT TCA GAA AAC AAC AAA CTC GTA GGC TGG CGC TGG     900

Ile Arg Ile Asp Thr Ser Cys Val Cys Ala Leu Ser Arg Lys Ile Gly Arg Thr End
ATA CGA ATA GAC ACT TCC TGT GTG TGT GCC TTG TCG AGA AAA ATT GGA AGA ACA TGA ATT     960

GGCATCTGTC CCCACATATA AATTATTACT TTAAATTATA TGATATGCAT GTAGCATATA AATGTTTATA        1030
TTGTTTTAT ATATTATAAG TTGACCTTTA TTTATTAAAC TTCAGCAACC CTTACAGTAT ATAAGCTTTT         1100
TTCTCAATAA AATTCGTGTG CTTGCCTCCC CTCAGGCCTT TCCCATCTGT TAACCTTGTT TTGTGATTGG        1170
GCTCTCGGGA ACCCTTCTGT AAAACCTGTG TACACCAGTA TTTGGCATTC AGTATTGTCA AGGCCATGAC        1240
TGTGGTTTCA GTAAACTTTC TTAAAATCGG ATGAGTCAGA GTTG                                    1284
```

FIG. 2 (cont.)

```
                                    ↓
    V1
YAEHKSHRGEYSVCDSESLWVT**DKSSAIDIRGHQVTVLGEIKTGNSPVKQYFYETRC    NT-3
SSTHPVFHMGEFSVCDSVSVWV**GDKTTATDIKGKEVTVLAEVNINNSVFRQYFFETKC  NGG
HSDPARRGELSVCDSISEWVTAADKKTAVDMSGGTVTVLEKVPVSKGQLKQYFYETKC    BDNF
                              V2
                                         ↓    ↓
    V3                                V4
KEARPVKNGCRGIDDKHWNSQCKTSQTYVRALTSENNKLVGWRWIRIDTSCVCALSRKIGRT  NT-3
RASNPVESGCRGIDSKHWNSYCTTTHTFVKALTTDEKQ*AAWRFIRIDTACVCVLSRKATRRG NGF
NPMGYTKEGCRGIDKRHWNSQCRTTQSYVRALTMDSKKRIGWRFIRIDTSCVCTLTIKRGR  BDNF
                     ↑
```

FIG. 3

```
                                                                                           INTRON
            *** Pro Arg Leu Phe Gln Ser Asp Ile Asn Thr Cys Val Ser Phe Gln
  1  AGGTGGCTGA TTCCATAA AGA CCC AGA CTC TTC CAG TCA GAT ATT AAC ACT TGT GTT TCC TTT CAG
                                   -139
                                  →START(B)                      130
      Ile Leu Gln Val Asn Lys Val Met Ser Ile Phe Leu Tyr Val Ile Phe Leu Ala Tyr Leu Arg
      ATC TTA CAG GTG AAC AAG GTG ATG TCC ATC TTC TTG TAT GTG ATA TTT CTT GCT TAT CTC CGT
                          -120                                                      -110
      Gly Ile Gln Gly Asn Met Asp Gln Arg Ser Leu Pro Glu Asp Ser Leu Asn Ser Leu Ile Ile
 133  GGC ATC CAA GGC AAC ATG GAT CAA AGG AGT TTG CCA GAA GAC TCT CTC AAT TCC CTC ATT ATC
             -100                                           -90
      Lys Leu Ile Gln Ala Asp Ile Leu Lys Asn Lys Ala Glu Ala Pro Lys Ser Lys Gln Met Val Asp Val Lys Glu
      AAG CTC ATC CAG GCG CAT ATC TTG AAA AAC AAG GCA GAG GCA CCC AAA TCC AAG CAG ATG GTA GAT GTT AAG GAA
                    -80                                                          -70
      Asn Tyr Gln Ser Thr Leu Pro Met Ile Ala Thr Asp Thr Glu Leu Leu Arg Gln Leu Arg Glu Pro Arg Gly Glu Ala Thr Arg
 262  AAT TAC CAG AGC ACC CTG CTG ATG ATT GCA ACA GAC ACA GAA CTA CTA CGG CAA CAG AGA CCA GAG CAG GGA GCC ACC AGG
                                                                                         7 CLEAVE    -40
      Ser Glu Phe Gln Pro Met Ile Ala Thr Asp Thr Pro Leu Glu Pro Pro Leu Arg Gln Gln Arg Arg Tyr Asn
      TCA GAA TTC CAG CCG ATG ATT GCA ACA GAC ACA CCT TTG GAG CCC CCT TTA CGG CAA CAG AGA CGC TAC AAT
                                            -50                                                           -20
      Ser Pro Arg Val Leu Leu Ser Asp Ser Thr Pro Lys Thr Asp Ser Asp                 Leu Tyr Leu Met Glu Asp
 391  TCA CCC CGG GTC CTG CTG AGT GAT AGT ACC CCT AAA ACC GAC AGT GAC                 CTA TAT CTA ATG GAA GAT
                                        -10  GLYCOS.                  CLEAVE  -1  →MATURE
      Tyr Val Gly Asn Pro Val Val Thr Asn Arg Thr Ser Pro Arg Arg Lys Arg Arg Tyr Ala Glu His
      TAT GTG GGC AAC CCG GTC GTA ACC AAT AGA ACA TCA CCA CGG AGG AAA CGC TAT GCA GAG CAT
```

FIG. 7a

```
                    10                          20
     Lys Ser His Arg Gly Glu Tyr Ser Val CYS Asp Ser Glu Ser Leu Trp Val Thr Asp Lys Ser Ser
526  AAG AGT CAC CGA GGA GAG TAC TCA GTG TGT GAC AGT GAG AGC CTG TGG GTG ACC GAC AAG TCC TCA
                           30                             40
     Ala Ile Asp Ile Arg Gly His Gln Val Thr Val Leu Gly Ile Lys Thr Gly Asn Ser Pro
     GCC ATT GAC ATT CGG GGA CAC CAG GTT ACA GTG TTG GGA ATC AAA ACC GGC AAC TCT CCT
                    50                             60
     Val Lys Gln Tyr Phe Tyr Glu Thr Arg CYS Lys Glu Ala Arg Pro Val Lys Asn Gly CYS Arg Gly
649  GTG AAA CAA TAT TTT TAT GAA ACG AGG TGT AAA GAA GCC AGG CCA GTC AAA AAC GGT TCC AGG GGG
            70                           80                            90
     Ile Asp Asp Lys His Trp Asn Ser Gln CYS Lys Thr Ser Gln Thr Tyr Val Arg Ala Leu Thr
     ATT GAT GAC AAA CAC TGG AAC TCT CAG TGC AAA ACG TCG CAA ACC TAC GTC CGA GCA CTG ACT
                                        100                              110
     Ser Glu Asn Asn Lys Leu Val Gly Trp Arg Trp Ile Arg Ile Asp Thr Ser CYS Val CYS Ala Leu
778  TCA GAA AAC AAC AAA CTC GTA GGC TGG CGC ATA CGA ATA GAC ACT TCC TGT GTG TGT GCC TTG
     Ser Arg Lys Ile Gly Arg Thr ***
     TCA AGA AAA ATC GGA AGA ACA TGA ATT GGCATCTGTC CCCACATATA AATTATTACT TTAAATTATA
911  TGATATGCAT GTAGCATATA AATGTTTATA TTGTTTTTAT ATATTATAAG TTGACCTTTA TTTATTAAAC TTCAGCAACC
     CTTACAGTAT ATAAGCTTTT TTTTCTCAAT AAAATTCGTG TGCTTGCCTT CGCTCAGGCC TCTCCCATCT
1061 GTTAACCTTG TTTTGTGATT GGGCTCTCGG GAACCTTCTG TAAAACCTGT GTACACCAGT ATTGGCATT CAGTATTGTC
     AA
```

FIG. 7a (cont.)

FIG.7c

PRECURSOR HOMOLOGY REGION I

```
RAT NT3  (-144) QVNKV  MSILFYIFLAYLRGIQG NHMDQRSLPEDSLNSLI (-103)
RAT BDNF (-135) **RR*  *T***LTMVIS*FGCMKA AP*KEANVHGQGNLAYP (-96)
RAT HGF  (-126) **HS*  M*:LIT*F*I*V*: E:YTDS::**GDSVPEA (-87)
                                          ↑
                              START (B)  SIGAL CLEAVAGE
```

PRECURSOR HOMOLOGY REGION II

```
(-54) IATDTELLRQQRRYNSPRVLLSDSTPLEPP-PLYLMEDYVGNPVVTNRTSPRRKR  YAEHKS  (+6)
(-52) VRPNE*NHKDADL*T*-MSQV*****-L*F*L*EYKNYLDAA*MSM-*VR*   HSDPAR  (+6)
(-52) *TV*PK*F:-K***LR******F*T:P*PTSSDT*D*DFQAHGTISF-***M-*S** S:T*PV  (+6)
                                                                    →MATURE
      ↑                                                GLYC CLEAVAGE
   ? CLEAVAGE
```

FIG.7d

```
         →MATURE                                              60
RAT NT-3  YAEHKSHRGEYSVCDSESLW VT--DKSSAIDIRGHQVTVLGE IKTGNSPVKQYFYETRCKEA
RAT BDNF  HSDPAR*L****I*E* AAK**V*MS*GT****EK *PVSKGQL********K*NPM
RAT HGF   SSTHPVF*MF****V*V* *G--TT*K*KE***** VNINVF**F:*RAP
              20                      40

119                       (119)
                      80                     100                    (120)
RAT NT-3  RPVKNGCRGIDDKHWNSQCK TSQTYVRALTSENNKLVGWR WIRIDTSCVCALSRKIGRT
RAT BDNF  GYT*E*******KR******R *T*S******MDSK*RI*** F********T*TI*R**  →AA-RG
RAT HGF   NES**S****Y*T *:H*F*K***T:-D*QAA :*AV***AA-RG
                                                                  CLEAVAGE
```

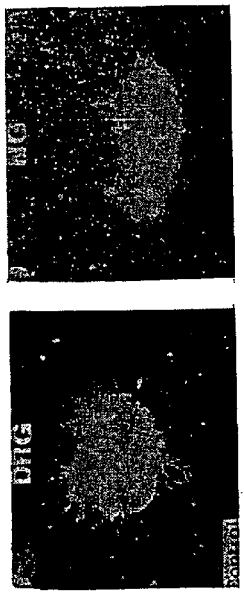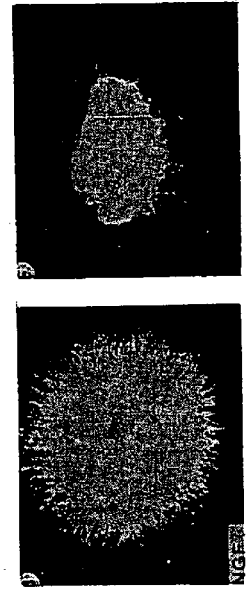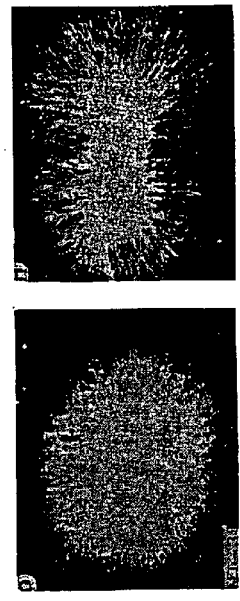
FIG. 8E  FIG. 8F  FIG. 8G  FIG. 8H
FIG. 8A  FIG. 8B  FIG. 8C  FIG. 8D

```
Sequence Range:   9 to 1142 | r/NT-3gene | R
Sequence Range:  33 to 1057 | h/NT-3gene | H 10              20              30              40              50                              R
         *               *               *               *               *
GA TTCCATAA TGA CCC AGA CTC TTC CAG TCA GAT ATT AAC ACT TGT GTT
CT AAGGTATT ACT GGG TCT GAG AAG GTC AGT CTA TAA TTG TGA ACA CAA
            End Pro Arg Leu Phe Gln Ser Asp Ile Asn Thr Cys Val>

40              50              60              70              80                              H
         *               *               *               *               *
TGCCAGAA TAA CAC AGA CTC AGC TGC CAG AGC CTG CTC TTA ACA CCT GTG
ACGGTCTT ATT GTG TCT GAG TCG ACG GTC TCG GAC GAG AAT TGT GGA CAC
         End His Arg Leu Ser Cys Gln Ser Leu Leu Leu Thr Pro Val>

60              70              80              90             100                              R
         *               *               *               *               *
TCC TTC TTT CAG ATC TTA CAG GTG AAC AAG GTG ATG TCC ATC TTG TTT
AGG AAG AAA GTC TAG AAT GTC CAC TTG TTC CAC TAC AGG TAG AAC AAA
Ser Phe Phe Gln Ile Leu Gln Val Asn Lys Val Met Ser Ile Leu Phe>
                                              PREPRO   >>

90             100             110             120             130                              H
         *               *               *               *               *
TTT CCT TTT CAG ATC TTA CAG GTG AAC AAG GTG ATG TCC ATC TTG TTT
AAA GGA AAA GTC TAG AAT GTC CAC TTG TTC CAC TAC AGG TAG AAC AAA
Phe Pro Phe Gln Ile Leu Gln Val Asn Lys Val Met Ser Ile Leu Phe>
                                              PREPRO   >>
```

FIG. 11

```
         110        120        130        140        150
          *          *          *          *          *
TAT GTG ATA TTT CTT GCT TAT CTC CGT GGC ATC CAA GGC AAC AAC ATG
ATA CAC TAT AAA GAA CGA ATA GAG GCA CCG TAG GTT CCG TTG TTG TAC

Tyr Val Ile Phe Leu Ala Tyr Leu Arg Gly Ile Gln Gly Asn Asn Met>

R
         140        150        160        170
          *          *          *          *
TAT GTG ATA TTT CTC GCT TAT CTC CGT GGC ATC CAA GGT AAC AAC ATG
ATA CAC TAT AAA GAG CGA ATA GAG GCA CCG TAG GTT CCA TTG TTG TAC

Tyr Val Ile Phe Leu Ala Tyr Leu Arg Gly Ile Gln Gly Asn Asn Met>

H
         160        170        180        190        200
          *          *          *          *          *
GAT CAA AGG AGT TTG CCA GAA GAC TCT CTC AAT TCC CTC ATT ATC AAG
CTA GTT TCC TCA AAC GGT CTT CTG AGA GAG TTA AGG GAG TAA TAG TTC

Asp Gln Arg Ser Leu Pro Glu Asp Ser Leu Asn Ser Leu Ile Ile Lys>

R
         180        190        200        210        220
          *          *          *          *          *
GAT CAA AGG AGT TTG CCA GAA GAC TCG CTC AAT TCC CTC ATT ATT AAG
CTA GTT TCC TCA AAC GGT CTT CTG AGC GAG TTA AGG GAG TAA TAA TTC

Asp Gln Arg Ser Leu Pro Glu Asp Ser Leu Asn Ser Leu Ile Ile Lys>

H
```

FIG.11 (cont.)

```
                                    R                H                R                H 210         220         230         240
            *           *           *           *
TTG ATC CAG GCG GAT ATC TTG AAA AAC AAG CTC TCC AAG CAG ATG GTA
AAC TAG GTC CGC CTA TAG AAC TTT TTG TTC GAG AGG TTC GTC TAC CAT
Leu Ile Gln Ala Asp Ile Leu Lys Asn Lys Leu Ser Lys Gln Met Val>

230         240         250         260         270
            *           *           *           *           *
CTG ATC CAG GCA GAT ATT TTG AAA AAC AAG CTC TCC AAG CAG ATG GTG
GAC TAG GTC CGT CTA TAA AAC TTT TTG TTC GAG AGG TTC GTC TAC CAC
Leu Ile Gln Ala Asp Ile Leu Lys Asn Lys Leu Ser Lys Gln Met Val>

250         260         270         280         290
   *           *           *           *           *
GAT GTT AAG GAA AAT TAC CAG AGC ACC CTG CCC AAA GCA GAG GCA CCC
CTA CAA TTC CTT TTA ATG GTC TCG TGG GAC GGG TTT CGT CTC CGT GGG
Asp Val Lys Glu Asn Tyr Gln Ser Thr Leu Pro Lys Ala Glu Ala Pro>

280         290         300         310         320
   *           *           *           *           *
GAC GTT AAG GAA AAT TAC CAG AGC ACC CTG CCC AAA GCT GAG GCT CCC
CTG CAA TTC CTT TTA ATG GTC TCG TGG GAC GGG TTT CGA CTC CGA GGG
Asp Val Lys Glu Asn Tyr Gln Ser Thr Leu Pro Lys Ala Glu Ala Pro>
```

FIG. 11 (cont.)

```
                                                                                              R
     300         310         320         330         340
      *           *           *           *           *
     AGA GAA CCA GAG CAG GGA GAG GCC ACC AGG TCA GAA TTC CAG CCG ATG
     TCT CTT GGT CTC GTC CCT CTC CGG TGG TCC AGT CTT AAG GTC GGC TAC

Arg Glu Pro Glu Gln Gly Gly Ala Thr Arg Ser Gly Phe Gln Pro Met

H
     330         340         350         360         370
      *           *           *           *           *
     CGA GAG CCG GAG CAG GGA GGA GGG CCC CGC AAG TCA GCA TTC CAG CCA GTG
     GCT CTC GGC CTC GTC CCT CCC GGG GCG TTC AGT CGT AAG GTC GGT CAC

Arg Glu Pro Glu Gln Gly Gly Pro Arg Lys Ser Ala Phe Gln Pro Val>

R
     350         360         370         380         390
      *           *           *           *           *
     ATT GCA ACA GAC ACA GAA CTA CTA CGG CAA CAG AGA CGC TAC AAT TCA
     TAA CGT TGT CTG CTT GAT GAT GCC GTT GTC TCT GCG ATG TTA AGT

Ile Ala Thr Asp Thr Glu Leu Leu Arg Gln Gln Arg Arg Tyr Asn Ser>

H
     380         390         400         410
      *           *           *           *
     ATT GCA ATG GAC ACC GAA CTG CTG CGA CAA CAG AGA CGC TAC AAC TCA
     TAA CGT TAC CTG TGG CTT GAC GAC GCT GTT GTC TCT GCG ATG TTG AGT

Ile Ala Met Asp Thr Glu Leu Leu Arg Gln Gln Arg Arg Tyr Asn Ser>
```

FIG. 11 (cont.)

```
                400                 410                 420                 430                 440
                 *                   *                   *                   *                   *
          CCC CGG GTC CTG CTG AGT GAC AGC ACC CCT TTG GAG CCC CCT CCC TTA
          GGG GCC CAG GAC GAC TCA CTG TCG TGG AAC CTC GGG GGA GGG AAT                              R

Pro Arg Val Leu Leu Ser Asp Ser Thr Pro Leu Glu Pro Pro Pro Leu>

420                 430                 440                 450                 460
                 *                   *                   *                   *                   *
          CCG CGG GTC CTG CTG AGC GAC ACG ACC CCC TTG GAG CCC CCG CCC TTG
          GGC GCC CAG GAC GAC TCG CTG TGC TGG GGG AAC CTC GGG GGC GGG AAC                          H

Pro Arg Val Leu Leu Ser Asp Thr Thr Pro Leu Glu Pro Pro Pro Leu>

450                 460                 470                 480                 490                 500                 510
                 *                   *                   *                   *                   *                   *                   *
          TAT CTA ATG GAA GAT TAT GTG GGC AAC CCG GTG GTA CCG AAT AGA ACA
          ATA GAT TAC CTT CTA ATA CAC CCG TTG GGC CAC CAT TGG TTA TCT TGT                          R

Tyr Leu Met Glu Asp Tyr Val Gly Asn Pro Val Val Thr Asn Arg Thr>

470                 480                 490                 500                 510
                 *                   *                   *                   *                   *
          TAT CTC ATG GAG GAT TAC GTG GGC AGC CCC GTG GTG GCG AAC AGA ACA
          ATA GAG TAC CTC ATG CAC CAC CCG TCG GGG CAC CAC CGC TTG TCT TGT                          H

Tyr Leu Met Glu Asp Tyr Val Gly Ser Pro Val Val Ala Asn Arg Thr>
```

FIG. 11 (cont.)

FIG.11(cont.)

```
      490         500         510         520         530
       *           *           *           *           *
     TCA CCA CGG AGG AAA CGC TAT GCA GAG CAT AAG AGT CAC CGA GGA GAG
     AGT GGT GCC TCC TTT GCG ATA CGT CTC GTA TTC TCA GTG GCT CCT CTC                R

Ser Pro Arg Arg Lys Arg    Tyr Ala Glu His Lys Ser His Arg Gly Glu>
                                 MATURE__>>

520         530         540         550
           *           *           *           *
        CGG AAA CGG TAC GCG GAG CAT AAG AGT CAC CGA GGG GAG
     TCA --- --- GCC GCC TTT GCC ATG CGC CTC GTA TTC TCA GTG GCT CCC CTC           H
     AGT --- ---

Ser _____ Arg Arg Lys Arg    Tyr Ala Glu His Lys Ser His Arg Gly Glu>
                                     MATURE__>>

540         550         560         570         580
         *           *           *           *           *
     TAC TCA GTG TGT GAC AGT GAG AGC CTG TGG GTG ACC GAC AAG TCC TCA
     ATG AGT CAC ACA CTG TCA CTC TCG GAC ACC CAC TGG CTG TTC AGG AGT              R

Tyr Ser Val Cys Asp Ser Glu Ser Leu Trp Val Thr Asp Lys Ser Ser>

560         570         580         590         600
         *           *           *           *           *
     TAC TCG GTA TGT GAC AGT GAG AGT CTG TGG GTG ACC GAC AAG TCA TCG
     ATG AGC CAT ACA CTG TCA CTC TCA GAC ACC CAC TGG CTG TTC AGT AGC              H

Tyr Ser Val Cys Asp Ser Glu Ser Leu Trp Val Thr Asp Lys Ser Ser>
```

```
                                                                    R                    H                                           R                    H 590         600         610         620         630
           *           *           *           *           *
        GCC ATT GAC ATT CGG GGA CAC CAG GTT ACA GTG TTG GGA GAG ATC AAA
        CGG TAA CTG TAA GCC CCT GTG GTC CAA TGT CAC AAC CCT CTC TAG TTT

Ala Ile Asp Ile Arg Gly His Gln Val Thr Val Leu Gly Glu Ile Lys>

610         620         630         640         650
           *           *           *           *           *
        GCC ATC GAC ATT CGG GGA CAC CAG GTC ACG GTG CTG GGG GAG ATC AAA
        CGG TAG CTG TAA GCC CCT GTG GTC CAG TGC CAC GAC CCC CTC TAG TTT

Ala Ile Asp Ile Arg Gly His Gln Val Thr Val Leu Gly Glu Ile Lys>

640         650         660         670         680
                                   *           *           *           *           *
                                ACC GGC AAC TCT CCT GTG AAA CAA TAT TTT TAT GAA ACG AGG TGT AAG
                                TGG CCG TTG AGA GGA CAC TTT GTT ATA AAA ATA CTT TGC TCC ACA TTC

Thr Gly Asn Ser Pro Val Lys Gln Tyr Phe Tyr Glu Thr Arg Cys Lys>

660         670         680         690         700
                                   *           *           *           *           *
                                ACG GGC AAC TCT CCC GTC AAA CAA TAT TTT TAT GAA ACG CGA TGT AAG
                                TGC CCG TTG AGA GGG CAG TTT GTT ATA AAA ATA CTT TGC GCT ACA TTC

Thr Gly Asn Ser Pro Val Lys Gln Tyr Phe Tyr Glu Thr Arg Cys Lys>
                                                      50
```

FIG.11(cont.)

```
                                                         R
            690           700           710           720
             *             *             *             *
        GAA GCC AGG CCA GTC AAA AAC GGT TGC AGG GGG ATT GAT GAC AAA CAC
        CTT CGG TCC GGT CAG TTT TTG CCA ACG TCC CCC TAA CTA CTG TTT GTG

Glu Ala Arg Pro Val Lys Asn Gly Cys Arg Gly Ile Asp Asp Lys His>

H
            710           720           730           740           750
             *             *             *             *             *
        GAA GCC AGG CCG GTC AAA AAC GGT TGC AGG GGT ATT GAT GAT AAA CAC
        CTT CGG TCC GGC CAG TTT TTG CCA ACG TCC CCA TAA CTA CTA TTT GTG

Gly Ala Arg Pro Val Lys Asn Gly Cys Arg Gly Ile Asp Asp Lys His>

R
        730           740           750           760           770
         *             *             *             *             *
        TGG AAC TCT CAG TGC AAA ACG TCG CAA ACC TAC GTC CCA GCA CTG ACT
        ACC TTG AGA GTC ACG TTT TGC AGC GTT TGG ATG CAG CGT CGT GAC TGA

Trp Asn Ser Gln Cys Lys Thr Ser Gln Thr Tyr Val Arg Ala Leu Thr>

H
            760           770           780           790
             *             *             *             *
        TGG AAC TCT CAG TGC AAA ACA TCC CAA ACC TAC GTC CGA GCA CTG ACT
        ACC TTG AGA GTC ACG TTT TGT AGG GTT TGG ATG CAG GCT CGT CAC TGA

Trp Asn Ser Gln Cys Lys Thr Ser Gln Thr Tyr Val Arg Ala Leu Thr>
         75
```

FIG. 11 (cont.)

```
                                                            R                              H
     780            790           800           810           820
      *              *             *             *             *
    TCA GAA AAC AAC AAA CTC GTA GGC TGG CGC ATA CGA ATA GAC ACT
    AGT CTT TTG TTG TTT GAG CAT CCG ACC GCG TAT GCT TAT CTG TGA

Ser Glu Asn Asn Lys Leu Val Gly Trp Arg Ile Arg Ile Asp Thr>

800            810           820           830           840
      *              *             *             *             *
    TCA GAG AAC AAT AAA CTC GTG GGC TGG CGG ATA CGG ATA GAC ACG
    AGT CTC TTG TTA TTT GAG CAC CCG ACC GCC TAT GCC TAT CTG TGC

Ser Glu Asn Asn Lys Leu Val Gly Trp Arg Ile Arg Ile Asp Thr>
                                          100

830            840           850           860                       R                H
      *              *             *             *
    TCC TGT GTG TGT GCC TTG TCA AGA AAA ATC GGA AGA ACA TGA
    AGG ACA CAC ACA CGG AAC AGT TCT TTT TAG CCT TCT TGT ACT

Ser Cys Val Cys Ala Leu Ser Arg Lys Ile Gly Arg Thr End>

850            860           870           880
      *              *             *             *
    TCC TGT GTG TCT GCC TTG TCG AGA AAA ATC GGA AGA ACA TGA
    AGG ACA CAC AGA CGG AAC AGC TCT TTT TAG CCT TCT TGT ACT

Ser Cys Val Cys Ala Leu Ser Arg Lys Ile Gly Arg Thr End>
                                                    119
```

FIG. 11 (cont.)

```
       870        880        890        900        910        920
        *          *          *          *          *          *
   ATTGGCATCT GTCCCCACAT ATAAATTATT ACTTAAAAT ATATGATATG CAT      R
   TAACCGTAGA CAGGGGTGTA TATTTAATAA TGAAATTTAA TATACTATAC GTA 890        900        910        920        930        940
        *          *          *          *          *          *
   ATTGGCATCT CTCCCCATAT ATAAATTATT ACTTAAAAT ATATGATATG CAT      H
   TAACCGTAGA GAGGGGTATA TATTTAATAA TGAAATTTAA TATACTATAC GTA 930        940        950        960        970        980
        *          *          *          *          *          *
   GTAGCATATA AATGTTTATA TTGTTTTAT ATATTATAAG TTGACCTTTA TTTATTAAAC   R
   CATCGTATAT TTACAAATAT AACAAAAATA TATAATATTC AACTGGAAAT AAATAATTTG 950        960        970        980        990        1000
        *          *          *          *          *          *
   GTAGCATATA AATGTTTATA TTGTTTTAT ATAT-ATAAG TTGACCTTTA TTTATTAAAC   H
   CATCGTATAT TTACAAATAT AACAAAAATA TATA-TATTC AACTGGAAAT AAATAATTTG
```

FIG. 11 (cont.)

```
                                                              990        1000       1010       1020       1030       1040
                                                               *          *          *          *          *          *
                                                        TTCAGCAACC CTTACAGTAT ATAAGCTTTT TTTCTCAAT  AAAATTCGTG TGCTTGCCTT    R
                                                        AAGTCGTTGG GAATGTCATA TATTCGAAAA AAAGAGTTA  TTTTAAGCAC ACGAACGGAA 1010       1020       1030       1040       1050
                                                               *          *          *          *          *
                                                        TTCAGCAACC CT-ACAGTAT ATAAGCTTAT CGATACCGTC GACCTCGAGG GGGGGCC/      H
                                                        AAGTCGTTGG GA-TGTCATA TATTCGAATA GCTATGGCAG CTGGAGCTCC CCCCCGG/

1050       1060       1070       1080       1090       1100
                                                               *          *          *          *          *          *
                                                        CGCTCAGGCC TCTCCCATCT GTTAACCTTG TTTTGTGATT GGGCTCTCGG GAACCTTCTG    R
                                                        GCGAGTCCGG AGAGGGTAGA CAATTGGAAC AAAACACTAA CCCGAGAGCC CTTGGAAGAC 1110       1120       1130       1140
                                                               *          *          *          *
                                                        TAAAACCTGT GTACACCAGT ATTTGGCATT CAGTATTGTC AA/                      R
                                                        ATTTTGGACA CATGTGGTCA TAAACCGTAA GTCATAACAG TT/
```

FIG. 11 (cont.)

FIG. 15A
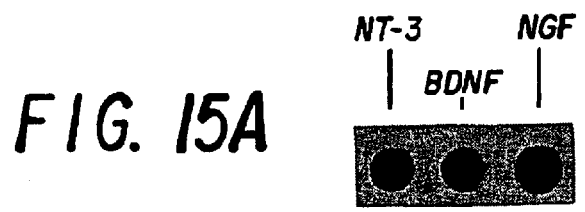
FIG. 15B
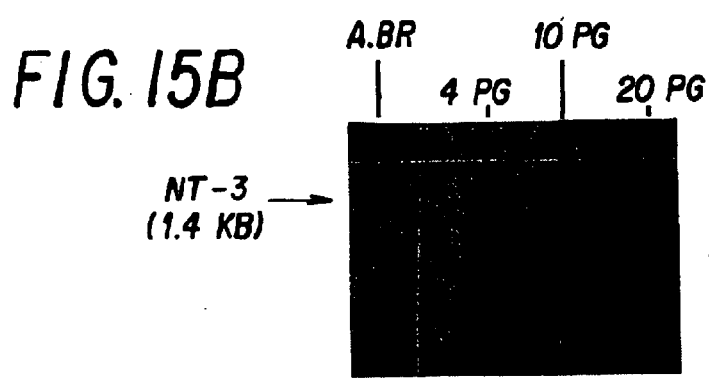
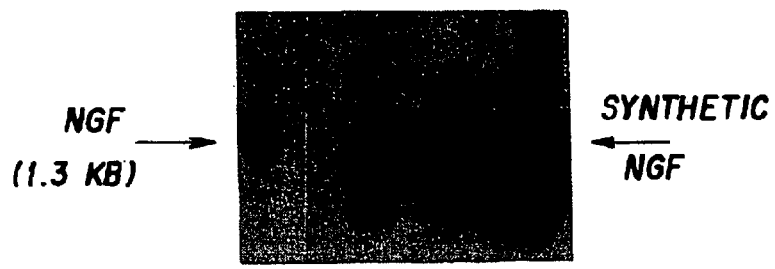

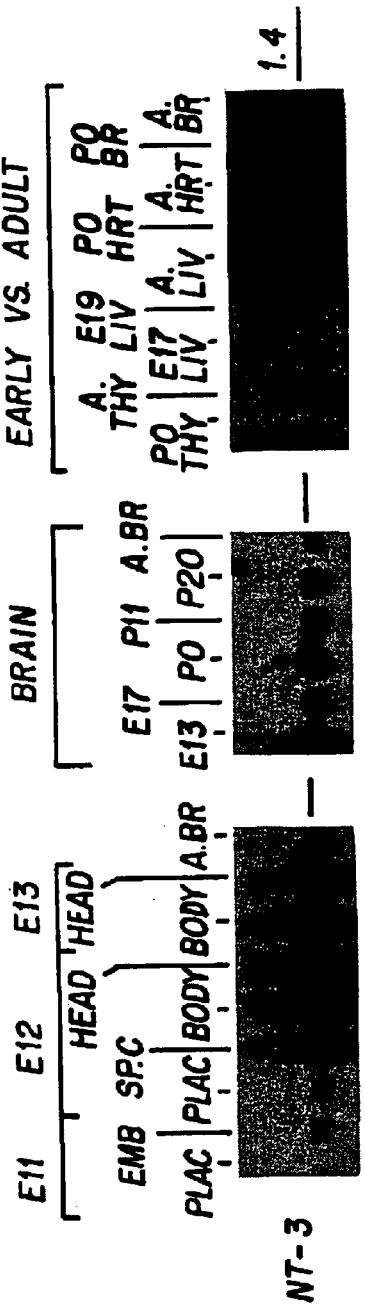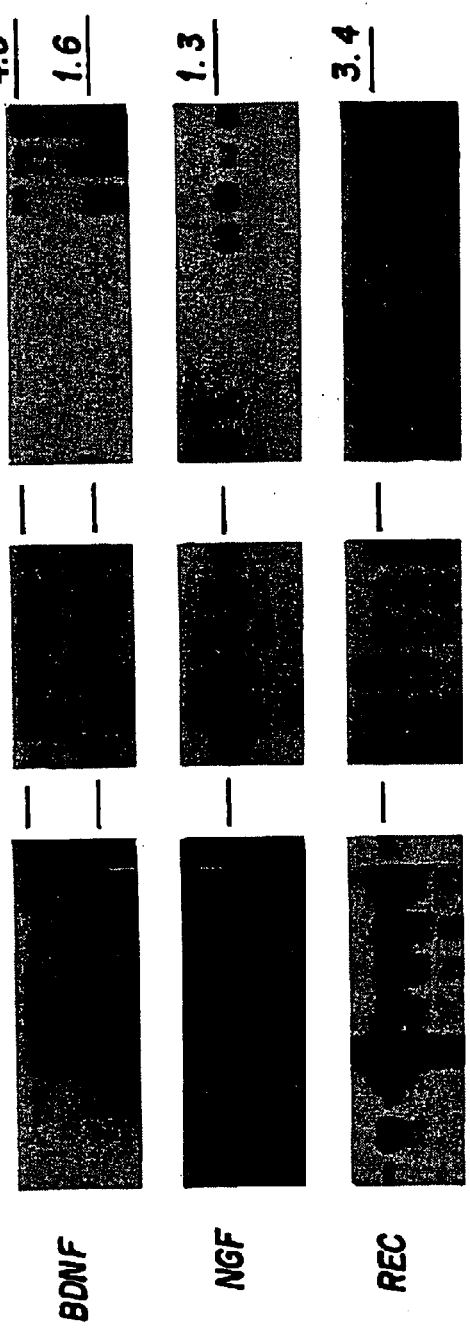

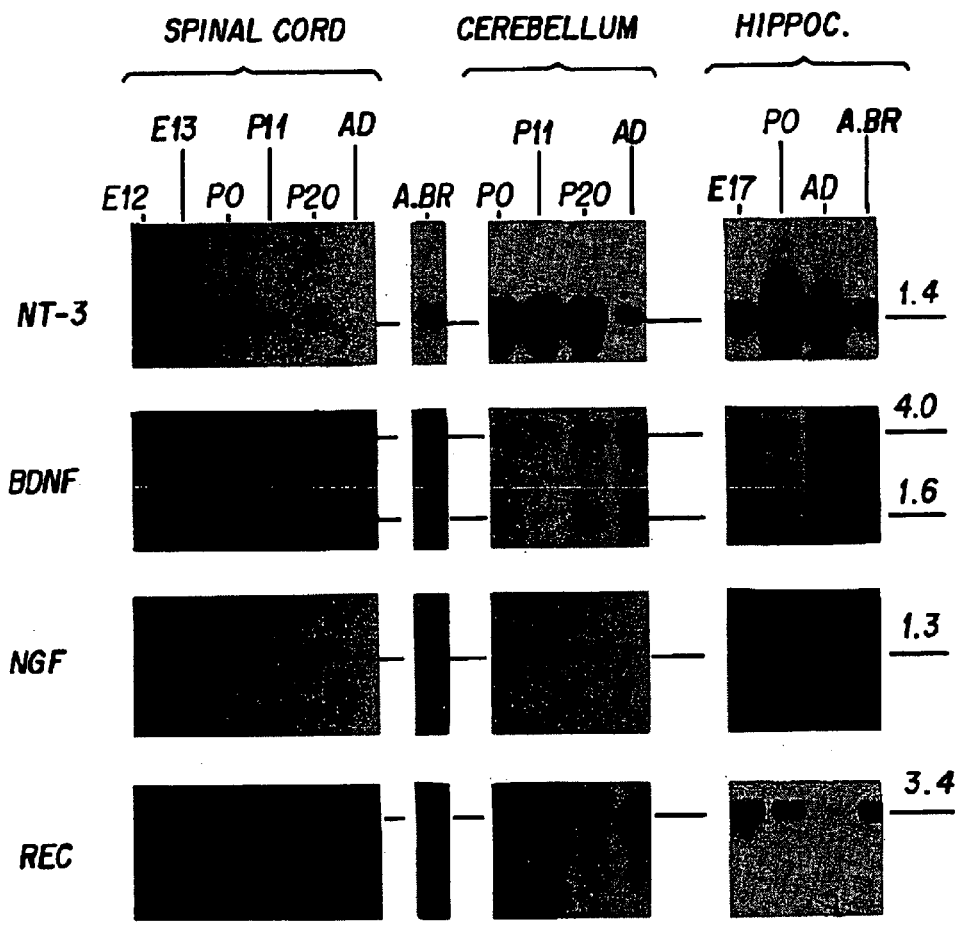
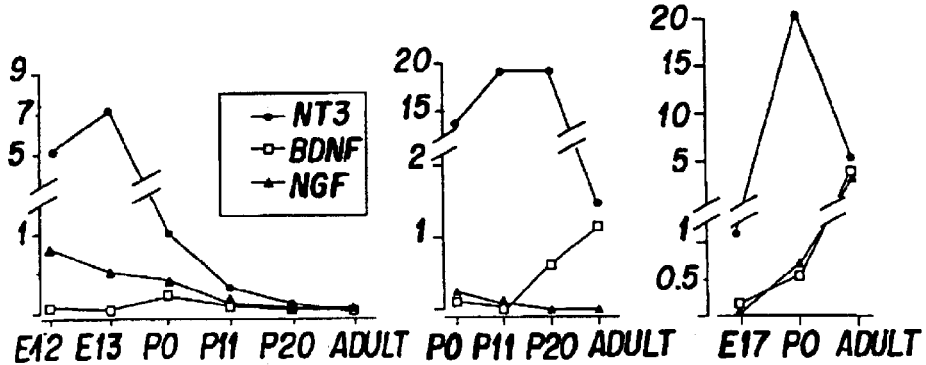

METHODS OF TREATING PERIPHERAL NEUROPATHIES USING NEUROTROPHIN-3

This is a continuation of application Ser. No. 08/132,167, filed Oct. 5, 1993, abandoned, which is a continuation of application Ser. No. 07/570,189, filed Aug. 20, 1990, abandoned, which is a continuation-in-part of application Ser. No. 07/490,004, filed Mar. 7, 1990, abandoned, which is a continuation-in-part of application Ser. No. 07/400,591, filed Aug. 30, 1989, which is incorporated by reference herein in its entirety and has issued as U.S. Pat. No. 5,180,820.

1. INTRODUCTION

The present invention relates to neurotrophin-3 (NT-3), a newly discovered neurotrophic factor which is a member of the BDNF/NGF gene family. The gene encoding NT-3 has been cloned and sequenced, and recombinant NT-3 has been expressed in mammalian cells. Recombinant NT-3 has been shown to have a spectrum of biological activity which differs from that of BDNF and NGF. The present invention provides for nucleic acid sequences encoding NT-3, to the substantially pure NT-3 protein, peptide fragments or derivatives produced in quantity therefrom, and to antibodies directed toward NT-3 protein or peptides. The NT-3 gene products of the invention may be used in the diagnosis and therapy of a variety of neurological disorders including in particular, peripheral neuropathies, Alzheimer's disease and Parkinson's disease.

2. BACKGROUND OF THE INVENTION

2.1. The Role of Neurotrophic Factors in the Nervous System

The development and maintenance of the nervous system depends on proteins known as neurotrophic factors. Widespread neuronal cell death accompanies normal development of the central and peripheral nervous systems, and apparently plays a crucial role in regulating the number of neurons which project to a given target field (Berg, D. K., 1982, Neuronal Development 297–331; Cowan et al., 1984, 225:1258–65). Ablation and transplantation studies of peripheral target tissues during development have shown that neuronal cell death results from the competition among neurons for limiting amounts of survival factors ("neurotrophic factors") produced in their projection fields. These observations led to the identification of nerve growth factor (NGF), which remains, by far, the best characterized neurotrophic molecule (Levi-Montalcini, and Angeletti, P. U., 1968, Physiol. Rev. 48:534–69; Thoenen, H. and Barde, Y. -A., 1980, Rev. 60:1284–335). Understanding the role and mechanism of action of NGF has been greatly aided by the serendipitous discovery of a rich source of this protein in male mouse submaxillary glands, which allowed for the purification and cloning (Ullrich et al., 1983, Nature 303:821–5; Scott et al., 1983, Nature 302:538–40) of NGF, as well as the generation of neutralizing antibodies. Because NGF only supports a limited set of neuronal populations, the existence of additional neurotrophic factors has long been postulated (Varon, S. and Adler, R. 1981, Adv. Cellular Neurobiol. 2:115–63; Barde et al., 1987, Prog Brain Res 71:185–9; Snider, W. D. and Johnson, E. M., 1989, Ann. Neurol. 26:489–506). While it is now clear that such factors do exist, their extremely low abundance has impeded their molecular characterization. Nevertheless, purification of small amounts of two such proteins, namely brain-derived neurotrophic factor (BDNF) and ciliary neurotrophic factor (CNTF), has recently permitted their partial nucleic acid sequencing (Leibrock et al., 1989, Nature 341:149–52; Stockli et al., 1989, Nature 342:21–28 and Lin et al., 1989, Science 246:1023–25). Despite specificities for distinct neuronal populations, BDNF and NGF (but not CNTF) display sufficient structural homology to be regarded as members of a gene family (Leibrock et al., 1989, Nature 341:149–52).

2.2. Other Neurotrophic Factors

In the past decade there have been numerous reports of neurotrophic activity in extracts of a great variety of tissues and in the conditioned culture medium of many different cell types. In almost all cases, however, progress in purifying and characterizing these activities has been hampered by the fact that such activities are present in extremely small amounts, in the range of picograms to nanograms per gram of tissue.

Furthermore, whereas adequate bioassays have been established for peripheral neurons, designing reliable, reproducible and specific assays for central nervous system neurons has proved problematic. While individual types of peripheral neurons are found as discrete, easily dissectable ganglia, central nervous system (CNS) neurons are invariably highly heterogenous in their distribution. Thus, specific markers are required for either identification or enrichment of particular classes of CNS neurons. Progress in producing such markers, for example, antibodies directed toward cell surface or cytoskeletal components, or specific histological stains, has been very limited. Accordingly, characterization of neurotrophic factors which are (i) not as abundant as NGF, (ii) difficult to assay, and (iii) not available in sufficient quantities to elicit antibody production, has proved to be an exceedingly difficult process.

2.2.1. Comparison of Brain Derived Growth Factor and Nerve Growth Factor

Neurotrophic activity capable of sustaining the survival of embryonic chick dorsal root ganglion neurons in vitro was identified in the "conditioned medium" in which rat C-6 glioma cells had been cultured (Barde et al., 1978, Nature 274:818). The activity was not neutralized by antibodies to mouse NGF, suggesting the presence of another neurotrophic factor in the conditioned medium. Similar activities that could not be blocked by NGF antibodies were subsequently reported in cultures of normal adult rat brain astroglial cells (Lindsay, 1979, Nature 282:80–82; Lindsay et al., 1982, Brain Res. 243:329–343) and in extracts of developing and adult rat brain (Barde et al., 1980, Proc. Natl. Acad. Sci. U.S.A. 77:1199–1203) and developing and mature chick spinal cord (Lindsay and Peters, 1984, Neurosci. 12:45–51). However, in no case was the active factor (s) isolated or identified, and it remains questionable as to whether the observed activities were due to the same or different factor(s).

Using pig brain as a starting material, Barde et al. (1982, EMBO J. 1:549–553) reported a factor, now termed brain-derived neurotrophic factor (BDNF), which appeared to promote the survival of dorsal root ganglion neurons from E10/E11 chick embryos. The neurotrophic activity was found to reside in a highly basic protein (isoelectric point, pI>10.1) which migrated during sodium dodecyl sulfate (SDS) gel electrophoresis as a single band of 12.3 kD molecular weight. The purification factor was estimated to be $1.4 \times 10^6$, but the yield was very low with only approximately 1 μg of BDNF purified from 1.5 kg of pig brain. Furthermore, because the last step in the purification process was preparative gel electrophoresis, the activity of BDNF could not be fully renatured secondary to the presence of residual SDS (Barde and Thoenen, 1985, in "Hormones and Cell Regulation," Vol. 9, Dumont et al., eds. Elsevier Science Publishers, pp. 385–390). It was noted that the highly basic nature and molecular size of BDNF were very similar to the NGF monomer. However, BDNF appeared to have properties that differed from the known properties of NGF in that (a) in the chick dorsal root ganglion bioassay, antibodies to NGF had no apparent effect on the biological activity of BDNF; (b) in the same assay, the effects of BDNF and NGF appeared to be additive; and (c) unlike NGF, BDNF was found to have no effect on the survival of E12 chick sympathetic neurons. In addition, during early studies with brain extracts, it was observed that the neurotrophic activity in these sources appeared to act upon sensory neurons at later stages of development than were associated with NGF. Using dissociated cultures of chick embryo neurons cultured on a polycationic substrate such as polylysine or polyornithine, BDNF was found to support the survival of more than 30 percent of E10–11 (embryonic day ten or eleven) dorsal root ganglion neurons but seemed to have little effect on the survival of the same neurons at E6 (Barde et al., 1980, Proc. Natl. Acad. U.S.A. 77:1199–1203 supra). Under similar conditions, NGF supported the survival of 30–40 percent of E6 DRG neurons. Interestingly, it was later found that when cultured on a substrate coated with the extracellular matrix glycoprotein laminin, both NGF and BDNF supported the survival of about 50 percent of DRG neurons from chick embryos of ages E6–E12 (Lindsay et al., 1985, Develop. Biol. 112:319–328). In the latter study, the effects of NGF and BDNF were found to be additive when both were present at saturating concentrations.

Early studies by Levi-Montalcini (1966, The Harvey Lectures 60:217–259) on the neuronal specificity of NGF suggested that NGF was not a ubiquitous neurotrophic factor even for sensory neurons, as NGF appeared to have no effect upon neurons of certain cranial sensory ganglia of the chick, especially the nodose ganglion of the tenth cranial nerve. Later in vivo studies (Johnson et al., 1980, Science 210:916–918; Pearson et al., 1983 Develop. Biol. 96:32–36) showed that NGF deprivation during embryogenesis had no effect on the survival of neurons in most cranial sensory ganglia of the rat, while similar treatment greatly depleted the neuronal count in sensory ganglia derived from the neural crest. More detailed in vitro studies (Lindsay and Rohrer, 1985, Develop. Biol. 112:30–48; Davies and Lindsay, 1985, Develop. Biol. 111:62–72; Lindsay et al., 1985, J. Cell. Sci. Suppl. 3:115–129) clearly indicated that NGF supports the survival of most neural crest-derived sensory neurons but has no apparent effect on the survival of cranial sensory neurons derived from neural placodes.

The first demonstration of a neuronal specificity of BDNF distinct from that of NGF was the demonstration in vitro that purified BDNF supports the survival of 40–50% of sensory neurons dissociated from the neural placode-derived nodose ganglion of the chick embryo at E6, E9 or E12 (Lindsay et al., 1985, J. Cell. Sci. Supp. 3:115–129). NGF was without apparent effect on these neurons either by itself or in conjunction with BDNF. It was later shown in explant culture studies that BDNF appeared to support survival and neurite outgrowth from other neural placode-derived sensory ganglia, including the petrosal, geniculate and ventrolateral trigeminal ganglia (Davies et al., 1986, J. Neurosci. 6:1897–1904), none of which have been found to be sensitive to NGF. In all of the above studies, neutralizing antibodies to NGF had no effect upon the observed activity of BDNF. In addition to its effects on cultured neurons from peripheral ganglia, BDNF was found to stimulate survival and neuronal differentiation of cells cultured from quail neural crest (Kalcheim and Gendreau, 1988, Develop. Brain Res. 41:79–86).

Prior to the instant invention, the inability to produce sufficient amounts of BDNF for immunization prevented the production of anti-BDNF antibodies for comparison to anti-NGF antibodies in their effects on neuronal populations, and precluded BDNF/NGF cross-neutralization experiments. Two recent studies with BDNF (Kalcheim et al., 1987, EMBO J. 6:2871–2873; Hofer and Barde, 1988, Nature 331:261–262) have, however, indicated a physiological role of BDNF in avian PNS development. If a mechanical barrier was placed in ovo between E3/E4 DRG (embryonic day 3 or 4 dorsal root ganglia) and their CNS target in the neural tube, many DRG neurons were observed to die (Kalcheim and Le Douarin, 1986, Develop. Biol. 116:451–466). It was postulated that this neuronal death may have been due to deprivation from a CNS (neural tube) derived neurotrophic factor. It was subsequently observed that BDNF attached to a laminin-coated sialastic membrane could prevent this cell death (Kalcheim et al., 1987, EMBO J. 6:2871–2873). Injections of BDNF into developing quail eggs has been found to reduce naturally occurring cell death in the nodose ganglia, an effect not seen with NGF (Hofer and Barde, 1988, Nature 331:261–262). In addition to its effect on peripheral sensory neurons of both neural crest and neural placode origin, BDNF was found to support the survival of developing CNS neurons. Johnson et al. (1986, J. Neurosci. 6:3031–3938) presented data indicating that BDNF supports the survival of retinal ganglion cells cultured from E17 rat embryos. This extended previous studies which showed that conditioned media and brain extracts prepared from the target regions of retinal ganglion cells appeared to support the survival of these neurons (McCaffery et al., 1982, Ex. Brain Res. 48:37–386; Sarthy et al., 1983, J. Neurosci. 3:2532–2544; Turner et al., 1983, Dev. Brain Res. 6:77–83).

In addition to its effects on the survival of developing neurons in culture, BDNF has been shown to have effects on cultured adult peripheral and central nervous system neurons. BDNF, as well as NGF, has been shown to stimulate axonal regeneration from adult rat DRG neurons in culture (Lindsay, 1988, J. Neurosci. 8:2394–2405) although adult sensory neurons did not appear to require neurotrophic factors for maintenance in vitro over 3 or 4 weeks. Furthermore, in cultures of adult rat retina, BDNF was observed to promote both survival and axonal elongation from retinal ganglion cells (Thanos et al., 1989, Eur. J. Neurosci. 1:19–26). A comparison of the biological effects of NGF and BDNF is presented in Table I.

TABLE I

COMPARISON OF BIOLOGICAL ACTIVITIES OF BDNF AND NGF*

| | | SURVIVAL** | |
|---|---|---|---|
| | | BDNF | NGF |
| PERIPHERAL NERVOUS SYSTEM | | | |
| (i) | E6 Chick DRG | – | ++ |
| | E10 Chick DRG | + | ++ |
| | E12 Chick Symp | – | ++ |
| | (Barde et al., 1980, supra) | | |

TABLE I-continued

COMPARISON OF BIOLOGICAL ACTIVITIES OF
BDNF AND NGF*

|  |  | SURVIVAL** | |
|---|---|---|---|
|  |  | BDNF | NGF |
| (ii) | E6 – E12 Chick DRG | ++ | ++ |
|  | E6 – E12 Chick Nodose | ++ | – |
|  | E12 – Chick Sympathetic | – | ++ |
|  | E12 – Chick ciliary | – | – |
|  | (Lindsay et al., 1985, supra) |  |  |
| (iii) | E3 – E14 Chick: |  |  |
|  | Jugular | +/++ | ++ |
|  | DM-trigeminal | +/++ | ++ |
|  | Petrosal | +/++ | – |
|  | Geniculate | +/++ | – |
|  | VL-trigeminal | ++ | – |
|  | Vestibular | – | – |
|  | Mesencephalic | ++ | – |
|  | (Davies et al., 1986, supra) |  |  |
|  | (Barde et al., 1987, Prog. |  |  |
|  | Brain Res., 71:185–189) |  |  |
|  | CENTRAL NERVOUS SYSTEM |  |  |
| (i) | E17 Rat Retinal Ganglion Cells | ++ | – |
|  | (Johnson et al., 1986, |  |  |
|  | J. Neurosci. 63031–3038) |  |  |

*in chronological order according to publication date; effects tested in vitro
**no survival: (–); moderate survival (+); good survival (++)

2.2.2. Neuronal Targets of Brain Derived Neurotrophic Factor

Sensory neurons of peripheral nerve ganglia have been found to arise from either of two distinct, transient embryological structures, namely, the neural crest and neural placodes. The neural crest appears to give rise to both neurons and satellite cells of autonomic ganglia and spinal nerve sensory ganglia, i.e. DRG. The contribution of the neural crest and neural placodes to the formation of cranial nerve sensory ganglia has been studied using the quail/chick chimera transplantation system devised by Le Douarin (Le Douarin, 1973, Develop. Biol. 20:217–222; Noden, 1978, Develop. Biol. 67:313–329; Narayanan and Narayanan, 1980, Anat. Rec. 196:71–82; Ayer-Le Lievre and Le Douarin, 1982, Develop. Biol. 94:291–310; D'Amico-Martel and Noden, 1983, Am. J. Anat. 166:445–468). As reviewed in Lindsay et al. (1985, J. Cell. Sci. Supp. 3:115–129), it is now believed, at least for birds, that neurons of the distal ganglia of the VIIth, IXth, and Xth cranial nerves (geniculate, petrosal and nodose ganglia, respectively) and neurons of the vestibuloacoustic complex of the VIIIth cranial nerve are exclusively of neural placode origin. The trigeminal ganglion of the Vth cranial nerve contains neurons of both crest and placode origin (with the placode-derived neurons predominant in the ventrolateral pole of the maxillo-mandibular lobe) whereas the satellite cells of all cranial ganglia have been found to be entirely of neural crest origin.

From in vitro experiments using both explant and dissociated, neuron-enriched cultures of spinal and cranial nerve sensory neurons, it has been found that sensory neurons of neural crest origin are responsive to NGF; in contrast, neurons derived from neural placodes (including neurons of the ventrolateral portion of the trigeminal ganglion and the entire neuronal population of the vestibular, geniculate, petrosal and nodose ganglia) have been observed to be largely unresponsive to NGF throughout embryonic development. In contrast to differences in their requirement and responsiveness to NGF, both placode and neural crest derived sensory neurons have been found (Table I) to be responsive to the survival and neurite-promoting activity of BDNF (Lindsay et al., 1985, J. Cell. Sci. Supp. 3:115–129; Lindsay et al., 1985, Develop. Biol. 112:319–328 Kalcheim and Gendreau, 1988, Develop. Brain Res. 41:79–86). Tebar and Barde (1988, J. Neurosci. 8:3337–3342) studied the binding parameters of radioactively labeled BDNF to chick embryo dorsal root ganglion neurons; their results are consistent with the existence of two classes of BDNF receptors, one with high affinity for BDNF, the other with low affinity. No high affinity receptors were observed on sympathetic neurons.

The known neuronal targets of BDNF were further reviewed by Barde et al. (1987, Prog. Brain Res. 71:185–189). Prior to the instant invention, identification of cells synthesizing BDNF has not been feasible due to the lack of nucleic acid or antibody probes specific for BDNF. Attempts to prepare either polyclonal or monoclonal antibodies to BDNF have been unsuccessful. This failure to raise antibodies had hindered the molecular cloning of BDNF, determination of the physiological effect of depriving developing neurons of BDNF in vivo, quantitation of BDNF in tissues using an immunoassay, and localization of BDNF using immunocytochemistry.

TABLE II

SUMMARY OF BDNF RESPONSIVE
AND NON-RESPONSIVE NEURONS*

A.  Responsive Neurons
    I.  Chick sensory neurons of neural crest origin in:
       (a) dorsal root ganglion
       (b) jugular ganglion
       (c) dorsomedial trigeminal ganglion
       (d) mesencephalic trigeminal nucleus**
    II. Chick sensory neurons of ectodermal placode origin in:
       (a) nodose ganglion
       (b) vestibular ganglion
       (c) petrosal ganglion
       (d) geniculate ganglion
       (e) ventrolateral trigeminal ganglion
    III. Rat retinal ganglion cells
    IV. Chick retinal ganglion cells***
B.  Non-Responsive Neurons
    I.  Chick and rat sympathetic neurons
    II. Chick parasympathetic ciliary neurons

*From Barde et al., 1987, Prog. Brain Res. 71:185–189
**See Davies et al., 1986, Nature 319:497–499
***Rodriguez - Tebar et al., 1989, Dev. Biol. 136:296–303

2.2.3. The Cloning of the Gene for Brain-Derived Neurotrophic Factor

The cloning of the BDNF gene was first performed as described in U.S. patent application Ser. No. 07/400,591, filed Aug. 30, 1989, which is incorporated by reference in its entirety herein. Briefly, minute quantities of BDNF protein were purified from pig brain, allowing the determination of fragments of amino acid sequence which could, in turn, be used to design corresponding oligonucleotides. These synthetic oligonucleotides were then used as primers in polymerase chain reaction (PCR) with cDNA template prepared from BDNF producing cells. The products of PCR were utilized as probes to permit cloning of complete cDNA and/or genomic BDNF genes from a variety of species, including human, pig, rat, and mouse and the sequences of these genes were determined. Expression of recombinant BDNF was achieved in COS cells.

3. SUMMARY OF THE INVENTION

The present invention relates to neurotrophin-3 (NT-3), a newly discovered member of the BDNF gene family. It is based, in part, on the identification of regions of nucleic acid sequence homology shared by BDNF and NGF (U.S. patent application Ser. No. 07/400,591, filed Aug. 30, 1989, incorporated by reference herein). According to the present invention, these regions of homology may be used to identify new members of the BDNF/NGF gene family; such methodology was used to identify NT-3. The present invention provides for the genes and gene products of new BDNF/NGF related neurotrophic factors identified by these methods.

The present invention relates, in part to recombinant DNA molecules which encode NT-3. In particular specific embodiments of the invention, the DNA encoding NT-3 is derived from human DNA, murine DNA, or rat DNA. The present invention also provides for recombinant DNA molecules comprising at least a portion of the nucleic acid sequences substantially as depicted in FIG. 2 (murine NT-3), FIG. 7 (rat NT-3), or FIG. 11 (human NT-3). The present invention also provides for recombinant DNA expression vectors which may be used to produce recombinant NT-3 protein and related peptides.

In alternate embodiments, the present invention provides for NT-3 proteins and related peptides, and for methods for producing and preparing such peptides and proteins. The present invention also relates to antibodies directed toward NT-3 proteins and peptides.

According to the invention, NT-3 may be used in the diagnosis and/or treatment of neurologic disorders, including, but not limited to, peripheral neuropathies such as diabetic neuropathies, toxic and nutritional neuropathies, hereditary neuropathies and AIDS related neuropathies and degenerative diseases such as Alzheimer's disease. It has been shown that NT-3 supports the survival of dopaminergic neurons: accordingly, in preferred embodiments of the invention, NT-3 may be used in the treatment of Parkinson's disease. Because NT-3 has been observed to exhibit a spectrum of activity different from the specificities of BDNF or NGF, NT-3 provides new and valuable options for enducing regrowth and repair in the central nervous system.

4. DESCRIPTION OF THE FIGURES

FIG. 1. Comparison of sequences of BDNF and NGF from various species. Sequence analysis of the gene encoding BDNF and deduction of its amino acid sequence revealed that this protein has many structural similarities to NGF. The primary sequence of mature BDNF, as well as the general structure and probable mode of processing from a precursor protein, suggest strongly that the NGF and BDNF genes may have evolved from a common ancestral gene. Within the region of the mature polypeptides, if only three gaps are introduced in the NGF sequences to optimize matching, a total of 51 amino acid identities are common to the previously known NGFs from many species and to porcine and human BDNF. These identities include all six cysteine residues, suggesting that the NGFs and BDNF share very similar secondary structure. Furthermore, four segments of six or more amino acids can be seen in which NGFs from all of the species listed above and from porcine BDNF are either identical, or differ by no more than about one conservative amino acid substitution. Thus, it is reasonable to conclude that NGF and BDNF are closely related members of a gene family.

FIG. 2. Genomic sequence and deduced amino acid sequence of murine NT-3. The amino acid sequence starts with the first ATG codon found after 3 in-frame stop codons. The underlined sequences indicate the location of the primers used in the first round of PCR. The only N-glycosylation consensus sequence is doubly underlined, and the arrow indicates the putative start of processed, mature NT-3.

FIG. 3. Amino acid sequence comparison between mature mouse NT-3, NGF (Scott et al, 1983, Nature 302:538–540) and BDNF (Leibrock et al., 1989, Nature 341:149–152). The mature mouse BDNF sequence shown here is 100% identical with that of pig BDNF. Bold letters and shadowing indicate amino acids found at identical positions in all 3 proteins and the arrows point to all cysteine residues. Asterisks indicate gaps introduced to optimize matching. V1–V4 indicates the 4 variable domains consisting of more than 3 contiguous amino acids.

FIG. 4. Tissue distribution of NT-3 mRNA in the mouse. Twenty µg of total RNA was applied to each lane and hybridized with a $^{32}$P-labelled double stranded DNA probe. (A) A single band corresponding to about 1.4 kilobases can be seen in all tissues, the weakest signal being observed in lung and the strongest in heart. Skeletal muscle was taken from the thighs. (B) In brain the strongest signal is obtained with the hippocampus and the cerebellum.

Figure 5:
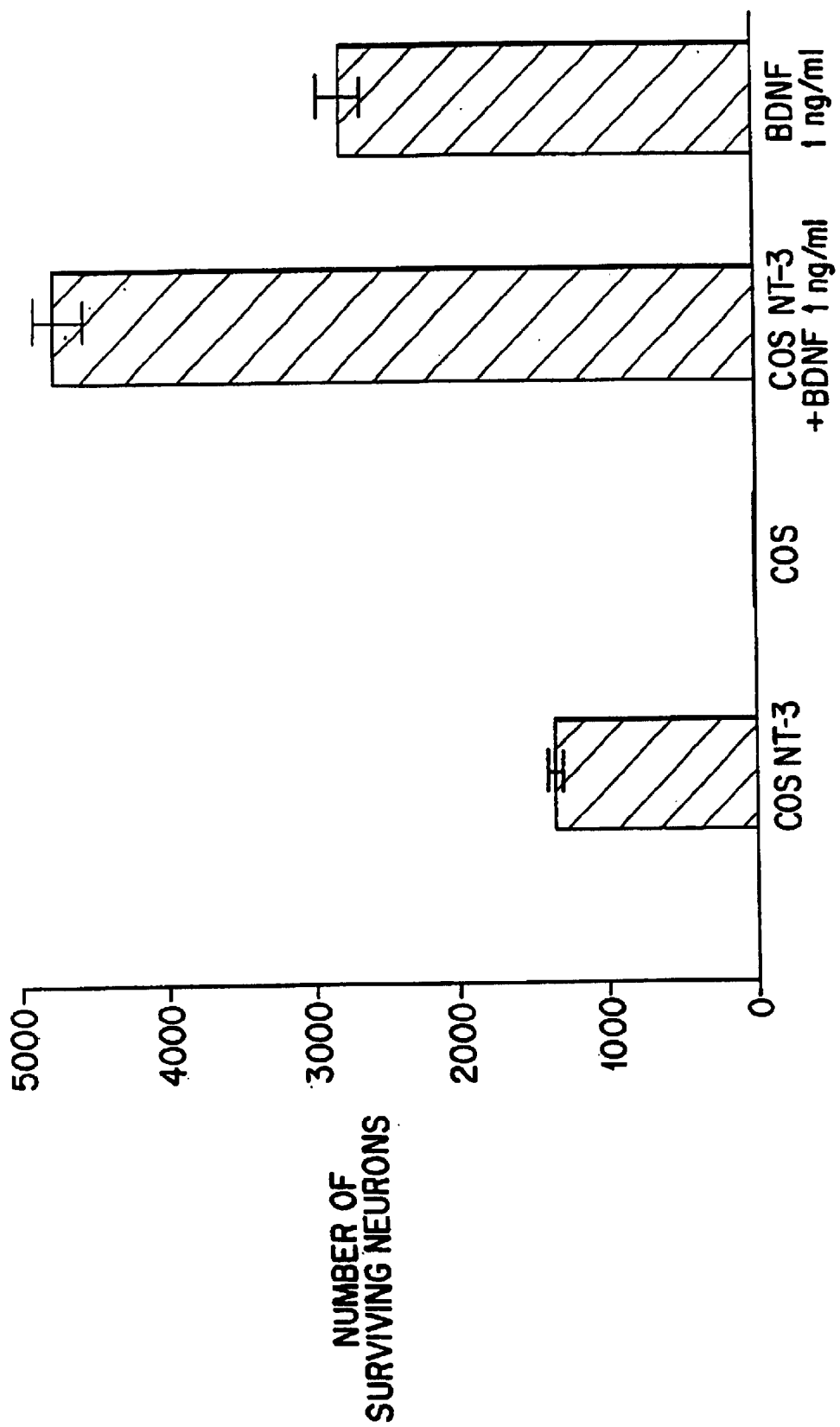

FIG. 5. Survival of sensory neurons isolated from nodose ganglia obtained from chick of 8-day of embryonic age. 5,000 cells were plated on a polyornithine-laminin substrate, and the surviving neurones counted after 24 hours. The concentration of BDNF used here is 3 times the minimal concentration required to obtain maximal survival. No neurons were found to survive without addition, or with conditioned medium used at a dilution 1:50 with non-transfected COS cells, or cells transfected with control DNA.

Figure 6A:
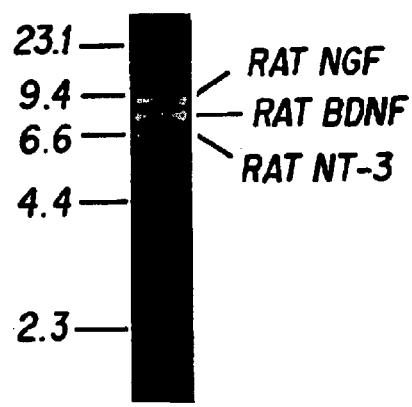

FIG. 6. (A) PCR product derived using degenerate 1B and 2C primers (designated R1B/2C) detects a novel gene, NT-3, as well as the NGF and BDNF genes in rat genomic DNA. (B) Restriction map of a rat NT-3 genomic clone. Two independent bateriophage clones specifically hybridizing to the R1B/2C probe were isolated from a rat genomic library. A schematic representation of the restriction map of one of these clones, containing a 19.5 kb insert, is depicted. The thickened line indicates the open reading frame (ORF) of NT-3 (see FIG. 7A). The position of the R1B/2C probe is indicated.

FIG. 7. Sequence of rat NT-3 and its homology to rat NGF and rat BDNF. (A) Nucleotide and amino acid sequence of NT-3. DNA sequence spanning ORF encoded by NT-3 gene, with amino acid translation indicated above DNA sequence; asterisks mark beginning and end of open reading frame. Amino acids are numbered with position +1 assigned to first residue of mature NT-3 (119 amino acids). The cleavage site that is used to release mature NT-3 is boxed, as is the conserved glycosylation site just upstream to this cleavage site; another potential cleavage site, which is similarly located to a proposed intermediate processing site in NGF (Darling et al., 1987, Cold Spring Harb Symp Quant Biol 1:427–34)(but which is not conserved in BDNF), is boxed and marked with a "?CLEAVE". The six cysteines in mature NT-3 are underlined. The methionine initiation codon for the short precursor form of NT-3 (at position −139), which marks start site "B" as discussed in the text, is also underlined. The proposed splice acceptor site/intron boundary upstream of the "B" start site is indicated in the figure. (B) Sequence alignments of rat NT-3 with rat NGF and rat BDNF. The MacVector sequence analysis software (purchased from International Biotechnologies, Inc.) was used to generate a matrix alignment of the rat NT-3 ORF with the ORFs of the NGF and BDNF genes (using a window size of and a minimum match of 20%). Significant matches seen along the diagonal of this matrix are represented underneath a schematic representation of the NT-3 protein product; two regions of homology upstream to the mature NT-3, which are seen in comparison to both NGF and BDNF, are designated I and II. As is seen in the figure, region I extends upstream of the "B" start site used to generate the short precursor form of NT-3, supporting the contention that a longer precursor exists. (C) Sequence comparisons between NT-3, NGF and BDNF in homology regions I and II. Sequences in these regions are aligned to maximize homology, with gaps inserted for alignment indicated by a "–". Identities of either BDNF or NGF with the NT-3 sequence are indicated by "*", while identities of NGF with BDNF are indicated by "." in the NGF sequence. A "+" on top of the sequence indicates residues which are completely conserved between rat NT-3 and the NGF and BDNF sequences from all species examined. The following sites defined for NGF, previously predicted for BDNF and proposed here for NT-3 are indicated: the "B" start site methionine initiation codon; the signal sequence cleavage site (Edwards et al., 1988, Mol Cell Biol 8:2456–64); a proposed NGF intermediate cleavage site which is absent in BDNF but is present in NT-3; a glycosylation acceptor site; the proteolytic cleavage site which releases the mature factors. (D) Sequence comparisons of the mature forms of NT-3, BDNF and NGF. Conserved cysteines are underscored with bold diamonds. "*", "." and "-" as in panel C. C-terminal cleavage site, only present in NGF sequence, is indicated.

FIG. 8. Comparison of NGF, BDNF and NT-3 activities as assayed on explanted embryonic (day 8) chick ganglia. Photomicrographs of dorsal root ganglia (DRG) (panels A–D), nodose ganglia (NG) (panels E–H), and sympathetic chain ganglia (SG) (panels I–L) cultured for 24 hours (DRG and NG) or 48 hours (SG) either in the absence of any neurotrophic factor (Control; A, E, I) or in the presence of COS cell supernatants containing NGF (B, F, J), or BDNF (C, G, K), or NT-3 (D, H, L). There is almost no neurite outgrowth in control cultures (500 μl of COS cell supernatant from mock transfected cells). NGF (10 μl of COS cell supernatant) produced profuse fiber outgrowth from DRG and SG but not NG. Increasing the NGF COS cell supernatant from 20 to 500 μl produced no effect on NG. BDNF (10 μl COS cell supernatant) produced fiber outgrowth from DRG and NG but not SG; higher amounts (20 to 500 μl) had no effect on SG. NT-3 (20 μl COS cell supernatant on DRG and NG, 200 μl on SG) produced fiber outgrowth from all three types of ganglia, although initiation of growth was slower and less profuse from SG. Ganglia were cultured as explants in collagen gel (Lindsay R. M. and Rohrer, H., 1985, Dev. Biol. 112:30–48) in F14 medium supplemented with 5% horse serum as described previously (Lindsay et al., 1985, Dev Biol 112:319–28). Scale bar=200 μm.

Figure 9A:
Figure 9B:
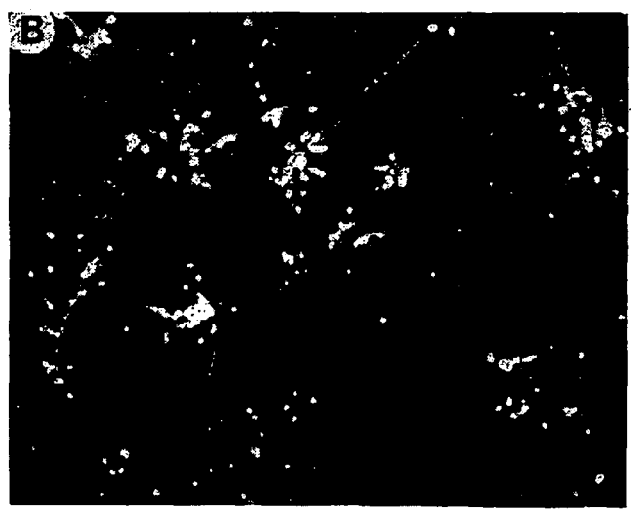
Figure 9C:
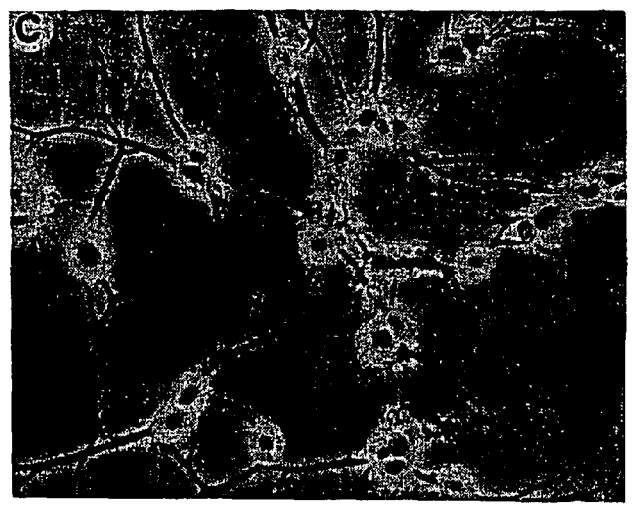

FIG. 9. NT-3 promotes survival and neurite outgrowth in highly enriched cultures of DRG neurons. Photomicrographs of neuron-enriched (>95% neurons) cultures of dissociated chick embryonic (day 8) DRG treated for 48 hours with either: (A) supernatant (500 μl) from mock transfected COS cells or (B, C) supernatant (500 μl) from NT-3 transfected cells. A and B are darkfield micrographs; in A (control culture) fewer than 5% of the neurons plated survived; in B the number of process-bearing neurons was approximately 60% of the neurons plated. From a dose-response curve this was found to be the maximal effect of NT-3 on chick E8 DRG neurons. (C) A higher magnification phase contrast micrograph of the same culture as shown in B. Note the large number of phase bright neuronal cell bodies and the virtual absence of any non-neuronal cells. Cultures were established as previously described (Lindsay et al., 1985, Dev Biol 112:319–28). Scale bar=150 μl (C).

Figure 10:
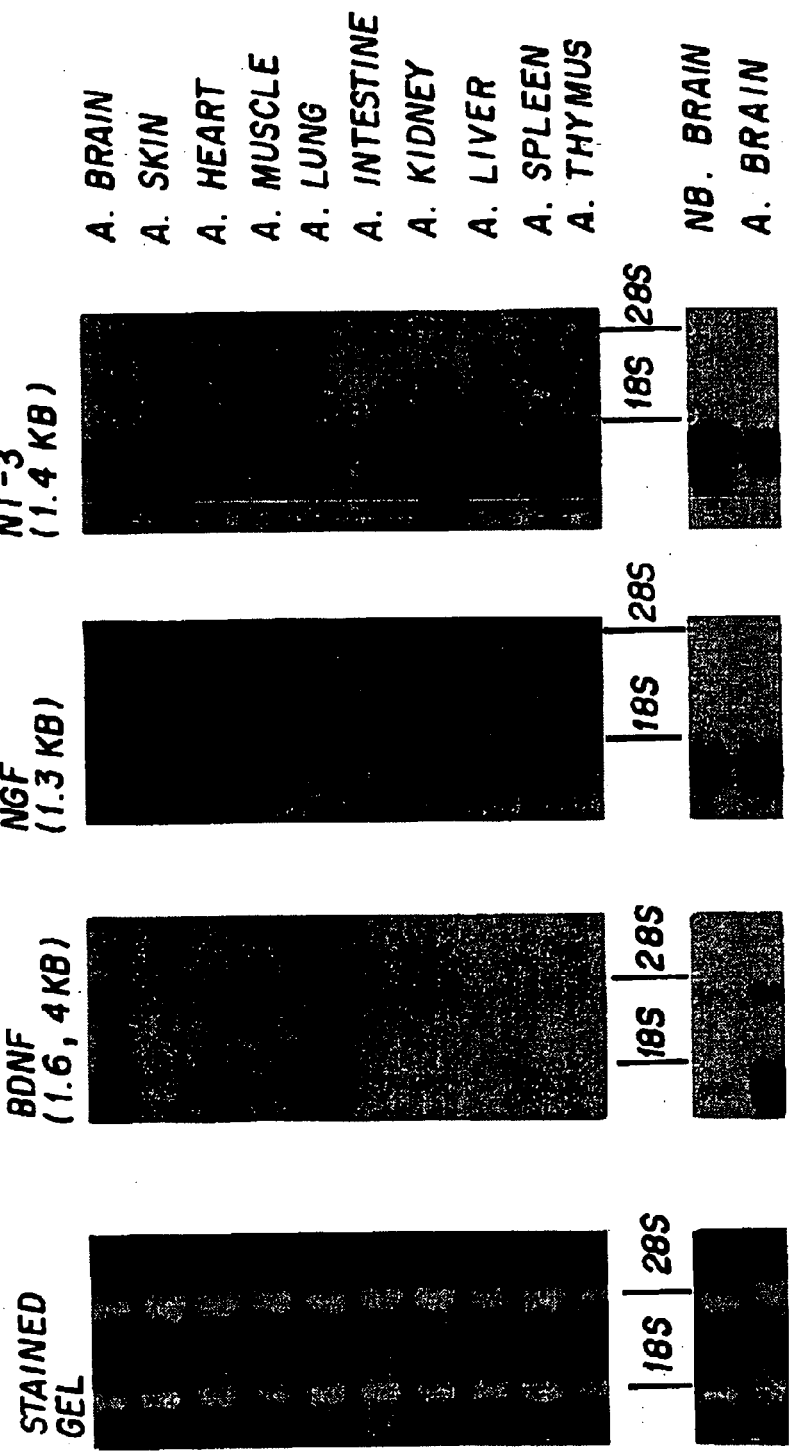

FIG. 10. Northern blot comparisons of NT-3, NGF, and BDNF expression in rodent tissues. RNA was prepared (Auffray, C. and Rougeon, F., 1980, Eur J. Biochem 107:303–14) from the indicated tissues of rat (left panels) or mouse (right panels). Ten micrograms of RNA from the indicated sources was then fractionated on 1% formaldehyde-agarose gels and transferred to nylon membranes in 10×SSC; triplicate Northern blots were hybridized (Mahmoudi, M. and Lin, V. K. 1989, Biotechniques 7:331–3) at 68° C. with $^{32}$P-labeled (Feinberg, A. P. and Vogelstein, B., 1984, Anal Biochem 137:266–7) rat NT-3, rat BDNF, and rat NGF DNA fragments, and then washed at 68° C. in 2×SSC, 0.1% SDS. DNA fragments for NT-3, NGF and BDNF were derived from the expression constructs containing these genes in pCDM8; the approximately 775 bp Xho1 inserts in these constructs were gel-purified prior to radiolabelling. A picture of the ethidium bromide stained gel, allowing comparison of the total amount of RNA per sample, is included.

FIG. 11. Aligned DNA sequences of the rat and human NT-3 genes. The predicted translation start site is indicated by "PREPRO—" and the predicted start of the mature NT-3 is indicated by "MATURE—". The mature rat and human NT-3 proteins have indentical amino acid sequences, whereas their prepro regions differ at 11 positions, which are underlined.

Figure 12:
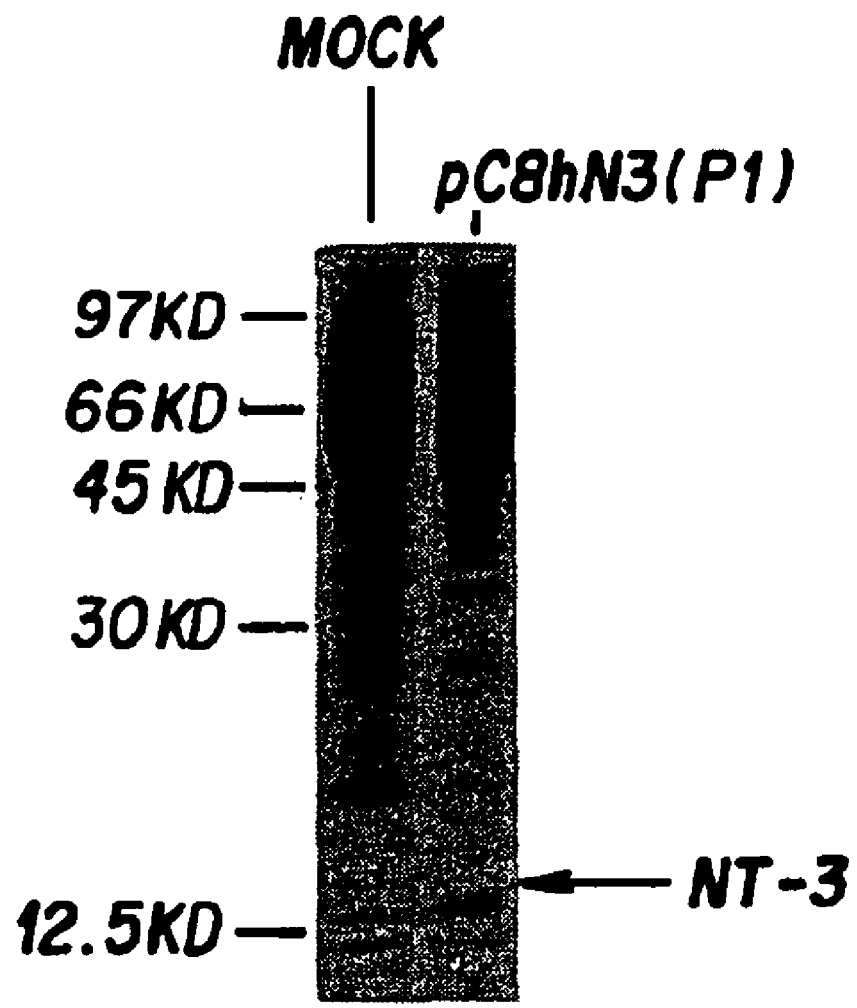

FIG. 12. Expression of human NT-3 polypeptide, detected by metabolic labeling. 5×10$^5$ COS-M5 cells per dish were seeded into 60 mm petri dishes, and grown overnight at 37° in complete DMEM medium with 10% total bovine serum (FBS). The cells were transfected (using the CaPO$_4$ method, as described by Chen and Okayama, 1987, Mol. Cell. Biol. 7:2745–52) with 20 μg of plasmid pC8-hN3(P1) containing the human NT-3 gene under regulation of a cytomegalovirus promoter, or were mock-transfected (no plasmid DNA). Forty-eight hours later, the cells were washed and incubated for 1 hour in 1 ml of methionine-free and cysteine-free DMEM with 1% FBS. A mixture of [$^{35}$S] methionine and [$^{35}$S]cysteine (100 μCi of each, from New England Nuclear) was added to each culture, cells were incubated further for 4 hours at 37°, and medium as collected. Samples of 50 μl were mixed with 25 μl of double-strength sample buffer containing Na dodecyl sulfate (SDS), boiled for 5 minutes, and subjected to electrophoresis on a 15% polyacrylamide gel in the presence of SDS (Laemmli, 1970, Nature 227:680–685). The proteins were transferred electrophoretically (3 hours, 100 mA) to a nylon membrane (immobilon, from Millipore), using buffers described by Towbin et al., 1979, Proc. Natl. Acad. Sci. U.S.A. 76:4350–4354. The filters were air dried, and labeled proteins were detected by autoradiography (16 hours at ambient temperature, using Kodak X-AR film with an enhancing screen—Cronex, DuPont).

Figure 13:
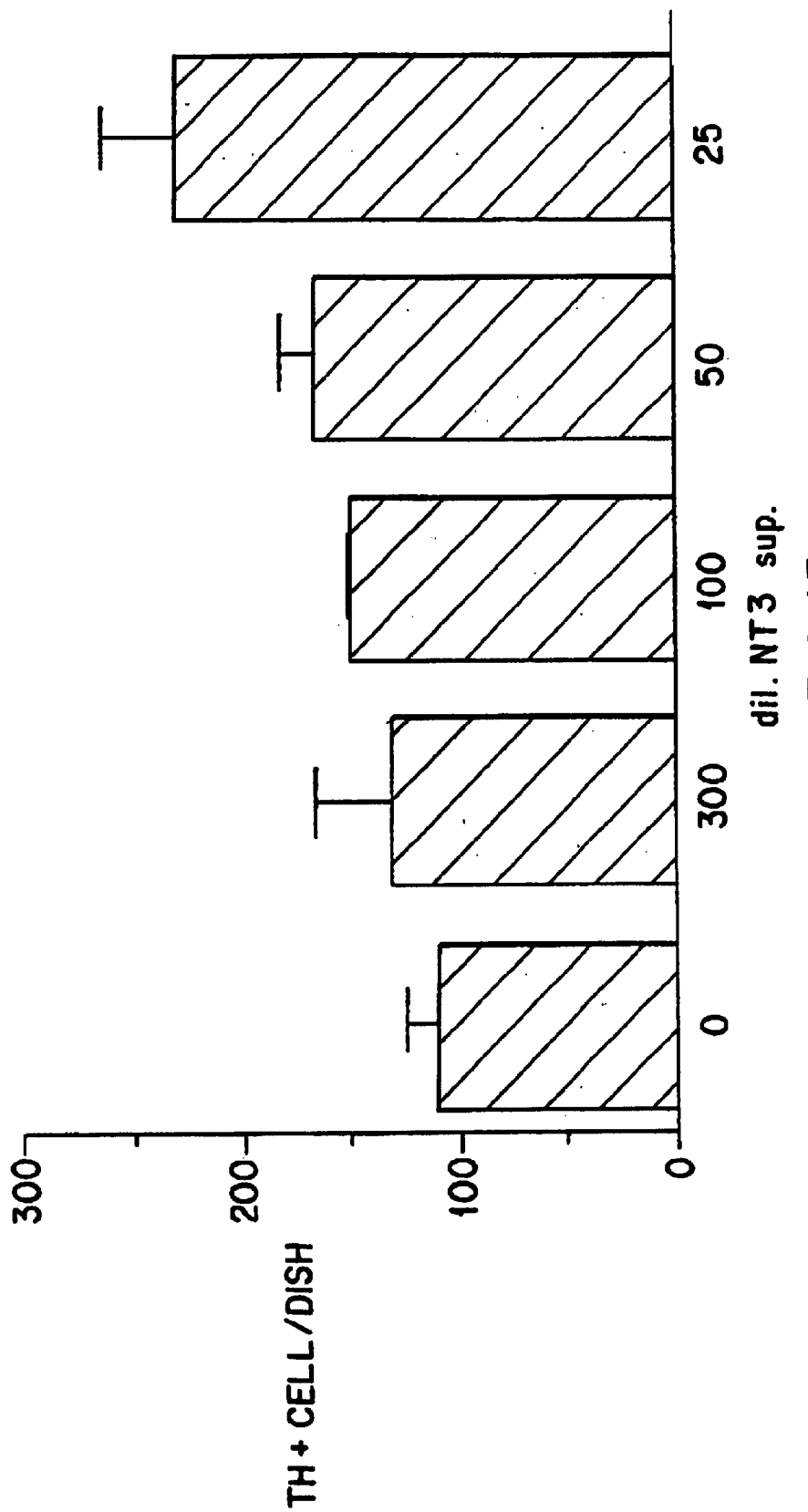

FIG. 13. Bar graph showing the number of surviving tyrosine hydroxylase cells per culture with no NT-3 supernatant (O) or dilutions of 1:300, 1:100, 1:50, or 1:25 of NT-3 containing supernatant.

Figure 14:
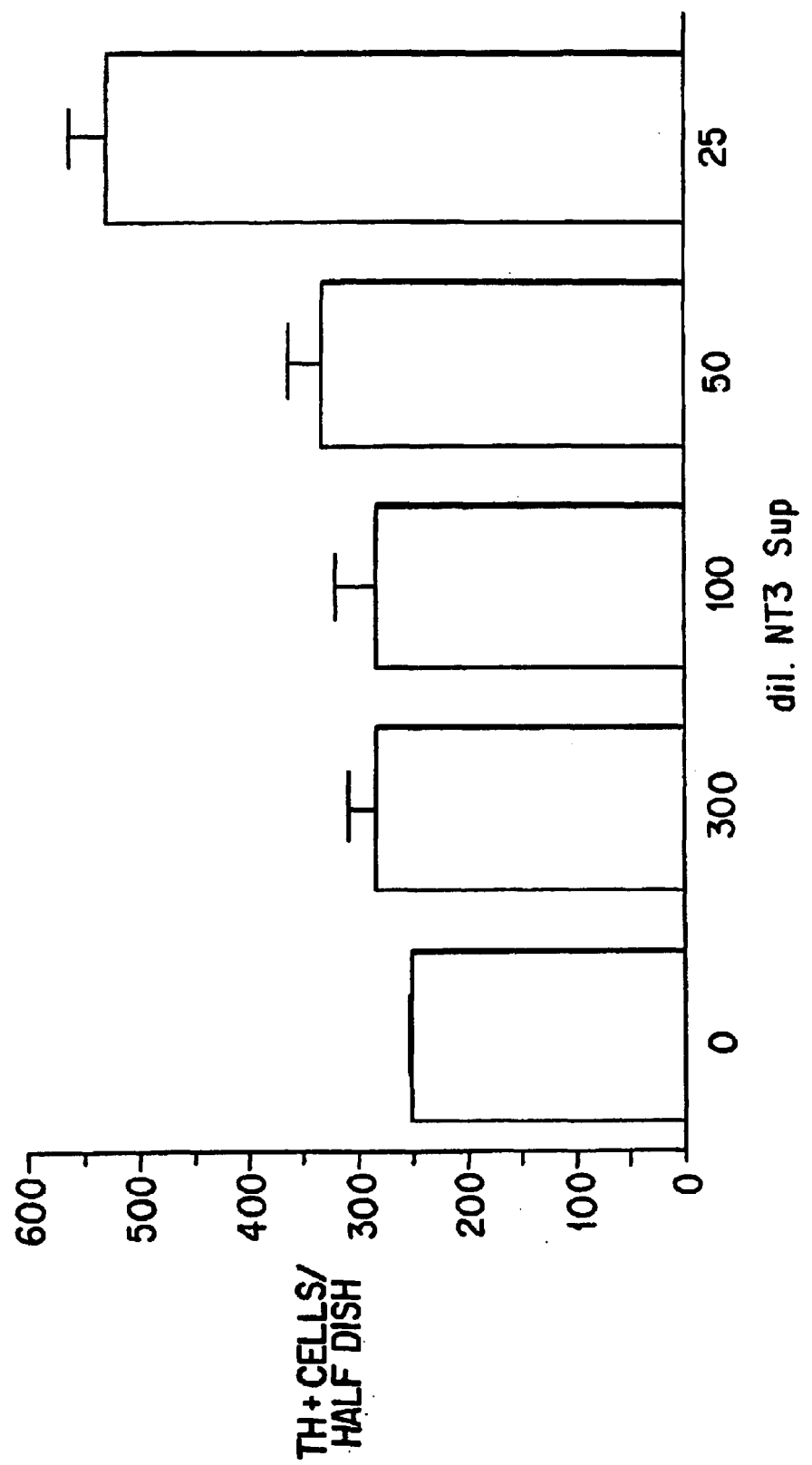

FIG. 14. Bar graph as described in legend to FIG. 13 (supra) except that cells were at a density of 900,000 cells per dish.

FIG. 15. A. Comparison of NT-3, BDNF and NGF synthetic transcripts. Dot-blot hybridization using a radiolabelled oligonucleotide homologous to a shared sequence at the 5' end of all three transcripts verifies that equal amounts (2 ng) of synthetic NT-3, BDNF and NGF transcripts, initially quantitated spectrophotometrically, are being used as defined standards. B. Determination of NT-3, BDNF and NGF mRNA levels in total RNA prepared from adult rat brain by comparison to defined synthetic RNA standards. Ten micrograms of total RNA isolated from adult rat brain, and 4, 10 and 20 pg of synthetic transcripts corresponding to each of the neurotrophins, were Northern-blotted and hybridized to radiolabelled probes specific for each of the neurotrophins.

FIG. 16. NT-3, BDNF, NGF and NGFR gene expression in total RNA (10 µg/lane) prepared from rat embryos (A), developing rat brain (B) and in selected peri-natal and adult tissues (C). Tissues: A.BR: adult brain sample standardized in FIG. 1B; PLAC: placenta; EMB: whole embryo; SP.C: spinal cord; THY: thymus; LIV: liver; HRT: heart. BR: Brain. Transcript sizes indicated (in kilobases (kb)) at right.

FIG. 17. NT-3, BDNF, NGF and NGFR gene expression in total RNA (10 µg/lane) prepared from discrete regions of the newborns (A) and adult (B) nervous systems. Regions: A.BR: adult brain sample standardized in FIG. 1B; CBL: cerebellum; HBR: Hindbrain; MBR: midbrain; DIEN: diencephelon; STR: striatum; HIP: hippocampus; CTX: neocortex; OLF: olfactory bulb; BR: whole brain without cerebellum; ADR: adrenal; RET: retina; SC.N. Sciatic nerve; SP.C: spinal cord;

FIG. 18. Quantitation of NT-3, BDNF and NGF transcript levels in newborn and adult CNS regions and peripheral tissues. Densitometric scanning of multiple exposures of Northern blots including those depicted in FIGS. 16, 17, 19 and Maisonpierre et al., (1990, Science 247:1446–1451) was used to obtain data. All levels are standardized relative to neurotrophin levels in the adult brain; levels in the adult brain, which are similar for the three neurotrophins (see text) are set at 1 for each neurotrophin. Off-scale values are included on top of broken vertical bars. Neural and non-neural samples are indicated in figure. Samples: BRN: brain not including cerebellum; CBL: cerebellum; HBR: hindbrain; MBR: midbrain; DIE: diencephalon; STR: striatum: HIP: hippocampus; CTX: neocortex; OLF: olfactory bulb; SP.C.: spinal cord; SC.N. sciatic nerve; RET: retina; ADR: adrenal; HRT: heart; LIV: liver; THY: thymus, SKN: skin; MUS: skeletal muscle; LNG: lung; INT: intestine; KID: kidney; SPL: spleen.

FIG. 19. NT-3, BDNF, NGF and NGFR gene expression during development of the spinal cord (A,E), cerebellum (B,F), and hippocampus (C,G). 10 µg of total RNA prepared from the indicated developmental timepoints were compared for their expression of the various transcripts. Densitometric quantitation of neurotrophin transcript levels depicted in E,F,G.

5. DETAILED DESCRIPTION OF THE INVENTION

The present invention relates to neurotrophin-3, a new member of the BDNF/NGF family of neurotrophic molecules, as well as to other members of the BDNF/NGF family which may be identified using similar methodology.

For clarity of disclosure, and not by way of limitation, the detailed description of the invention will be divided into the following sub-sections.

(i) identification of additional members of the BDNF/NGF family;

(ii) the cloning of neurotrophin-3;

(iii) expression of neurotrophin-3;

(iv) assay of the biological activity of neurotrophin-3;

(v) neurotrophin-3 genes and proteins;

(vi) generation of anti-neurotrophin-3 antibodies; and (vii) utility of the invention.

5.1. Identification of Additional Members of the BDNF/NGF Family

NGF and BDNF are basic proteins of approximately 120 amino acids that share about 50% amino acid sequence identity, including absolute conservation of six cysteine residues that, in active NGF, have been shown to form three disulfide bridges (Bradshaw, A., 1978, Ann. Rev. Biochem. 47:191–216; Leibrock et al., 1989, Nature 341:149–52). Comparison of the sequences of NGF from evolutionarily divergent species has revealed that the amino acids flanking these cysteine residues comprise the most highly conserved regions of the molecule (Meier et al., 1986, EMBO J. 5:1489–93; Selby et al., 1987, J. Neurosci. Res. 18:293–8). Strikingly, these are also the regions which are most similar between BDNF and NGF (Leibrock et al., 1989, Nature 341:149–52).

A rational search for additional members of the BDNF/NGF gene family may be carried out using an approach that takes advantage of the existence of the conserved segments of strong homology between NGF and BDNF. For example, additional members of the BDNF gene family may be identified by selecting, from among a diversity of nucleic acid sequences, those sequences that are homologous to BDNF and NGF, and further identifying, from among the selected sequences, those that also contain nucleic acid sequences which are non-homologous to NGF and BDNF. The term "non-homologous" may be construed to mean a region which contains at least about 6 contiguous nucleotides in which at least about two nucleotides differ from NGF and BDNF sequence.

The present invention also relates to recombinant DNA molecules which are homologous to BDNF and NT-3, or, alternatively, to NGF and NT-3, but which also contain regions non-homologous to BDNF and NT-3, or NGF and NT-3, respectively. These additional members of the BDNF/NGF/NT-3 gene family may be identified using molecular probes which correspond to regions of homology. Upon further analysis, these members of the BDNF/NGF/NT-3 gene family are found to possess sequences which differ from sequences of known members of the BDNF/NGF/NT-3 gene family.

For example, a preferred specific embodiment of the invention provides the following method. Corresponding to each of the four conserved segments ("boxes") set forth in Table III, infra, sets of degenerate oligonucleotide probes of about 10–20 nucleotides may be synthesized, representing all of the possible coding sequences for the amino acids found in either NGF or BDNF for about three to seven contiguous codons. Numbering with respect to the amino terminus of the mature polypeptides (so that His134 of preproBDNF is treated as His1 in the mature protein), the four boxes may be characterized as follows (numbered relative to human mature proteins.

TABLE III

| Box 1: | NGF | Gly10 | - Ser19 |
|--------|------|-------|---------|
|        | BDNF | Gly8  | - Ser17 |

TABLE III-continued

| Box 2: | NGF | Lys50 | - Cys58 |
| | BDNF | Lys50 | - Cys58 |
| Box 3: | NGF | Gly67 | - Asp72 |
| | BDNF | Gly67 | - Asp72 |
| Box 4: | NGF | Trp99 | - Cys110 |
| | BDNF | Trp100 | - Cys111 |

Synthetic oligonucleotides derived from sequence pairs from the boxes set forth in Table III may be utilized as primers to amplify by PCR sequences from a source (RNA or DNA) of potential interest. This might include mRNA or cDNA or genomic DNA from any eukaryotic species that could express a polypeptide closely related to BDNF or NGF. By carrying out as few as six PCR reactions (namely: a primer from Box 1 with a primer from Box 2; Box 1 with Box 3; Box 1 with Box 4; Box 2 with Box 3; Box 2 with Box 4; Box 3 with Box 4), it may be possible to detect a gene or gene product sharing any two of the four above segments of conserved sequence between NGF and BDNF. If one chooses to synthesize several different degenerate primers for each box, it may still be possible to carry out a complete search with a reasonably small number of PCR reactions. It is also possible to vary the stringency of hybridization conditions used in priming the PCR reactions, to allow for greater or lesser degrees of nucleotide sequence similarity between the unknown gene and NGF or BDNF. If a segment of a previously unknown member of the BDNF/NGF gene family is amplified successfully, that segment may be molecularly cloned and sequenced, and utilized as a probe to isolate a complete cDNA or genomic clone. This, in turn, will permit the determination of the unknown gene's complete nucleotide sequence, the analysis of its expression, and the production of its protein product for functional analysis.

In addition, the present invention provides for the use of the BDNF/NGF sequence homologies in the design of novel recombinant molecules which are members of the BDNF/NGF gene family but which may not occur in nature. For example, and not by way of limitation, a recombinant molecule can be constructed according to the invention, comprising portions of both NGF and BDNF genes. Such a molecule could exhibit properties associated with both BDNF and NGF and portray a novel profile of biological activities, including agonists as well as antagonists. Primary sequence of BDNF and NGF may also be used to predict tertiary structure of the molecules using computer simulation (Hopp and Woods, 1981, Proc. Natl. Acad. Sci. U.S.A. 78:3824–3828); BDNF/NGF chimeric recombinant genes could be designed in light of correlations between tertiary structure and biological function. Likewise, chimeric genes comprising portions of any one or more members of BDNF/NGF gene family may be constructed.

5.2. The Cloning of Neurotrophin-3

The NT-3 gene from any organism may be identified using the regions of homology shared by BDNF and NGF using the methods set forth above. In two preferred, specific embodiments of the invention, the gene may be identified and cloned as follows.

In one preferred embodiment, a sense (or 5') primer, having the nucleotide sequence (using IUPAC nomenclature) GGGGATCCGC GGI TGY MGI GGI ATH GA (primer 1, which includes Bam HI and Sac II endonuclease cleavage sites) and an antisense (or 3') primer, having the nucleotide sequence TCGAATTCTAG AT ICK IAT RAA ICK CCA (primer 2, which includes Eco RI and Xba I sites), may be used in polymerase chain reaction (Saiki et al., 1985, Science 230: 1350–1354) with a commercial thermal cycler (e.g. the Perkin-Elmer Cetus thermal cycler) and thermostabile DNA polymerase from *thermus aquaticus* (Taq polymerase) polymerase. After about four cycles with an annealing temperature of 45° C., the remaining 36 cycles may be performed with annealings at 49° C. The resulting DNA products of the amplification may then be separated by polyacrylamide gel electrophoresis, and the product corresponding to the expected size (about 137 base pairs) may be eluted, reamplified, and then digested with two restriction endonucleases, one of which cleaves the NGF gene sequence of the organism within the segment amplified, the other of which cleaves the BDNF gene sequence of the organism within the amplified segment. The uncleaved DNA (which presumably does not encode either NGF or BDNF, having escaped restriction endonuclease cleavage) may then be separated from cleaved DNA by polyacrylamide gel electrophoresis, eluted, and asymmetrically amplified (Innis et al., 1988, Proc. Natl. Acad. Sci. U.S.A. 85:9436–9440) and sequenced (Sanger et al., 1979, Proc. Natl. Acad. Sci. U.S.A. 72:3918–3921) using, for example, primers 1 and 2. Based on the sequence thereby obtained, additional sense and antisense primers may be designed which more precisely reflect the sequence of the novel gene. For example, additional sense primers such as GGGATTGATGAC AAA (primer 3) and ACTCTCAGTGCAAAACTTCGC (primer 4), and antisense (5') primer CGGATCCGAATTCTGCAG $(T)_{12}V$ (primer 5) may be used. RNA, prepared from a tissue likely to produce neurotrophic activity, such as brain (using any standard method, such as that set forth in Okayama et al., 1987, Meth. Enzymol. 154:3–28), may be reverse transcribed using, for example, primer 5, which is designed to match 3' poly (A) tails and contains restriction endonuclease cleavage sites for Bam HI, EcoRI, and PstI (Leibrock et al., 1989, Nature 341: 149–152). The resulting cDNA may then be PCR-amplified using primers 3 and 5, and then reamplified using primers 4 and 5. A Southern blot may then be produced using the products of the last reaction, and hybridized to a $^{32}P$-end-labeled oligonucleotide probe corresponding to sequence downstream of primer 3 and 4 sequences. The DNA fragments thus identified may then be cloned into a suitable vector, and the longest insert obtained may be used to screen a genomic library produced from the organism of interest. Positive clones identified in this manner may then be analyzed by standard restriction mapping and nucleotide sequencing techniques.

In another preferred embodiment of the invention, degenerate oligonucleotides corresponding to segments of four protein sequences highly conserved between NGF and BDNF may be synthesized. For example, these amino acid sequences (presented in FIG. 7D) may be (1) Gly-Glu-(Tyr/Phe)-Ser-Val-Cys-Asp-Ser; (2) Lys-Gen-Tyr-Phe-(Tyr/Phe)-Glu-Thr-Lys-Cys; (3) Gly-Cys-Arg-Ile-Asp; and (4) Trp-Arg-Phe-Ile-Arg-Ile-Asp-Thr-(Ser/Ala)-Cys-Val-Cys. A series of degenerate sense and anti-sense oligonucleotides (containing a degenerate portion 15–26 nucleotides long, corresponding to 5–9 amino acids of the above-mentioned protein sequences in either the sense or anti-sense direction, as well as a non-degenerate "tail" encoding restriction enzyme recognition sites) may be used in PCR reactions. Amplification reactions between pairs of upstream sense and downstream anti-sense primers may be performed under standard conditions or, preferably, optimal conditions for each primer pair may be experimentally determined. For example, the sense primer (corresponding to amino acid sequence (1), supra) 5'GACTCGAGTCGACATCG-GTN-TGY-GAY-WSN-RTN-WS-3' and the anti-sense primer (corresponding to amino acid sequence (2), supra), 5'-CCAAGCTTCTAGAATTC-CA-YTT-NGT-YTC-RWA-RAA-RTA-YTG-3' may be used in the amplification reaction using genomic DNA or cDNA derived from a suitable source as template. The products of amplification reactions using pairs of upstream sense and downstream anti-sense primers may be used as hybridization probes on Southern blots of genomic DNA to identify PCR product which hybridizes to genomic DNA sequence which contains regions homologous to the probes as well as regions non-homologous to the probes (for example, non-NGF, non-BDNF sequence). A PCR product which identifies a novel genomic DNA sequence may be used to screen genomic or cDNA libraries and thereby select clones encoding novel members of the BDNF/NGF gene family.

5.3. Expression of Neurotrophin-3

The nucleotide sequence coding for a NT-3 protein, or a portion thereof, can be inserted into an appropriate expression vector, i.e., a vector which contains the necessary elements for the transcription and translation of the inserted protein-coding sequence. The necessary transcriptional and translation signals can also be supplied by the native NT-3 gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. In preferred embodiments of the invention, the expression vector may comprise the CMV promoter (Stephens and Cockett, 1989, Nucl. Acids Res. 17:7110) and SV40 origin of replication. The expression elements of these vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinations (genetic recombination). Expression of nucleic acid sequence encoding a NT-3 protein or peptide fragment may be regulated by a second nucleic acid sequence so that NT-3 protein or peptide is expressed in a host transformed with the recombinant DNA molecule. For example, expression of NT-3 may be controlled by any promoter/enhancer element known in the art. Promoters which may be used to control NT-3 expression include, but are not limited to, the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:144–1445), the regulatory sequences of the metallothionine gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25), see also "Useful proteins from recombinant bacteria" in Scientific American, 1980, 242:74–94; plant expression vectors comprising the nopaline synthetase promoter region (Herrera-Estrella et al., Nature 303:209–213) or the cauliflower mosaic virus 35S RNA promoter (Gardner, et al., 1981, Nucl. Acids Res. 9:2871), and the promoter for the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phophatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the bran (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing NT-3 gene inserts can be identified by three general approaches: (a) DNA—DNA hybridization, (b) presence or absence of "marker" gene functions, and (c) expression of inserted sequences. In the first approach, the presence of a foreign gene inserted in an expression vector can be detected by DNA—DNA hybridization using probes comprising sequences that are homologous to an inserted NT-3 gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the NT-3 gene is inserted within the marker gene sequence of the vector, recombinants containing the NT-3 insert can be identified by the absence of the marker gene function. In the third approach, recombinant expression vectors can be identified by assaying the foreign gene product expressed by the recombinant. Such assays can be based, for example, on the physical or functional properties of the NT-3 gene product in bioassay systems.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered NT-3 protein may be controlled. Furthermore, different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of the heterologous NT-3 protein. Furthermore, different vector/host expression systems may effect processing reactions such as proteolytic cleavages to different extents.

In a specific embodiment of the invention, DNA encoding preproNT-3 may be cloned into pCMV plasmid, amplified, and then used to transfect COS cells by the calcium phosphate method (Chen and Okayama, 1987, Mol. Cell. Biol. 7:2745–2752); NT-3 activity may then be collected from cell culture medium (see Example Sections 6 and 7, infra).

Figure 7B:
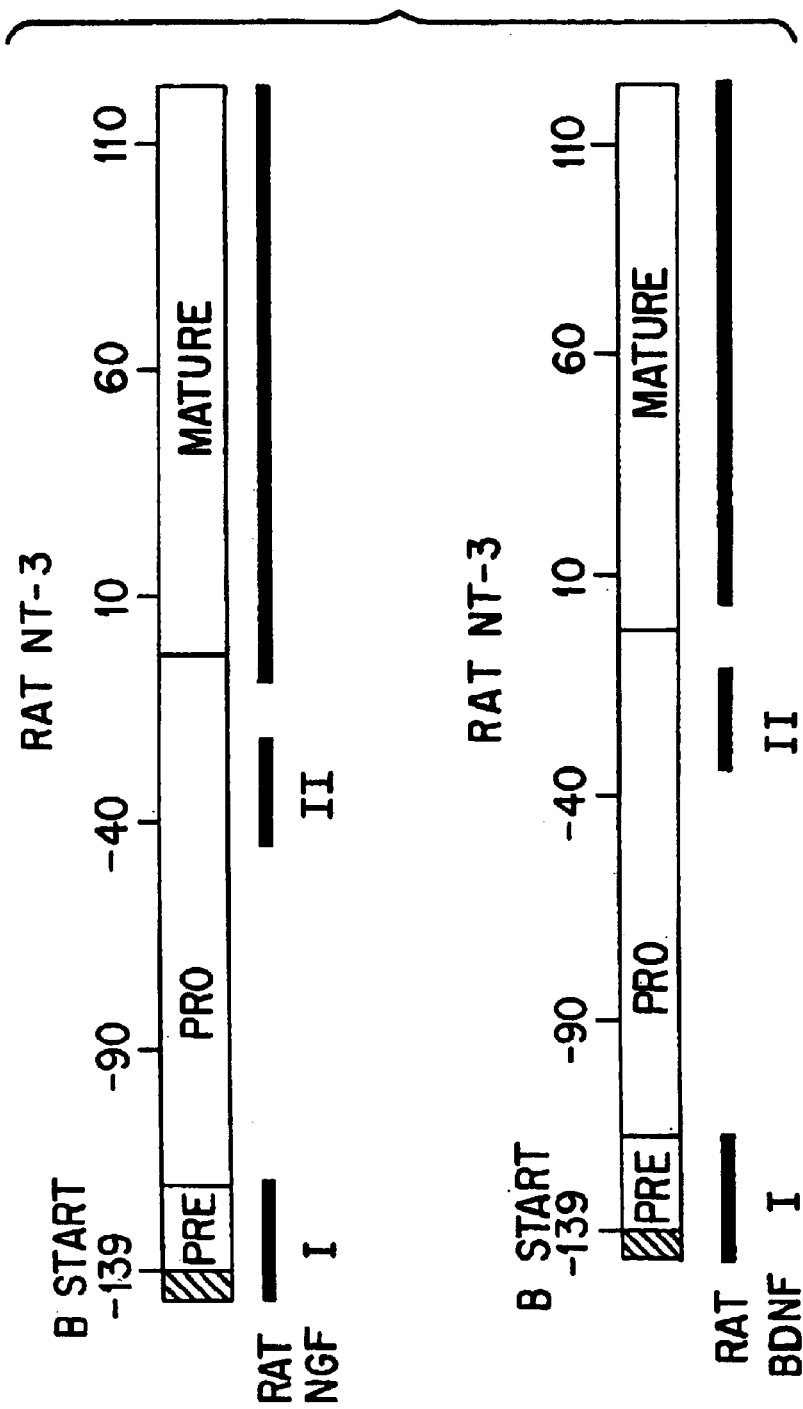
Figure 8I:
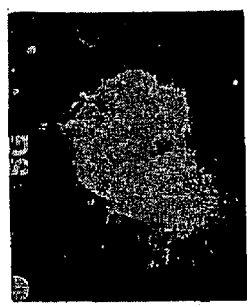
Figure 8J:
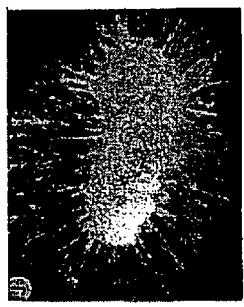
Figure 8K:
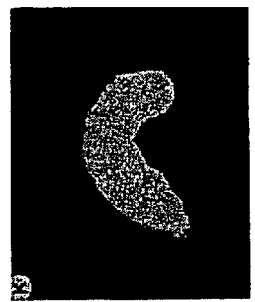
Figure 8L:
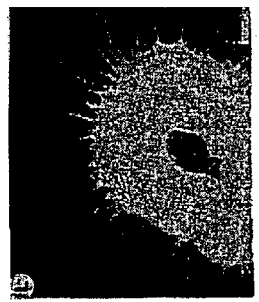

It has been appreciated that NGF is synthesized in two different precursor forms, a long form and a short form (Darling et al., 1983, Cold Spring Harbor Symp. Quant. Biol. 48:427–483). The shorter form is substantially analogous to the prepro forms of BDNF and NT-3. According to the invention, it may be desirable to utilize expression systems comprising DNA encoding an analogous long form of BDNF or NT-3. DNA encoding these long precursor forms may be identified by sequencing cDNA or genomic DNA regions upstream of the mature BDNF or NT-3 peptide encoding regions and locating open translational reading frame. Alignment of the NT-3 gene sequence with the sequences of NGF and BDNF has allowed the prediction of long and short precursors for NT-3 protein (FIG. 7B). The effectiveness of mature BDNF or NT-3 expression from long or short precursor forms may depend on the expression system used, and may vary from one type of cell line to another.

5.3.1. Identification and Purification of the Expressed Gene Product

Once a recombinant which expresses the NT-3 gene is identified, the gene product may be analyzed. This can be achieved by assays based on the physical or functional properties of the product including radioactive labelling of the product followed by analysis by gel electrophoresis.

Once the NT-3 protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay, including, but not limited to, chick embryo dorsal root ganglia, neural placode-derived or sympathetic ganglion neurons.

5.4. Assay of Biological Activity of Neurotrophin-3

Any system which qualitatively or quantitatively indicates NT-3 activity may be used according to the present invention. Because NT-3, in contrast to BDNF and NGF, promotes neurite outgrowth from both neural-placode derived nodose ganglion and sympathetic ganglia, either of these systems, in addition to the dorsal root ganglion (DRG) culture system, may be used as an NT-3 bioassay. The DRG assay may be performed as described in Barde et al. (1980, Proc. Natl. Acad. Sci. U.S.A. 77:1199–1203). The nodose ganglion assay system may be performed as described in Lindsay et al. (1985, Dev. Biol. 112:319–328). The sympathetic ganglion assay system may be performed as described in Barde et al. (1982, EMBO J., 1:549–553).

5.5. Neurotrophin-3 Genes and Proteins

Using the methods detailed supra and in Example Sections 6 and 7, infra, the following nucleic acid sequences were determined, and their corresponding amino acid sequences deduced. The mouse genomic NT-3 sequence was determined, and is depicted in FIG. 2. The sequence of rat NT-3 is presented in FIG. 7. The genomic human DNA NT-3 sequence was determined, and is depicted in FIG. 11 which also presents DNA sequences from rat. Each of these sequences, or their functional equivalents, can be used in accordance with the invention. Additionally, the invention relates to NT-3 genes and proteins isolated from porcine, bovine, feline, avian, equine, or canine, as well as primate sources and any other species in which NT-3 activity exists. The invention is further directed to subsequences of NT-3 nucleic acids comprising at least ten nucleotides, such subsequences comprising hybridizable portions of the NT-3 sequence which have use, e.g., in nucleic acid hybridization assays, Southern and Northern blot analyses, etc. The invention also provides for NT-3 protein, and fragments and derivatives thereof, according to the amino acid sequences set forth in FIGS. 2, 7 and 11 or their functional equivalents. The invention also provides fragments or derivatives of NT-3 proteins which comprise antigenic determinant(s) or which are functionally active. As used herein, functionally active shall mean having positive activity in assays for known NT-3 function, e.g. chick embryo DRG, nodose ganglion and sympathetic ganglion assays.

For example, the nucleic acid sequences depicted in FIGS. 2, 7 and 11 can be altered by substitutions, additions or deletions that provide for functionally equivalent molecules. Due to the degeneracy of nucleotide coding sequences, other DNA sequences which encode substantially the same amino acid sequence as depicted in FIGS. 2, 7 and 11 may be used in the practice of the present invention. These include but are not limited to nucleotide sequences comprising all or portions of the NT-3 genes depicted in FIGS. 2, 7 and 11 which are altered by the substitution of different codons that encode a functionally equivalent amino acid residue within the sequence, thus producing a silent change. Likewise, the NT-3 proteins, or fragments or derivatives thereof, of the invention include, but are not limited to, those containing, as a primary amino acid sequence, all or part of the amino acid sequence substantially as depicted in FIGS. 2, 7 and 11 including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are NT-3 proteins or fragments or derivatives thereof which are differentially modified during or after translation, e.g., by glycosylation, proteolytic cleavage, linkage to an antibody molecule or other cellular ligand, etc.

Additionally, a given NT-3 can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, et al., 1978, J. Biol. Chem. 253:6551), use of TAB® linkers (Pharmacia), etc.

5.6. Generation of Anti-Neurotrophin-3 Antibodies

According to the invention, NT-3 protein, or fragments or derivatives thereof, may be used as immunogen to generate anti-NT-3 antibodies.

To further improve the likelihood of producing an anti-NT-3 immune response, the amino acid sequence of NT-3 may be analyzed in order to identify portions of the molecule which may be associated with increased immunogenicity. For example, the amino acid sequence may be subjected to computer analysis to identify surface epitopes, according to the method of Hopp and Woods (1981, Proc. Natl. Acad. Sci. U.S.A. 78:3824–3828) which has been successfully used to identify antigenic peptides of Hepatitis B surface antigen. Alternatively, the deduced amino acid sequences of NT-3 from different species could be compared, and relatively non-homologous regions identified; these non-homologous regions would be more likely to be immunogenic across various species.

For preparation of monoclonal antibodies directed toward NT-3, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies for therapeutic use may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of NT-3. For the production of antibody, various host animals can be immunized by injection with NT-3 protein, or fragment or derivative thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and, *Corynebacterium parvum.*

A molecular clone of an antibody to a NT-3 epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the 2 Fab or Fab fragments which can be generated by treating the antibody molecule with papain and a reducing agent.

5.7. Utility of the Invention

The present invention relates to the nucleic acid sequence of NT-3 and to the substantially pure protein, peptide fragments, or derivatives produced therefrom. NT-3 may be produced in quantities sufficient for diagnostic and therapeutic applications. Likewise, anti-NT-3 antibodies and NT-3 nucleic acid probes may be utilized in diagnostic and therapeutic applications. For most purposes, it is preferable to use NT-3 genes or gene products from the same species for diagnostic or therapeutic purposes, although cross-species utility of NT-3 may be useful in specific embodiments of the invention.

5.7.1. Diagnostic Applications

The present invention, which relates to nucleic acids encoding NT-3 and to proteins, peptide fragments, or derivatives produced therefrom, as well as antibodies directed against NT-3 protein, peptides, or derivatives, may be utilized to diagnose diseases and disorders of the nervous system which may be associated with alterations in the pattern of NT-3 expression.

In various embodiments of the invention, NT-3 genes and related nucleic acid sequences and subsequences, including complementary sequences, may be used in diagnostic hybridization assays. The NT-3 nucleic acid sequences, or subsequences thereof comprising about 15 nucleotides, can be used as hybridization probes. Hybridization assays can be used to detect, prognoses diagnose, or monitor conditions, disorders, or disease states associated with changes in NT-3 expression, including, in particular, conditions resulting in sensory neuron damage. Such diseases and conditions include but are not limited to CNS trauma, infarction, infection, degenerative nerve disease, malignancy, or postoperative changes including but not limited to Alzheimer's Disease, Parkinson's Disease, and Huntington's Chorea. For example, total RNA in a tissue sample from a patient can be assayed for the presence of NT-3 mRNA, wherein a change in the amount of NT-3 mRNA is indicative of neuronal degeneration.

In alternate embodiments of the invention, antibodies directed toward NT-3 protein, peptide fragments, or derivatives can be used to diagnose diseases and disorders of the nervous system, including, in particular, sensory disorders and degenerative diseases of the retina, as well as those disorders and diseases listed supra. The antibodies of the invention can be used, for example, in in situ hybridization techniques using tissue samples obtained from a patient in need of such evaluation. In a further example, the antibodies of the invention can be used in ELISA procedures to detect and/or measure amounts of NT-3 present in tissue or fluid samples; similarly, the antibodies of the invention can be used in Western blot analysis to detect and/or measure NT-3 present in tissue or fluid samples.

In further embodiments of the invention, NT-3 protein, peptide fragments or derivatives can be used to diagnose diseases and disorders of the nervous system. In a particular embodiment and not by way of limitation, labeled NT-3 protein or peptide fragments can be used to identify tissues or cells which express the NT-3 receptor in order to identify aberrancies of NT-3 receptor expression and consequently, potential abnormalities in the tissue or cellular response to NT-3.

5.7.2. Therapeutic Applications

The present invention, which relates to nucleic acids encoding NT-3, and to proteins, peptide fragments, or derivatives produced therefrom, as well as to antibodies directed against NT-3 protein, peptides, or derivatives, may be utilized to treat diseases and disorders of the nervous system which may be associated with alterations in the pattern of NT-3 expression or which may benefit from exposure to NT-3 or anti-NT-3 antibodies.

In various embodiments of the invention, NT-3 protein, peptide fragments or derivatives can be administered to patients in whom the nervous system has been damaged by trauma, surgery, ischemia, infection, metabolic disease, nutritional deficiency, malignancy, or toxic agents. In various specific embodiments of the invention, NT-3 can be locally administered to sensory neurons which have been severed, including, but not limited to, neurons in dorsal root ganglia or in any of the following tissues: the geniculate, petrosal, and nodose ganglia; the vestibuloacoustic complex of the VIIIth cranial nerve; the ventrolateral pole of the maxillo-mandibular lobe of the trigeminal ganglion, the mesencephalic trigeminal nucleus and sympathetic ganglia. It may be desirable to administer the NT-3-related peptides or NT-3 protein by adsorption onto a membrane, e.g. a silastic membrane, that could be implanted in the proximity of the severed nerve. The present invention can also be used for example in hastening the recovery of patients suffering from diabetic neuropathies, e.g. mononeuropathy multiplex and diabetic peripheral neuropathy.

In addition to diabetic neuropathy, NT-3 or NT-3 related peptides may also be used to treat other peripheral neuropathies, including but not limited to the following: virus-associated neuropathies, including acquired immuno-deficiency syndrome (AIDS) related neuropathy, infectious mononucleosis with polyneuritis, viral hepatitis with poly-neuritis; Guillian-Barre syndrome; botulism-related neuropathy; toxic polyneuropathies including lead and alcohol-related neuropathies; nutritional neuropathies including subacute combined degeneration; angiopathic neuropathies including neuropathies associated with systemic lupus erythematosis; sarcoid-associated neuropathy; carcinomatous neuropathy; compression neuropathy (e.g. carpal tunnel syndrome) and hereditary neuropathies. Hereditary neuropathies which may be treated using NT-3 or NT-3 related proteins include peroneal muscular atrophy, familial dysautomia and progressive hypertrophic neuropathy.

In further embodiments of the invention, NT-3 protein or peptide fragments or derivatives derived therefrom, can be used to treat congenital conditions or neurodegenerative disorders, including, but not limited to, Alzheimer's disease, Parkinson's disease, multiple sclerosis, amyotrophic lateral sclerosis, and Huntington's chorea.

In a specific embodiment of the invention, administration of NT-3 protein, or peptide fragments or derivatives derived therefrom, can be used in conjunction with surgical implantation of tissue in the treatment of Alzheimer's disease and/or Parkinson's disease. As shown in Section 11, infra, NT-3 promotes the survival of dopaminergic neurons; as dopaminergic neurons are destroyed in Parkinson's disease, NT-3 may be used in methods of treating Parkinson's disease comprising administering an effective amount of NT-3 to a patient in need of such treatment. It has been shown that approximately 35 percent of patients with Parkinson's disease suffer from Alzheimer-type dementia; NT-3 produced according to the invention may prove to be a useful single agent therapy for this disease complex. Similarly, NT-3 produced according to the invention may be used therapeutically to treat Alzheimer's disease in conjunction with Down's Syndrome. In addition, as shown in Section 12, infra, NT-3 is expressed at high levels during development and differentiation of the nervous system; accordingly, NT-3 may be used in the treatment of developmental nervous system disorders, such as Down's syndrome, and also in the treatment of disorders related to de-differentiation of cells, such as malignancies, or in disorders which may benefit from regeneration in the nervous system. NT-3 produced according to the invention can be used in the treatment of a variety of dementias as well as congenital learning disorders.

In further embodiments of the invention, NT-3 protein, fragments or derivatives can be used in conjunction with other cytokines to achieve a desired neurotrophic effect. For example, and not by way of limitation, according to the invention NT-3 can be used together with a second agent, for example, NGF or BDNF, to achieve a synergistic stimulatory effect on growth of neurons and/or in maintaining survival and/or restoring or enhancing function wherein synergistic is construed to mean that the effect of the combination of NT-3 protein, peptide fragment, or derivative and a second agent achieves an effect greater than the same amount of either substance used individually. It is envisioned that NT-3 may function synergistically with other CNS-derived peptide factors yet to be fully characterized, in the growth, development, maintenance of differentiated function and survival of a wide array of neuronal subpopulations in the central nervous system. Alternatively, the effects of NT-3 and a second neurotrophic agent may be additive.

It is further envisioned that, based on the full characterization of the NT-3 molecule, novel peptide fragments, derivatives, or mutants of NT-3 may be developed which are capable of acting as antagonists of some, or all of the biological functions of NT-3. Such NT-3 antagonists may be useful in the selective ablation of sensory neurons, for example, in the treatment of chronic pain syndromes.

In still further embodiments of the invention, antibodies directed toward NT-3 protein, or peptide fragments or derivatives thereof, can be administered to patients suffering from a variety of neurologic disorders and diseases and who are in need of such treatment. For example, patients who suffer from excessive production of NT-3 may be in need of such treatment. Anti-NT-3 antibodies can be used in prevention of aberrant regeneration of sensory neurons (e.g. post-operatively), or, as discussed supra, in the treatment of chronic pain syndromes.

The tissue distribution of NT-3, as described in Sections 6 and 7 infra, indicate that higher levels of NT-3 mRNA are expressed in brain, kidney, heart, and spleen, among other tissues. The NT-3 produced in non-neural tissues may or may not be identical to NT-3 expressed in brain. A single species of NT-3 may function in both neural and non-neural tissues; disorders in the expression of NT-3 may underlie diseases which affect the nervous system as well as other organ systems. Alternatively, a closely related family of NT-3 molecules may subserve different functions in neural and non-neural tissues. The NT-3 molecules of the invention may, therefore, be useful in the treatment of diseases which affect neural as well as the neural regulation of non-neural tissues, including in particular, the heart, the hematopoietic, renal and reticuloendothelial systems.

Furthermore, as exemplified in Section 6, infra, NT-3 expression is increased in immature animals compared to adult animals. According to the invention, NT-3 may be particularly useful in the treatment of developmental disorders or, alternatively, in inducing renovation of the nervous system following CNS injury.

5.8. Pharmaceutical Compositions

The active compositions of the invention, which may comprise all or portions of the NT-3 gene product, including protein, peptide fragments or derivatives produced therefrom, or antibodies (or antibody fragments) directed toward NT-3 protein, peptide fragments, or derivatives, or a combination of NT-3 and at least one other agent, such as NGF or BDNF, may be administered in any sterile biocompatible pharmaceutical carrier, including, but not limited to, saline, buffered saline, dextrose, and water.

NT-3 protein, peptide fragment or derivative may comprise an amino acid sequence or subsequence thereof substantially as depicted in FIG. 2, 7 or 11; it may be preferable to use NT-3 protein comprising, in particular, all or a portion of the amino acid sequence from about amino acid 140 to about amino acid 258, as depicted in FIG. 2, from about amino acid 1 to about amino acid 119 in FIG. 7, or from the first amino acid labeled "mature" in FIG. 11, to the end of the peptide sequence depicted therein, or a functionally equivalent sequence, as this subsequence is believed to comprise the functional portion of the NT-3 molecule. NT-3 may be derived from sequences corresponding to the NT-3 genes of any suitable species, including, but not limited to, human, pig, rat, chicken, cow, dog, sheep, goat, cat, rabbit, etc.

The amount of NT-3 protein, peptide fragment, derivative, or antibody which will be effective in the treatment of a particular disorder or condition will depend on the nature of the disorder or condition, and can be determined by standard clinical techniques. Where possible, it is desirable to determine the dose-response curve and the pharmaceutical compositions of the invention first in vitro, e.g. in the NT-3 bioassay systems described supra, and then in useful animal model systems prior to testing in humans. Based on in vitro data, in a specific embodiment of the invention, a pharmaceutical composition effective in promoting the survival of sensory neurons may provide a local NT-3 protein concentration of between about 0.1–10 µg/ml.

Methods of introduction include but are not limited to intradermal, intramuscular, intraperitoneal, intravenous, subcutaneous, oral, and intranasal. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

Further, it may be desirable to administer the pharmaceutical compositions of the invention locally to the area in need of treatment; this may be achieved by, for example, and not by way of limitation, local infusion during surgery, by injection, by means of a catheter, or by means of an implant, said implant being of a porous, non-porous, or gelatinous material, including membranes, such as sialastic membranes, or fibers.

The invention also provides for pharmaceutical compositions comprising NT-3 proteins, peptide fragments, or derivatives administered via liposomes, microparticles, or microcapsules. In various embodiments of the invention, it may be useful to use such compositions to achieve sustained release of NT-3 and NT-3-related products.

It is envisioned that it may be possible to introduce cells actively producing NT-3, NT-3 related substances, NT-3 antagonists, or anti-NT-3 antibodies into areas in need of increased or decreased concentrations of NT-3.

6. EXAMPLE: THE CLONING AND CHARACTERIZATION OF THE MOUSE NEUROTROPHIN-3 GENE

6.1. Materials and Methods

6.1.1. Polymerase Chain Reaction

Two oligonucleotide primers were synthesized on the basis of 2 amino acid sequences conserved in BDNF and all known NGFs (Leibrock et al. 1989, Nature 341:149–152). The sequence of the sense (or 5') primer was GGGGATC-CGC GGI TGY MGI GGI ATH GA (primer 1, IUPAC nomenclature, I=inosine), and includes BamHI and SacII sites, and that of the antisense (or 3') primer TCGAAT-TCTAG AT ICK IAT RAA ICK CCA, and includes EcoRI and XbaI sites (primer 2). PCR (Saiki et al., 1985, Science 230: 1350–1354) was performed with 1 µg of mouse genomic DNA using a Perkin-Elmer Cetus thermal cycler and Taq polymerase (Gene Amp™). After 4 cycles with an annealing temperature of 45° C., the remaining 36 cycles were performed with annealings at 49° C. The resulting amplified DNA products corresponding to the expected size (137 base pairs) were eluted from an acrylamide gel, reamplified and digested with HindIII and ApaI, the former cleaving mouse NGF, the latter mouse BDNF. The uncleaved DNA was eluted and asymmetrically amplified (Innis et al, 1988, Proc. Natl. Acad. Sci. U.S.A. 85:9436–9440) and sequenced (Sanger et al., 1979, Proc. Natl. Acad. Sci. U.S.A. 72:3918–3921) using primers 1 and 2. Based on the sequence thus obtained, 2 additional sense primers were synthesized, corresponding to nucleotide 808–822 (primer 3) and 824–844 (primer 4) to which SalI and PstI sites were added. RNA was extracted from adult mouse brain, liver and muscle (Okayama et al., 1987, Meth. Enzymology 154:3–28) and reverse transcribed using antisense (5') primer CGGATCCGAATTCTGCAG(T)$_{12}$V (primer 5), designed to match 3' poly(A) tails, and containing cloning sites for BamHI, EcoRI and PstI (Leibrock et al., 1989, Nature 341:149–152). These cDNAs were first PCR-amplified using primers 3 and 5, and re-amplified using primers 4 and 5. A Southern blot analysis was performed with the products resulting from this last reaction and hybridized with a $^{32}$P-end-labeled oligonucleotide corresponding to nucleotides 879–893. The DNA fragments thus identified were cloned into a Bluescript® SK+ vector (Stratagene) and the longest insert obtained (460 base pairs) was used to screen an EMBL3 mouse genomic library (Clontech). Two positive clones were found, and the DNA of one clone digested with various restriction enzymes. The restriction fragments were probed with the 460 base pair insert: a 770 base pair HindIII, and a 4000 base pair PstI fragment were subcloned in Bluescript® SK+. The full HindIII sequence, 3' and 5' extended using the Pst1 fragment is shown.

6.1.2. Northern Blotting

Total RNA was extracted from adult female tissues (Okayama et al, 1987, Meth. Enzym. 154:3–28), and eledtrophoresed on 1.3% formaldehyde-containing agarose gels (Hehrach et al, 1977, Biochem. 16:4743–4751). The RNA was transferred to nylon membranes (Hybond-N, Amersham) and hybridized overnight at 42° C. in 1 ml 200 mM sodium phosphate (pH 7.2), containing 40% formamide, 5× Denhardt's solution and 200 μg.ml$^{-1}$ denatured salmon sperm DNA. The probe used was a $^{32}$P-labelled, random-primed double-stranded probe (Feinberg et al, 1979, Anal. Biochem. 137:266–267), corresponding to nucleotides 319–1093 (FIG. 2). The specific activity was 1.3×10$^8$ cpm×μg$^{-1}$, and 10$^7$ were added to the hybridization buffer. Washing was for 60 min at 60° C. in 0.1×SSC containing 0.5% SDS. Filters were exposed for 5 days at −70° C. with intensifying screens.

6.1.3. Expression of Neurotrophin-3

Oligonucleotide primers were synthesized corresponding to the first 19 nucleotides (plus an EcoRI site) and last 19 nucleotides (plus a BamHI site) of the open reading frame depicted in FIG. 2. After PCR amplification using as template the PstI genomic fragment described (FIG. 2), the resulting product was cloned into the EcoRI-BamHI site of the expression vector, pCMV (Anderson et al., 1989, J. Biol. Chem. 264:8222–8229). The nucleotide sequence of the NT-3 insert in pCMV was determined. COS-1 cells were transfected using the calcium phosphate method (Chen and Okayawa, 1987, Mol. Cell Biol. 7:2745–2752) and the medium collected as previously described (Leibrock et al., 1989, Nature 341:149–152). The control media used were obtained after treatment of the COS-1 cells with calcium phosphate, or with a pCMV/NT-3 construct where the stop codon of NT-3 had been deleted. Both media were devoid of biological activity at a dilution of 1:50. Nodose ganglia were dissociated, and the neurons cultured in 24-well plates (Lindsay et al, 1985, Dev. Biol. 112:319–328), and BDNF was purified from pig brain (Hofer and Barde, 1988, Nature 331:261–262).

6.2. Results and Discussion

A major problem in the characterization of neurotrophic factors is their extremely low abundance. Both NGF and BDNF were characterized using protein purification techniques based on biological assays to monitor their activity (Cohen et al, 1960 Proc. Natl. Acad. Sci. U.S.A. 46:302–311; Barde et al., 1982, EMBO J. 1:549–553). This approach was possible with NGF because of the extraordinary abundance of this protein in the adult male mouse submandibular gland, and with BDNF ultimately because of the virtually unlimited availability of porcine brain tissue. The sequence identities detected in NGF and BDNF suggested that a different strategy could be used to characterize other members of what has been determined to be a gene family (Leibrock et al., 1989 Nature 341:149–152). A detailed comparison of the mouse NGF and BDNF amino acid (a.a.) sequences revealed 2 stretches of 6 a.a. (underlined in FIG. 2) that seemed particularly suited for an approach using oligonucleotide primers in a polymerase chain reaction (PCR) (Saiki et al., 1985, Science 230:1350–1354). A mouse genomic template was used because in the NGF and BDNF genes no introns interrupt the exon coding for the biologically active proteins. This approach resulted in the expected amplification of NGF and BDNF sequences, that were subsequently digested using appropriate restriction enzymes. A DNA fragment left intact was sequenced, and the sequence found to correspond neither to BDNF nor to NGF. Two specific sense (or 5') primers were synthesized for further PCRs using as templates complementary DNA prepared by reverse transcription of RNA extracted from mouse brain, muscle and liver, and a 3'primer designed to match poly A sequences (FIG. 2). These 3 tissues gave amplified products of similar sizes that were cloned and used to screen a mouse genomic library. One of the genomic clones thus found was sequenced (FIG. 2). An open reading frame predicts a protein of 258 a.a. (starting with the first methionine found after 3 in frame stop codons) that we name neurotrophin-3 (NT-3). In every respect, the overall structure of the predicted protein resembles that established for NGF and BDNF: a putative signal sequence of 18 a.a. (showing 5 and 9 a.a. identities with BDNF and NGF respectively) is followed by a pro-sequence of 121 a.a. Such pro-sequences, presumably involved in the folding and correct formation of the disulfide bridges of these proteins (Edwards et al., J. Biol. Chem. 263:6810–6815), have also been found in mouse NGF (103 a.a.) and mouse BDNF (112 a.a.). A single potential N-glycosylation site is located 9 a. a. (as compared with 8 in BDNF and NGF) before what we propose to be the cleavage site, characterized by a cluster of basic residues, giving rise to mature NT-3 (FIG. 2, arrow). Mature NT-3 is predicted to consist of 119 a.a. (relative molecular mass 13,625 and pI 9.3). The comparison between mature mouse NGF, BDNF and NT-3 reveals 54 a.a. identities (FIG. 2). All 6 cysteine residues, known in NGF and BDNF to be involved in the formation of disulfide bridges (Leibrock et al., 1989, Nature 341:149–152; Angeletti, 1973, Biochemistry 12:100–115), are amongst the conserved residues (FIG. 3, arrows). Remarkably, the addition of the NT-3 sequence to those of NGF and BDNF reveals that only 7 a.a. identities are lost (61 a.a. identities are found when mouse NGF and BDNF are compared). Thus, almost 50% of the primary structure is conserved, and is likely to be required for the formation of a basic 3-dimensional shape common to all three proteins. In addition, the comparison of the 3 sequences reveals 4 variable domains, each 7 to 11 a.a. in length (numbered V1 to V4 in FIG. 3), and presumably involved in the neuronal specificity exerted by these proteins.

Figure 4B:
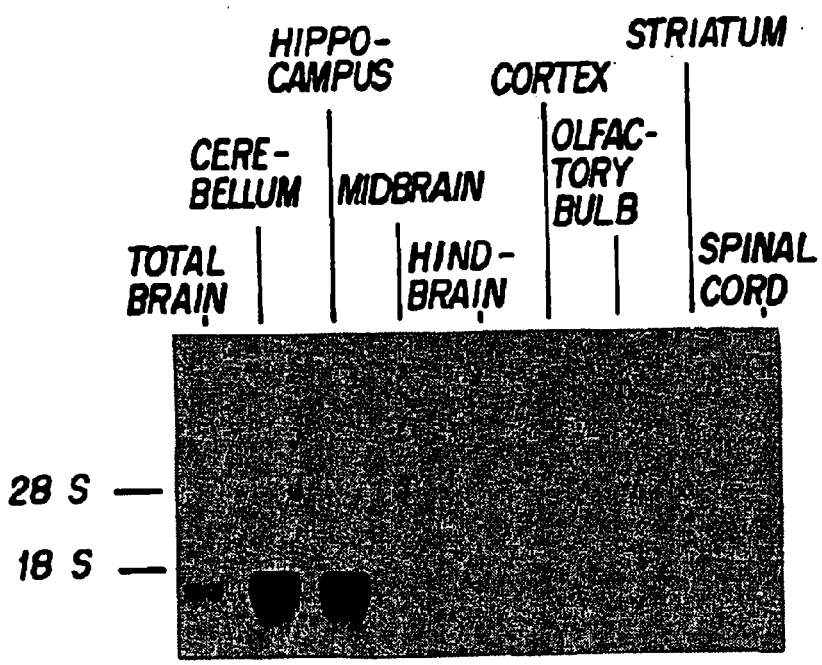

To study the expression of the NT-3 gene, RNA was extracted from a variety of mouse tissues and analyzed with an NT-3 specific probe (FIG. 4). A single band of about 1.4 kilobases was found in all tissues examined (FIG. 4A). However, the level of expression of this mRNA varies considerably. In brain (FIG. 4B), marked regional differences have been found, the highest mRNA levels being observed in cerebellum and hippocampus (FIG. 4B). These results demonstrate that the NT-3 mRNA distribution in adult mouse tissue is very different from that of BDNF and NGF mRNA. Indeed, BDNF mRNA is found predominantly in the brain, and NGF mRNA is hardly detectable in tissues such as liver or skeletal muscle (Heumann et al., 1984, EMBO J. 3:3183–3189). However, it is intriguing to note that the hippocampus, known to express NGF mRNA (Korsching et al., 1985, EMBO J. 4:1389:1393), also expresses BDNF and NT-3 mRNA, and in much larger amounts than in most other brain regions (FIG. 4B).

In order to test if NT-3 is a biologically active and secreted protein, the entire protein coding sequence was cloned into an expression vector (pCMV) used to transfect (monkey kidney) COS cells (FIG. 5). Given the fact that the NT-3 mRNA is found in peripheral tissues, we cultured a variety of embryonic chick neurones known to project to these tissues, and to require trophic factors for survival. Motorneurons, purified from the spinal cord of 6-day old embryos (E6) (Dohrmann et al., 1986, Dev. Biol. 118:209–221), ciliary neurons (E8) and dissociated sympathetic neurons (E11) were not observed to survive in the presence of NT-3. However, sensory neurons isolated from E8 primary sensory ganglia were found to respond. As shown here (FIG. 5), NT-3 supports the survival of about 30% of the neurons isolated from the nodose ganglion. Furthermore, this effect is additive to that of BDNF, synthesized in the central projection fields and known to act on a subpopulation of the nodose neurons (Lindsay et al., 1985 Dev. Biol. 112:319–328), and both factors combined rescue most neurones (90%) (FIG. 5). It is important to note that the NT-3 mRNA is found in the visceral targets of this ganglion, including heart, gut, liver and lung (FIG. 4A). Populations of NT-3 responsive sensory neurons were also found in E8 dissociated dorsal root and trigeminal ganglia and in explants of E8 sympathetic ganglia. It thus appears that NT-3 is a hitherto uncharacterized biological activity present in several peripheral tissues, including liver (Lindsay and Tarbit, 1979, Neuro Sci. Lett. 12:195–200) and skeletal muscle (Davies, 1986, Dev. Biol. 115:56–67, and known to support the survival of visceral and proprioceptive sensory neurons not responding to NGF (for review, see Davies, 1987, Development 101:185–208).

Taken together, these findings indicate that NT-3 is an neurotrophic factor related both in structure and function to NGF and BDNF, the first 2 neurotrophins. We propose the name neurotrophin (NT) to refer to this class of protein, and in analogy with the interleukins, to number them in the order of their discovery.

7. EXAMPLE: THE CLONING AND CHARACTERIZATION OF THE RAT NEUROTROPHIN-3 GENE

The homology between NGF and BDNF was utilized in designing a cloning strategy to search for additional members of this gene family. We report the cloning of a gene encoding a third member of the BDNF/NGF family, which we have designated neurotrophin-3 (NT-3). This novel factor exhibits distinct biological activity and spatio-temporal expression when compared to NGF and BDNF.

7.1. Materials and Methods

7.1.1. Polymerase Chain Reactions

Degenerate oligonucleotides corresponding to segments of four protein sequences highly conserved between NGF and BDNF were synthesized; the protein sequences (which can be found within the NGF/BDNF sequences presented in FIG. 7D) were (1) Gly-Glu-(Tyr/Phe)-Ser-Val-Cys-Asp-Ser, (2) Lys-Gln-Tyr-Phe-(Tyr/Phe)-Glu-Thr-Lys-Cys, (3) Gly-Cys-Arg-Ile-Asp, and (4) Trp-Arg-Phe-Ile-Arg-Ile-Asp-Thr-(Ser/Ala)-Cys-Val-Cys. A series of degenerate sense and anti-sense oligonucleotides (containing a degenerate portion 15–26 nucleotides long, corresponding to 5–9 amino acids of the indicated protein sequences in either the sense or anti-sense direction, as well as a non-degenerate "tail" encoding restriction enzyme recognition sites) were used in PCR reactions. Amplification reactions between pairs of upstream sense and downstream anti-sense primers were carried out according to the conditions recommended by Perkin-Elmer/Cetus, except that the annealing temperature, $Mg^{++}$ concentration and extension time were varied to determine optimal conditions for each primer pair. The exact sequence of the 1B sense primer (encoding a portion of the protein sequence "1" above) was 5'-GACTCGAGTCGACATCG-GTN-TGY-GAY-WSN-RTN-WS-3' and the 2C anti-sense primer (corresponding to the anti-sense codons of a portion of protein sequence "2" above) was 5'-CCAAGCTTCTAGAATTC-CA-YTT-NGT-YTC-RWA-RAA-RTA-YTG-3' (abbreviations for nucleotides as in IUPAC code). Subsequent sequence analysis showed that the 1B oligonucleotide had a two nucleotide mismatch with the NT-3 sequence, whereas the 2C oligonucleotide had a one nucleotide mismatch with the NT-3 sequence. Radiolabelling by PCR was done according to the recommended gene amplification reaction by Perkin-Elmer/Cetus, with the following modifications: 1 to 10 ng of DNA template in low melting point agarose was added to a reaction mix containing unlabelled DATP, dGTP, and DTTP at a final concentration of 50 $\mu$M; 50 $\mu$Ci $\alpha^{32}$P-dCTP (3000 Ci/mmole) was added per 50 $\mu$l reaction and the reaction was subjected to seven amplification cycles. Amplification primers were identical to the degenerate primers used in the original PCR reaction.

7.1.2. Southern Blot of Rat Genomic DNA Using NT-3 Probe

R1B/2C PCR product was obtained by amplification from rat genomic DNA template using degenerate 1B and 2C primers as described above in Section 7.1.1. PCR product derived using degenerate 1B and 2C primers (designated R1B/2C) detects a novel gene, NT-3, as well as the NGF and BDNF genes in rat genomic DNA. DNA was prepared from the liver of Fischer rats (Maniatis et al., 1982, Molecular Cloning: A Laboratory Manual (Cold Spring Harbor Laboratory, Cold Spring Harbor), digested with EcoR1, and 10 $\mu$g were fractionated on a 1% agarose gel. The DNA was transferred to nitrocellulose using 10×SSC (Maniatis et al., 1982, Molecular Cloning: A Laboratory Manual (Cold Spring Harbor Laboratory, Cold Spring Harbor), hybridized (Mahmoudi and Lin, 1989, Biotechniques 7:331–3) to the $^{32}$P-labelled R1B/2C PCR product at 60° C., and washed in 2×SSC/0.1% SDS at 65° C. NT-3, NGF and BDNF bands as indicated; position of NGF and BDNF bands previously determined using specific probes. Sizes indicated in kilobases (kb) on left.

7.1.3. Expression of Neurotrophin-3

The rat NT-3 expression construct was made by using PCR to amplify the coding region of the presumed short precursor of NT-3 from a plasmid containing the 3.2 kb Sst1 rat genomic fragment (FIG. 6B) that spans the NT-3 gene;

the oligonucleotides used in the PCR reaction contained synthetic Xho1 recognition sites at their ends, to permit insertion of the amplified coding region into the Xho1 site in the polylinker of the pCDM8 expression vector (Seed, 1987, Nature 329:840–42). The exact oligonucleotides used to amplify the rat NT-3 gene coding region were the upstream sense primer 5'-CGG TAC CCT CGA GCC ACC ATG TCC ATC TTG TTT TAT GTG-3' (the underlined ATG corresponds to the "B" start site initiation codon, with sequence downstream of the ATG matching the NT-3 sequence exactly; upstream of the ATG the primer contains a synthetic Xho1 site), and the downstream anti-sense primer 5'CGG TAC CCT CGA GAT GCC AAT TCA TGT TCT TCC G-3' (the underlined triplet is complementary to the termination codon for the NT-3 gene; this triplet is flanked by exact anti-sense NT-3 sequence, and there is an Xho1 site at the 5' end of this primer). The resulting expression plasmid for rat NT-3 was designated pC8-rN3(P1). Similar strategies were previously used to insert the coding regions of rat NGF and BDNF into the Xho1 site of the same pCDM8 vector. The NT-3, NGF and BDNF expression constructs were transfected, as described in Okayama and Berg (1982, Mol. Cell Biol. 5:1136–42) into COS-M5 cells seeded at $5 \times 10^5$ cells per 60 mm plate and cultured in 2.5 ml of Dulbecco's Modified Eagle's Medium containing high glucose (4500 mg/ml) and 10% fetal bovine serum; supernatants were harvested 72 hours after transfection.

7.2. Results

7.2.1. Cloning of the Neurotrophin-3 Gene

Amplification products of the expected sizes (as predicted from the NGF and BDNF sequences) were obtained using the different pairs of degenerate oligonucleotides. These products were first subjected to restriction enzyme analysis to determine the relative content of NGF, BDNF or novel sequences. In all cases, restriction fragments corresponding only to NGF and BONF sequences were detectable by staining with ethidium bromide. However, use of the same PCR products as hybridization probes on Southern blots of rat genomic DNA revealed that one product (designated R1B/2C-see FIG. 6A) identified a novel genomic DNA sequence, in addition to NGF and BDNF (FIG. 6A); thus, screening of PCR products by Southern blotting allowed for identification of rare amplified sequences that were undetectable by other means. The R1B/2C probe also detected novel sequences in the genomic DNA of evolutionarily divergent species (including human, mouse, chicken and *Xenopus*), suggesting that this probe identifies a functional gene.

Figure 6B:
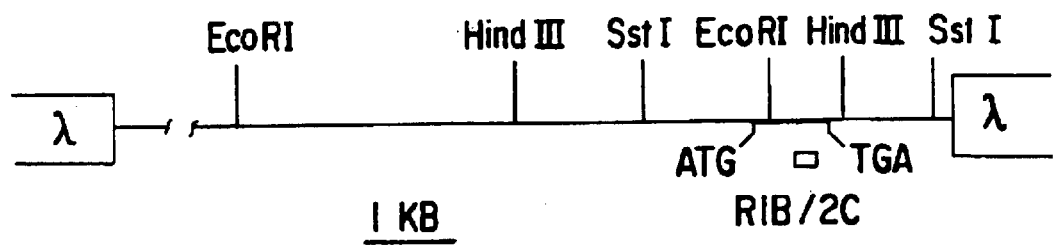

In order to isolate this gene, the R1B/2C probe, as well as probes specific for NGF and BDNF, were used to screen (Maniatis et al., 1982, Molecular Cloning: A Laboratory Manual (Cold Spring Harbor Laboratory, Cold Spring Harbor)) a rat genomic DNA library (purchased from Clontech Laboratories, Inc., Palo Alto, Calif.) prepared from Sprague-Dawley rat DNA (partially digested with Sau3A restriction endonuclease and cloned in the EMBL3/SP6/T7 bacteriophage vector). Two independent bacteriophage clones were found that hybridized to R1B/2C probe, but not to the other two probes. Restriction map analyses of the rat genomic inserts in these clones demonstrated that they correspond to the same gene (FIG. 6B). The bacteriophage clone with the longest insert was designated ϕrN3(G1). Sequence analysis proved that the gene identified by R1B/2C encodes a new member of the NGF/BDNF family (see FIG. 7), which we have named neurotrophin-3.

7.2.2. Sequence Analysis of Mature Neurotrophin-3

DNA sequencing was carried out by the dideoxynucleotide chain termination method (Sanger et al., 1977, Proc. Natl. Acad. Sci. U.S.A. 74:5463–7), using the SEQUENASE Version 2.0 kit supplied by United States Biochemical Corporation, using protocols recommended by the manufacturer.

NGF has two distinct precursor forms, termed the "long" (initiating at start site "A") and short (initiating at start side ABU) precursors, that differ by the length of their N-terminal sequences (Darling et al., 1987, Cold Spring Harb. Symp. Quant. Biol. 1:427–34; Selby et al., 1987, Mol. Cell Biol. 7:3057–64; Edwards et al., 1988, Mol. Cell Biol. 8:2456–64). Both the long and short precursors can be proteolytically cleaved to yield the mature form of NGF, which essentially constitutes the carboxy-terminal 120 amino acids of each precursor. BDNF may also have similar long and short precursor forms.

Sequencing of the NGF gene from several species has revealed that most of this additional N-terminal sequence is found on separate exons, except for four codons (Val-His-Ser-Val) that are included at the 5' end of the axon that encodes the entire short (start site "B") precursor. We have previously demonstrated that two of these four codons (Val-X-X-Val), as well as the RNA splice acceptor site that precedes them, are conserved just upstream to a conserved "B" start site in BDNF genes isolated from several species; this finding led us to propose that both long and short precursor forms of BDNF exist. There is conservation of the Val-X-X-Val codons, as well as the splice acceptor site, in the rat NT-3 gene; this splice acceptor site and the proposed intron boundary are indicated in FIG. 7A. These sequence considerations lead us to predict the existence of upstream coding exons for the NT-3 gene, which would encode a long precursor form. The finding of the conserved sequence upstream of the putative NT-3 "A" start site further reinforces our prediction of the existence of a long BDNF precursor and suggests an important, evolutionarily conserved role of this long precursor for all the members of the NGF family. The predicted N-terminus of mature NT-3 follows a canonical protease cleavage sequence (Arg-Arg-Lys-Arg), very similar to those seen in NGF and BDNF (FIGS. 7A,C). In some species, the two C-terminal amino acids of NGF are also proteolytically removed. Unlike NGF, rat NT-3 does not have an obvious potential cleavage site at its C-terminus (FIGS. 7A,C), and we infer that, as with BDNF in all species examined to date, there is no proteolytic modification at the C-terminus of NT-3.

Based on these considerations, the predicted size of the mature NT-3 polypeptide is 119 amino acids, with a computed pI of about 9.5. Thus, in size and charge, NT-3 closely resembles NGF and BDNF. The seven N-terminal amino acids of mature NT-3 differ completely from NGF and BDNF. Starting from amino acid eight of mature NT-3, optimal alignment required a single gap of two amino acids relative to BDNF and a single insertion of one amino acid relative to NGF (FIG. 7D). The mature rat NT-3 displays 57% amino acid homology with rat NGF, and 58% amino acid homology with rat BDNF; 57 of the 120 residues (48%) are shared by all three proteins (FIG. 2D). The six cysteine residues found in NGF and BDNF are absolutely conserved in NT-3, and regions of greatest homology between the three proteins are mainly clustered around these cysteine residues.

7.2.3. Analysis of Neurotrophin-3 Precursors

Just upstream to the presumptive cleavage site that releases mature NT-3, there is a universal glycosylation acceptor site (Asn-X-Thr/Ser, see FIGS. 7A,C) which also has been found at the same position in NGF and BDNF (Ullrich et al., 1983, Nature 303:821–5; Leibrock et al., 1989, Nature 341:149–52). Whether this glycosylation site plays a role in processing of the NT-3, NGF or BDNF precursors remains unknown.

Further comparison of the NT-3 sequence with the NGF and BDNF precursors reveals two regions of amino acid homology upstream of the mature NT-3 sequence (regions I and II in FIGS. 7B,C). The region I homology leads us to predict the existence for rat NT-3 of a "B" start site (defined for NGF above), which would yield a short precursor of 258 amino acids, similar in size to the short precursors for NGF (241 amino acids) and BDNF (249 amino acids); the apparent methionine initiation codon, secretory signal sequence and signal sequence cleavage site for the short precursors of all three factors are conserved (FIG. 7C). Because the region 1 homology extends upstream of the "B" start site, we also predict the existence of a long precursor for NT-3 which would initiate from an "A" start site (see FIGS. 7A,B,C). As has been seen with NGF (Ullrich et al., 1983, Nature 303:821–5; Selby et al., 1987, Mol. Cell Biol. 7:3057–64), and proposed for BDNF, such a start site presumably would be encoded on additional exons upstream to the single exon which encodes the entire short precursor.

In addition to the region I and II amino acid homologies, comparisons of hydrophilicity plots for NT-3, NGF and BDNF reveal a similarity of structure in the precursors, upstream of the mature products.

7.2.4. Neurotrophin-3 Possesses Neurotrophic Activity

The striking homology among NT-3, NGF and BDNF strongly suggested that NT-3 might possess neurotrophic activity. NGF and BDNF can each promote the survival of selected populations of peripheral and central nervous system neurons in vivo and in vitro (reviewed in Whittemore and Seiger, 1987, Brain Res. Rev. 12:439–64; Lindsay, 1988, in "The Making of the Nervous System," pp. 149–65; Davies, 1988, Trends Genet. 4:139–43). For example, the administration of either factor to developing avian embryos prevents naturally occurring neuronal death in specific peripheral ganglia (e.g. Hoffer and Barde, 1988, Nature 331:261–2). When added to explanted ganglia, NGF and BDNF induce neurite outgrowth (Davies et al., 1986, J. Neurosci. 6:1897–904); when added to cultures of dissociated ganglionic neurons, these factors promote neuronal survival and differentiation (Lindsay et al., 1985, Dev. Biol. 112:319–28). Such in vitro assays, utilizing several types of chick peripheral ganglia, have been used to distinguish between the neurotrophic activities of NGF and BDNF. Whereas both factors act on populations of sensory neurons found in the neural crest-derived dorsal root ganglia (DRG), only BDNF supports the sensory neurons of the neural placode-derived nodose ganglion (NG) (Lindsay et al., 1985, Dev. Biol. 112:319–28). In contrast, NGF, but not BDNF, can support the survival and growth of neurons of the paravertebral chain sympathetic ganglia (SG)(Barde et al., 1982, EMBO J. 1:549–53).

In order to assess the potential biological activity of NT-3, we inserted the rat NT-3 gene into a vector, pCDM8 (Seed, 1987, Nature 329:840–42), which was previously used to transiently express BDNF and NGF in mammalian cells. This construct was designed to express the short precursor form of NT-3; expression of the short precursor forms of NGF and BDNF has yielded biologically active material (Edwards et al., 1988, Mol. Cell Biol. 8:2456–64; Leibrock et al., 1989, Nature 341:149–52). The NT-3, NGF and BDNF constructs were transfected into COS cells; culture supernatants were harvested and first assayed at varying concentrations for their ability to induce neurite outgrowth from DRG explants. As expected, NGF and BDNF promoted neurite outgrowth in this assay (FIG. 8). In the first demonstration that the NT-3 gene actually encodes a neurotrophic activity, the product of this gene induced profuse neurite outgrowth from the DRG explants (FIG. 8).

To establish that NT-3 acts directly on neurons, we assayed this factor in highly enriched cultures of dissociated DRG neurons (FIG. 9). In the virtual absence of Schwann cells and fibroblasts, NT-3 promoted survival and neurite outgrowth of approximately 60% of these DRG neurons. Given that NGF and BDNF together support virtually 100% of DRG neurons in culture (Lindsay et al., 1985, Dev. Biol. 112:319–28), it must be assumed that NT-3 promotes survival of cells that are also responsive to at least one of the other two factors.

7.2.5. Neurotrophic Activity of NT-3 is Distinct from NGF and BDNF

To further explore the neuronal specificity of NT-3, we assayed the factor on NG and SG explants. As expected, control experiments verified that NGF induced neurite outgrowth from SG but not NG explants from E8 chick embryos, whereas BDNF induced neurite outgrowth from NG but not SG explants. Interestingly, NT-3 promoted neurite outgrowth from both NG and SG explants (FIG. 8), suggesting a broader specificity than either NGF or BDNF. However, NT-3, like NGF and BDNF, failed to promote survival or promote neurite outgrowth from explants or dissociated, neuron-enriched cultures of the chick ciliary ganglion. As has been previously shown, the parasympathetic neurons that comprise the ganglion did respond to rat CNTF, a neurotrophic factor unrelated to the NGF/BDNF/NT-3 family ((Manthorpe et al., 1986, Brain Res 367:282–6); Stockli et al., 1989, Nature 342:21–28). No response was seen in any of these assays using supernatants from COS cells transfected with control vectors (FIG. 8).

The results of a representative experiment measuring the responses of explanted embryonic day 8 (E8) chick dorsal root ganglia (DRG), nodose ganglia (NG), and paravertebral sympathetic ganglia (SG) to increasing doses of NT-3 are shown in Table IV. Ganglia were cultured for the times indicated as explants in 1 ml of collagen gel, as described in Lindsay and Rohrer, 1985, Dev. Biol. 112:30–48). Fiber outgrowth was scored on a scale of 0 to 5, where 5 is the maximum fiber outgrowth observed on dorsal root ganglia in response to a saturating dose of nerve growth factor (NGF) (1–10 ng/ml). Rat NT-3 was provided as conditioned medium from COS-M5 cells transfected with plasmid pC8-rN3(P1), as described above. Conditioned medium from mock-transfected COS-M5 cells was used as a control. At all doses tested, over a 50-fold range, NT-3 promoted detectable fiber outgrowth from all three types of explanted ganglia, although at low doses the responses were weaker on sympathetic ganglia. The maximum fiber outgrowth response of dorsal root ganglia to NT-3 was comparable to that seen for NGF or BDNF. The maximum response of nodose ganglia to NT-3 was greater than the maximal response seen to BDNF. Nodose ganglia do not show a fiber outgrowth response to NGF). The maximum response of sympathetic ganglia to NT-3 was less than the maximal response of these ganglia to NGF, and was observed at higher concentrations than were required for maximal responses to NT-3 in dorsal root or nodose ganglia cultures.

TABLE IV

Recombinant rat NT-3 promotes fiber outgrowth from explants of:

DRG = E8 chick embryo dorsal root ganglia
NG = E8 chick embryo nodose ganglia
SC = E8 chick embryo paravertebral sympathetic chain ganglia

| | | | Fiber Outgrowth Score | | |
|---|---|---|---|---|---|
| | | | DRG (24 h) | NG (24 h) | SC (24 h) |
| Control | 500 µl | mock-transfected COS cell supernatant | 0–0.5 | 0 | 0 |
| NT-3 | 10 µl | COS cell supernatant | 2–3 | 2–3 | 0–0.5 |
| NT-3 | 50 µl | COS cell supernatant | 3–4 | 4–5 | 0–0.5 |
| NT-3 | 200 µl | COS cell supernatant | 5* | 2–3* | 0–1 |
| NT-3 | 500 µl | COS cell supernatant | 5* | 0–2* | 1–2 |

The results are the range of fiber outgrowth scores from 4 to 6 ganglia in each case.
*At supersaturating levels of NT-3, fiber outgrowth is reduced as determined by fiber length on DRG explants and by the number of fibers on NG explants.

The results are the range of fiber outgrowth scores from 4 to 6 ganglia in each case.

At supersaturating levels of NT-3, fiber outgrowth is reduced as determined by fiber length on DRG explants and by the number of fibers on NG explants.

7.2.6. Rat Neurotrophin-3 is Active on Mammalian Neurons

In order to determine whether rat NT-3 displays activity on mammalian neurons, the explant assay was repeated using dorsal root ganglia dissected from day 14 rat embryos (Table V). Purified NGF was used as a control. The E14 rat dorsal root ganglia explants (four ganglia per 1 ml culture) were cultured for 24 hours, essentially as described for chick ganglia (FIG. 8, Table IV), with no added neurotrophic factor (control), with mouse submaxillary gland nerve growth factor (NGF), or with recombinant rat NT-3 (conditioned medium from COS-M5 cells transfected with plasmid pC8-rN3(P1), as described above). Each ganglion was scored for fiber outgrowth, as described (see Table IV). The results show that, like NGF, NT-3 is highly active in promoting fiber outgrowth from the rat dorsal root ganglia explants.

TABLE V

NT-3 promotes fiber outgrowth from explants of rat embryo dorsal root ganglia.

| | Fiber Outgrowth Score E14 Rat DRG |
|---|---|
| Control | 0, 0, 0, 0 |
| NGF (mouse, 5 ng/ml) | 4, 4, 4, 3 |
| NT-3: 20 µl rat NT-3 COS cell supernatant | 3, 3, 3, 4 |

Fiber outgrowth scores (scale of 0 to 5) are given for each of four individual ganglia per culture.

While the DRG, NG and SG explants each responded to at least two of the three related neurotrophic factors, the maximal response exhibited by a given ganglion depended on the factor used. In the case of DRG, the response to saturating levels of NGF, BDNF and NT-3 was relatively equivalent. However, with NG, the maximal response to NT-3 was greater than to BDNF, while with SG, the maximal response to NT-3 was substantially lower and somewhat delayed compared to NGF.

7.2.7. Exploring the Sites of Neurotrophin-3 Synthesis

It has been established that during development neuronal survival depends on target-derived neurotrophic molecules. Continued survival, even in the adult, may require the persistence of a neurotrophic influence (Thoenen et al., 1987, Ciba Found. Symp. 126:82–95). In other cases survival of mature neurons may no longer depend on a neurotrophic factor; nevertheless such factors have been shown to profoundly affect the differentiated phenotype of neurons (Lindsay and Harmar, 1989, Nature 337:362–4). Determining the sites of synthesis of a neurotrophic molecule may therefore help to elucidate its physiological roles.

To explore the sites of NT-3 synthesis and to compare NT-3 expression with that of NGF and BDNF, to triplicate Northern blots of RNA samples prepared from a variety of adult rat tissues were hybridized to probes specific for each of these genes (FIG. 10). As previously demonstrated (Heumann et al., 1984, EMBO J. 3:3183–9; Shelton and Reichardt, 1984, Proc. Natl. Acad. Sci. U.S.A. 81:7951–5), expression of NGF mRNA was highest in brain, heart, and spleen; at least trace levels were detectable in all other tissues examined. BDNF displayed a more restricted pattern of expression; highest levels were found in brain (Leibrock et al., 1989, Nature 341:149–52), and significant levels were seen in heart, lung, and muscle. As with NGF, the NT-3 transcript (1.4 kb) was detectable in all adult tissues surveyed. However, in all peripheral tissues surveyed the level of expression of NT-3 mRNA was at least comparable to that seen in the adult brain, and in some cases (e.g. kidney, spleen) was substantially higher.

We also compared the relative abundance of the NGF, BDNF, and NT-3 transcripts in the brains of newborn and adult mice. In contrast to both NGF and BDNF, the level of NT-3 mRNA in newborn brain was higher than in adult brain (FIG. 8). A more detailed analysis has revealed that NT-3 mRNA levels in the central nervous system are dramatically higher during fetal development and then decrease to adult levels.

7.3. Discussion

Structural comparisons among NGF, BDNF, and the newest member of this gene family, NT-3, highlight several conserved regions, and lead to the suggestion that the functional differences among these proteins are determined by sequences lying outside of these conserved regions. The predicted existence of long and short precursor forms of all three proteins raises intriguing questions about the relevance of both precursor forms in vivo. The long forms may be processed more efficiently than the short forms. Nevertheless, vectors expressing the short precursor forms of these factors yield biologically active material in COS cells.

Our finding that these three neurotrophic factors display distinct stage-specific and tissue-specific patterns of expression supports the notion that neural development depends on the temporally and spatially distinct expression of discrete neurotrophic activities. The developmental profile of NT-3 expression suggests that this factor may play a particularly important role early in the development of the nervous system. Our initial characterization of NT-3 neurotrophic activity in vitro, coupled with the generalized prevalence of NT-3 mRNA in both the adult brain and adult peripheral tissues, further suggest that NT-3 may have a widespread influence on neuronal function and/or survival in the adult. The more global expression of NT-3 also raises the possibility that this factor acts on cells outside of the nervous system, as has been proposed for NGF (Otten et al., 1989, Proc. Natl. Acad. Sci. U.S.A. 86:10059–10063).

Although it has not yet been clearly demonstrated that neurons can be simultaneously responsive to more than one neurotrophic factor, evidence suggests that NGF and BDNF may act on overlapping neuronal populations. For example, administration of either NGF or BDNF can rescue the vast majority of DRG neurons that would otherwise die during normal avian development (Hofer and Barde, 1988, Nature 331:261–2). Our observations on the effects of NT-3 on chick peripheral ganglia strongly support the intriguing possibility that individual neurons can respond to multiple, related favors. If this is the case, both the mediation and physiological relevance of simultaneous responsiveness would raise fascinating questions. For example, components of the receptors and/or signal transduction mechanisms for the three structurally related neurotrophic factors may be shared. In principle, simultaneously responsive neurons could have multiple receptors, each specific for a given neurotrophic factor, or a single receptor which can mediate a response to multiple neurotrophic factors. In vivo, these various factors may be simultaneously presented to all responsive neurons. More likely, there are spatio-temporal differences in the relative availability of individual factors (e.g. Davies et al., 1987, Nature 326:353–8). It may even be possible that different factors are available to different sites of the same neuron (e.g. a sensory neuron may receive distinct factors from its peripheral and central terminals) (Kalcheim et al., 1987, Le Douarin, EMBO J. 6:2871–3). If multiple factors are simultaneously available to some neurons, their actions might be either redundant or complementary.

Elucidating the individual and potentially complementary roles of NGF, BDNF and NT-3 will provide information crucial for understanding normal development and maintenance of the nervous system. Animal studies have suggested that NGF may be of value in the treatment of degenerative neurological conditions (Snider and Johnson, 1989, Ann. Neurol. 26:489–506; Fischer et al., 1987, Nature 329:65–8; Phelps et al., 1989, Neurobiol. Aging 10:205–7). The cloning of a new member of the NGF/BDNF gene family, and its potential interactions with the other members of the family, raise new considerations for the potential therapeutic applications of these proteins in neurodegenerative diseases.

8. Example: The Cloning and Characterization of the Human Neurotrophin-3 Gene

8.1. Results

The preparation of a probe (R1B/2C) used to identify the rat NT-3 gene was performed as described in Example Section 7, supra. As described therein, the probe was prepared by polymerase chain reaction (PCR) from rat genomic-DNA, using degenerate oligonucleotide primers corresponding to two of the "boxes" of amino acid sequence homology shared by NGF and BDNF. The presence within the R1B/2C probe of a population of DNA molecules representing a novel gene was revealed initially by Southern blot hybridization on rat genomic DNA digested with EcoR1 restriction endonuclease; the probe detected a novel DNA fragment, in addition to the expected fragments known to correspond to the NGF and BDNF genes.

When $^{32}$P-labeled R1B/2C was used as a probe to analyze Southern blots of human genomic DNA digested with various restriction endonucleases, as in the case of rat DNA, hybridization was observed to bands corresponding to the NGF and BDNF genes, but also to novel bands. For example, with HindIII restriction endonuclease, a novel (i.e. non-NGF, non-BDNF) band of approximately 1.8 kb was observed; with BamH1 a novel band of approximately 15 kb was observed; and with EcoRI novel bands of 8 and 12 kb were observed (the presence of two bands may have resulted from a polymorphism in EcoRI restriction sites in the human genomic DNA). These data indicated that human DNA contains a gene for NT-3, which is well conserved between rats and humans.

The human NT-3 gene was isolated by screening a genomic library, as described for the isolation of the rat NT-3 gene (see Example Section 7). Briefly, a library consisting of Sau3A partial digestion products of human placental genomic DNA, cloned in the bacteriophage vector λEMBL3/SP6/T7 (purchased from Clontech Laboratories, Inc.) was screened with the R1B/2C probe, and with rat NGF and rat BDNF probes. A human NT-3 clone would be expected to hybridize with R1B/2C, but not with either NGF or BDNF. One such phage clone was identified among approximately $8\times10^5$ plaques screened. This clone, designated ϕhN3(G1), was found to contain a human DNA insert of approximately 16 kb. The clone was restriction mapped by conventional methods, and selected restriction fragments were subcloned into plasmid pBluescriptII (Stratagene) for DNA sequence analysis. The sequence of the human NT-3 gene and the deduced amino acid sequence of its protein product, aligned with the rat NT-3 sequences, are shown in FIG. 11.

8.2. Discussion

The results of sequence analysis show a strikingly high degree of conservation in nucleic acid and amino acid sequence between rat and human NT-3. Within the region encoding the mature polypeptide (119 amino acids), the human and rat genes are approximately 92% homologous in DNA sequence. However, none of the differences in nucleotide sequence between human and rat in this region lead to amino acid substitutions; the deduced amino acid sequences of mature rat and human NT-3 (and mature mouse NT-3, see Section 6, supra) are absolutely identical. This is reminiscent of the high degree of conservation of BDNF, which shows complete identity in the amino acid sequence of the mature polypeptide among rat, mouse, human, and pig. By contrast, the amino acid sequences of mature human NGF and rodent NGF (mouse or rat) differ by approximately 10%. Furthermore, the amino acid sequences of the putative human and rat NT-3 precursors also show remarkably f w differences (underlined in FIG. 11). Immediately upstream of the predicted protease cleavage site that would generate the mature NT-3 polypeptide (Arg-Arg-Lys-Arg), the human sequence lacks one codon (for Pro) that is present in the rat sequence. One block of four amino acids differs between human and rat preproNT-3, and six additional single amino acid substitutions are scattered between that block and the predicted protease cleavage site.

9. Biological Activity of Human NT-3

Because the deduced amino acid sequence of mature human NT-3 is identical to that of mature rat NT-3, it was strongly predicted that the human and rat NT-3 proteins would display indistinguishable biological activities. The neurotrophic activity of human NT-3 was confirmed by inserting the cloned human gene into the plasmid expression vector pCDM8, transfecting the resulting plasmid pC8-hN3 (P1) into COS-M5 cells (as described by Chen and Okayama, 1987, Mol. Cell. Biol. 7:2745–52), and assaying for neurotrophic activity in conditioned medium from the transfected cells. The human NT-3 gene was amplified by PCR from bacteriophage φhN3(G1), and inserted into the plasmid expression vector pCDMB, as described for the rat NT-3 gene (Example 7); the resulting plasmid was designated pC8-hN3(P1). The nucleotide sequence of the entire NT-3 insert was determined and compared with the genomic sequence determined as described above, in order to confirm that no mutations had been introduced during the PCR amplification and cloning procedures. The transfection and assay methods were essentially identical to those used in assessing the biological activity of rat NT-3.

As predicted, human NT-3 was found to possess neurotrophic activity when assayed on explants of embryonic day 9 (E9) chick dorsal root ganglia and nodose ganglia (Table VI). The ganglia were cultured (see FIG. 8, Table IV) for 24 hours in the presence of conditioned medium (supernatants) from mock-transfected COS-M5 cells, or from COS-M5 cells transfected with plasmids (all derived from the pCDM8 expression vector) encoding recombinant human BDNF, or recombinant rat NT-3 [rNT-3; plasmid pC8-rN3(P1)] or recombinant human NT-3 [hNT-3; plasmid pC8-hN3(P1)]. The BDNF plasmid was chosen as a positive control, because BDNF is known to have neurotrophic activity on both dorsal root and nodose ganglia. As shown in Table VI, both rat and human recombinant NT-3, at a modest dose (compare Table IV), displayed approximately the same level of activity as BDNF on dorsal root ganglia, and significantly greater activity than BDNF on nodose ganglia. No difference was observed in the activity of human versus rat NT-3.

TABLE VI

Recombinant human NT-3 produced in COS cells is as active as recombinant rat NT-3 when assayed on chick embryo dorsal root ganglia or nodose ganglia in explant cultures

|  |  |  | Fiber Outgrowth Score | |
| --- | --- | --- | --- | --- |
|  |  |  | DRG | NG |
| Control |  |  | 0, 0, 0, 0, 0.5 | 0, 0 |
| BDNF: | 20 μl | COS supernatant | 3, 3, 3, 3, 3 | 1, 3 |
| Mock: | 20 μl | COS supernatant | 0, 0.5, 0, 0, 0 | 0 |
| human NT-3: | 20 μl | COS supernatant | 3, 2, 4, 3 | 3, 3 |
| rat NT-3: | 20 μl | COS supernatant | 3, 4, 4, 3, 4 | 3, 4 |

Scores are a measure of the fiber outgrowth (scale 0 to 5) seen on 1 to 5 individual ganglia at 24 h in culture. The score for each individual ganglion is shown.

10. Identification of Human NT-3 Gene Product by Metabolic Labeling

The predicted size of the mature NT-3 polypeptide (rat or human) is 119 amino acids, with a molecular weight of 13.6 daltons. In order to determine experimentally the approximate size of the mature human NT-3 polypeptide, cells transfected with a human NT-3-expression plasmid were metabolically labeled and conditioned medium was analyzed for the presence of a novel polypeptide. In the experiment shown in FIG. 12, COS-M5 cells were transfected with the plasmid pC8-hN3(P1) (described above), the cells were labeled with a mixture of ($^{35}$S-methionine and [$^{35}$S]cysteine, growth medium was collected and fractionated by electrophoresis under denaturing conditions on a 15% polyacrylamide gel, proteins were transferred to a membrane filter (essentially as described in Towbin et al., 1979, Proc. Natl. Acad. Sci. U.S.A. 76:4350–4354), and labeled polypeptides were detected by autoradiography. Mock-transfected cells were used as a control (lane labeled "MOCK"). As shown in FIG. 12, the expression plasmid pC8-hN3(P1) directed the synthesis of a single polypeptide, of approximately 14 kDa (labeled NT-3 in the figure), that was not seen in the control. Within the limits of resolution of the technique, this agrees well with the predicted size of mature NT-3.

11. Example: Neutrophin-3 Supports the Survival of Cultured Dopaminergic Neurons of the Embryonic Rat Ventral Mesencephalon Cultures of E14 rat embryo ventral mesencephalon were established as described in U.S. patent application Ser. No. 07/400,591, filed Aug. 0.30, 1989, which is incorporated in its entirety by reference herein. Cultures were seeded at a density of 50,000 cells/cm$^2$ (FIG. 13) or 100,000 cells/cm$^2$ (FIG. 14) and grown in the absence of neurotrophic factor control or in the presence of increasing amounts of COS cell supernatant containing recombinant human neurotrophin-3 (NT-3). After 8 days in culture, cells were fixed and stained with a monoclonal antibody to tyrosine hydroxylase (TH), a marker of dopaminergic neurons. As shown in FIGS. 13 and 14, increasing amounts of NT-3 were found to increase the number of TH positive cells surviving after 8 days, with a maximum of a 2.5-fold increase over control values with a 1:25 dilution of NT-3 COS cell supernatant. Purified nerve growth factor appeared to be without effect, but the effects of NT-3 were similar to those observed for BDNF.

12. Example: NT-3, BDNF and NGF in the Developing Rat Nervous System: Parallel as Well as Reciprocal Patterns of Expression

12.1. Methods

12.1.1. Materials and Dissections

Sprague-Dawley rats, obtained from Harlan Sprague Dawley Inc., were used in all dissections. The dissections of adult brain were guided by conventional gross anatomical landmarks. Cortex samples included neocortex and dorsal portions of olfactory cortex. Diencephalon samples were taken using the stria medullaris and the optic chiasm as dorsal and ventral landmarks, respectively. Midbrain samples were taken at the level of superior and inferior colliculi, dorsally, and extended to the ventral surface of the brain up to the most rostral edge of the pons. Hindbrain samples lacked cerebella, but included pons and medulla. It should be noted that only rostral portions of the striatum were sampled, to avoid contamination by thalamic tissue. The hippocampal samples were collected from the level of the fimbria/fornix to, approximately, the caudal pole. The dissections of newborn brains utilized similar landmarks, with the exception of the stria medullaris. Timed pregnant rats were used to obtain embryonic tissues, with day of sperm positively designated as day E1; the day of birth was designated PO. Adult rats averaged 150–275 grams (6–8 weeks of age).

12.1.2. RNA Preparation and Northern Blots

Selected tissues were dissected from Sprague-Dawley rats and immediately frozen in liquid nitrogen. RNAs were isolated by homogenization of tissues in 3M LiCl/6M Urea, as described (Bothwell et al., 1990, in Methods of Cloning and Analysis of Eukaryotic Genes, Jones and Bartlett, Boston, Mass.). RNAs (10 μg) were fractionated by electrophoresis through quadruplicate 1% agarose/formaldehyde gels (Bothwell et al., supra) followed by capillary transfer to nylon membranes (MagnaGraph, Micron Separations Inc.) with 10X standard saline citrate (SSC), pH 7. RNAs were UV-crosslinked to the membranes by exposure to ultraviolet light (STRATALINKER®, Stratagene, Inc.) and hybridized at 68° C. with radiolabelled probes in the presence of 0.5 M NaPO4 (pH 7), 1% bovine serum albumen (fraction V, Sigma, Inc.), 7% SDS, 1 mM EDTA (Mahmoudi and Lin, 1989, Biotechniques 7:31–33) and 100 μg/ml sonicated, denatured salmon sperm DNA. Filters were washed at 68° C. with 2xSSC, 0.1% SDS and subjected to autoradiography for one day to two weeks with 1 or 2 intensifying screens (CRONEX®, DuPont) and X-ray film (XAR-5, Kodak) at −70 C. Ethidium bromide staining of the quadruplicate gels demonstrated that equivalent levels of total RNA were being assayed for the different samples (as in Maisonpierre et al., 1990, Science 247:1446–1451); this was confirmed by probing several of the blots using a probe specific for the 28S rRNA.

12.1.3. NT-3, BDNF, NGF AND NGFR Probe Preparation

Molecular cloning of the coding regions for rat NT-3, BDNF and NGF into the pCDM8 expression vector (Aruffo and Seed, 1987, Proc. Natl. Acad. Sci. USA 84:8573–8577) has been described previously (Maisonpierre et al., supra). The 800 basepair (bp) XhoI inserts of these plasmids were separated on acrylamide gels and recovered by electroelution (Bothwell et al., 1990), and subsequently $^{32}$P-labeled by random hexamer labeling (Bothwell et al., supra); hybridization of each of the probes to synthetic NT-3, BDNF and NGF transcripts (see infra) demonstrated that the probe specific for one neurotrophin did not hybridize to transcripts from the related neurotrophins. The rat NGFR probe was a 1.6 kb NcoI cDNA fragment that spans the rat NGFR protein coding region (Radeke et al., 1987, Nature 325:593–597).

12.1.4. Synthetic Transcript Production and Quantitation

The T7 phage promoter present in the pCDM8/neurotrophin expression constructs described above was used to make synthetic RNA transcripts corresponding to the sense orientation of the NT-3, BDNF and NGF coding regions. The amounts of these synthetic transcripts were first quantitated by spectrophotometry. Transcripts were further assayed using an end-labeled (Bothwell et al., supra) 30-mer oligonucleotide probe which hybridized to the common 5' end (just downstream of the T7 promoter) of the three transcripts. Densitometric scanning (Series 300 Computing Densitometer, Molecular Dynamics, Inc.) of dot- and Northern-blotted synthetic transcripts hybridized to the oligonucleotide probe (hybridization and washing performed at 55° C., otherwise as described above) confirmed that equivalent levels of the synthetic transcripts were being used as the defined standards (representative data depicted in FIG. 15A).

12.1.5. Densitometric Quantitation of Neurotrophin Transcript Levels

The transcript levels in various samples were normalized to the standardized adult rat brain sample (see supra) as follows. Equivalent aliquots of the adult brain RNA sample were included on every Northern blot. Densitometric scanning of various autoradiographic exposures for each Northern blot was used to determine signal intensities for every sample assayed. For each exposure scanned, the signal intensities for every sample assayed. For each exposure scanned, the signal intensities for each sample were divided by the value obtained for the signal intensity in the adult brain sample in that exposure, which normalized all values with respect to the standardized adult brain samples. In FIG. 18, the transcript levels in different samples are displayed relative to the levels in the adult brain sample, with the level in adult brain arbitrarily set at 1.0. Having determined the femtograms of neurotrophin transcript per microgram of total RNA in the adult brain sample, we could determine the actual transcript levels (in fg/ug) in samples normalized with respect to the adult brain sample.

12.2. Results

12.2.1. Quantitation and Comparison of NT-3, BDNF and NGF mRNA Levels in Adult Rat Brains We utilized a Northern blot assay system in order to quantitate and compare the expression of NT-3, BDNF and NGF transcripts in a variety of tissue-derived samples. The amount of each neurotrophin transcript in the different samples was quantitated relative to defined synthetic standards. Synthetic NT-3, BDNF and NGF RNA transcripts, whose amounts were precisely determined (see FIG. 15A and its legend), were included on Northern blots also containing 10 ug of total RNA isolated from adult rat brains. The blots were hybridized to radiolabelled probes specific for each neurotrophin, and then subjected to autoradiography (FIG. 15B). Scanning densitometry was then used to compare the hybridization signal intensities obtained from the adult brain sample and the synthetic standards. This quantitation revealed that there were approximately equal mRNA levels (estimated as 40 fg of NT-3 transcripts, 45 fg of BDNF transcripts, and 30 fg of NGF transcripts per ug of total RNA) for all three neurotrophins in the adult rat brain. An aliquot of this standardized adult brain sample was included on all subsequent Northern blots, thus allowing quantitation of neurotrophin expression levels in new RNA samples by comparison (see infra). To aid visual comparison of the three neurotrophin transcripts among different samples, exposures depicted in subsequent figures were chosen so that the signal intensities in the standardized adult brain sample were similar for all three neurotrophins, thereby normalizing the signals in other tissue samples to the defined standard.

12.2.2. NT-3, BDNF AND NGF Gene Expression Displays Common as Well as Unique Developmental Features Examination of neurotrophin gene expression in rat embryos revealed that all three neurotrophins display a dramatic increase in their expression levels between embryonic days eleven and twelve (E11-E12) (FIG. 16A); all three neuroptrophin transcripts are widely distributed throughout E12 and E13 embryos. The timing of the concerted rise in neurotrophin gene expression coincides with the period in which neurogenesis (both peripherally and centrally) begins in earnest, and with the initial elaboration of axons by these newly formed neurons (e.g. Altman and Bayer, 1982, Adv. Anat. Embryol. Cell Biol. Vol. 74; Altman and Bayer, 1984, ibid, Vol. 85).

Despite this coordinated onset of neurotrophin gene expression during embryogenesis, comparison to the standardized adult brain sample reveals that NT-3 mRNA is by far the most abundant in the early embryos (180 fg/ug total RNA), while BDNF mRNA is at least abundant (5–10 fg/ug of total RNA) and NGF mRNA is present at intermediate levels (30 fg/ug of total RNA) (FIG. 16A). NT-3 and BDNF continue to display a reciprocal relationship when expression levels are followed in the developing brain (FIG. 16B) or in the densely innervated heart (FIG. 16C)—initially high NT-3 expression decreases while initially low BDNF expression increases until similar levels are finally attained in the adult; by contrast, NGF expression stays rather constant. Interestingly, NT-3 expression increases during the development of the liver and thymus, organs which are not densely innervated and which do not express detectable BDNF mRNA (FIG. 16C).

Embryonic expression of the NGFR transcript apparently precedes the increase in neurotrophin gene expression, is strikingly high in the early spinal cord, and decreases during the pre-natal development of the brain and the post-natal development of the heart (FIGS. 16A,B,C).

Figures 17A, 17B:
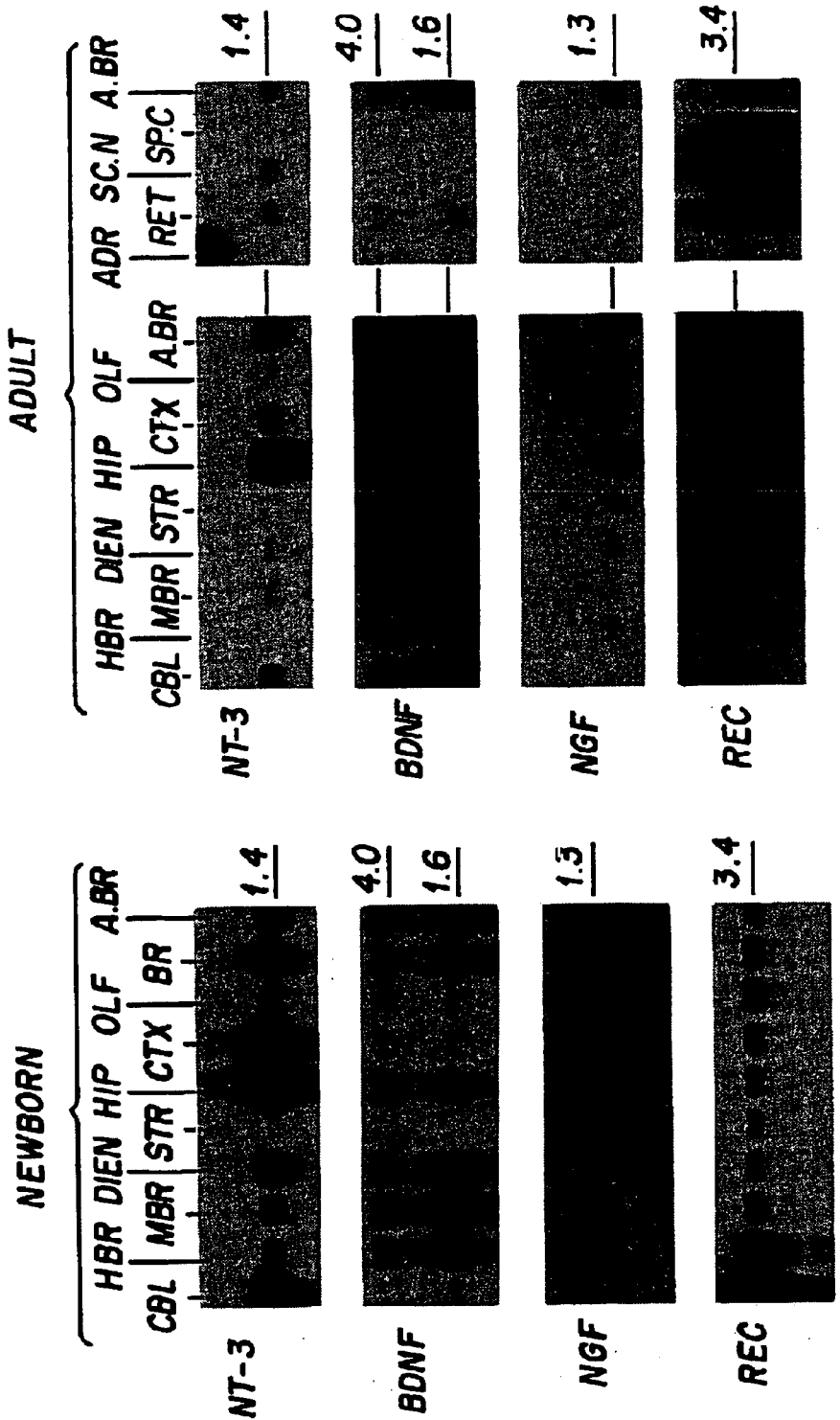
Figure 18A:
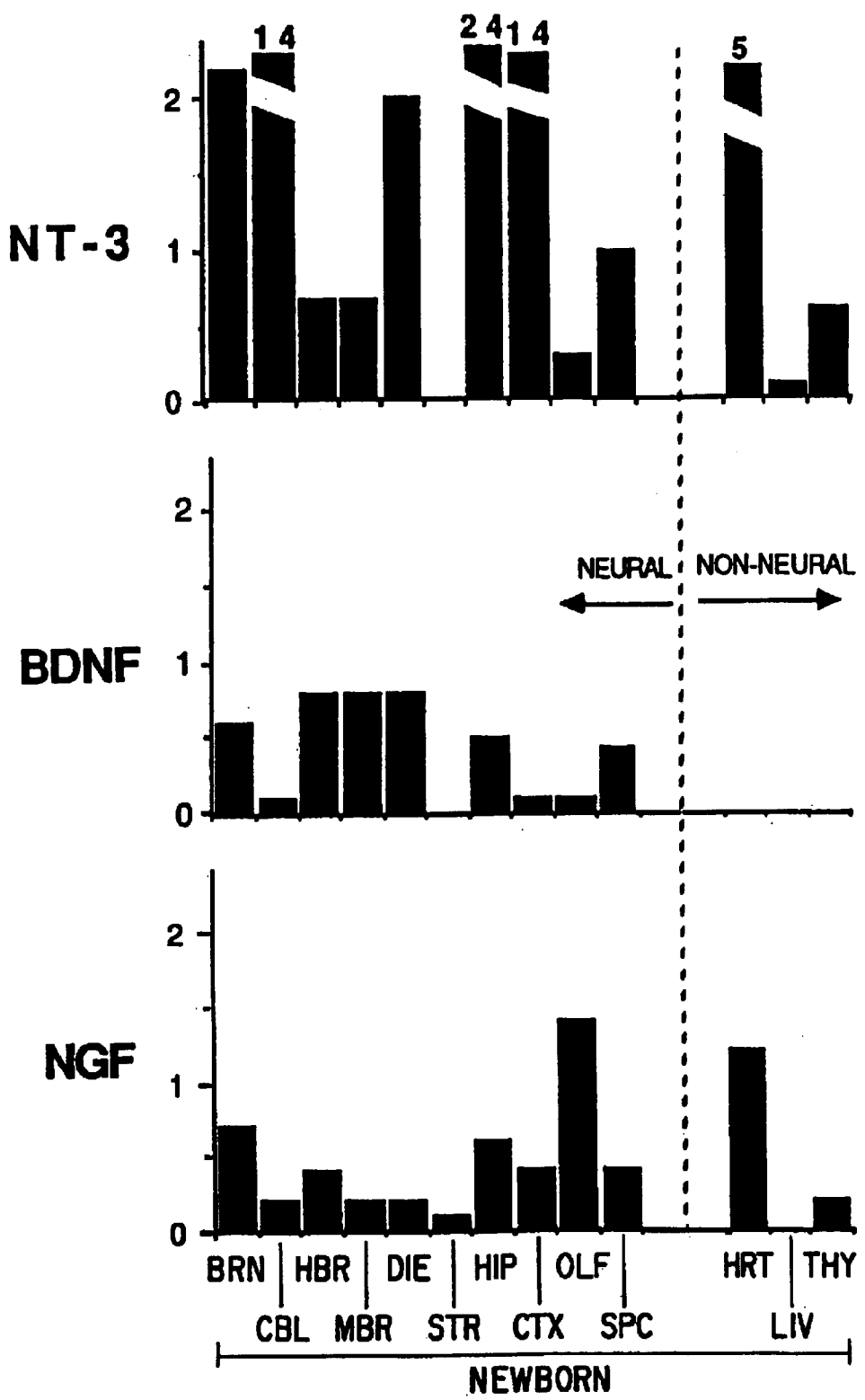
Figure 18B:
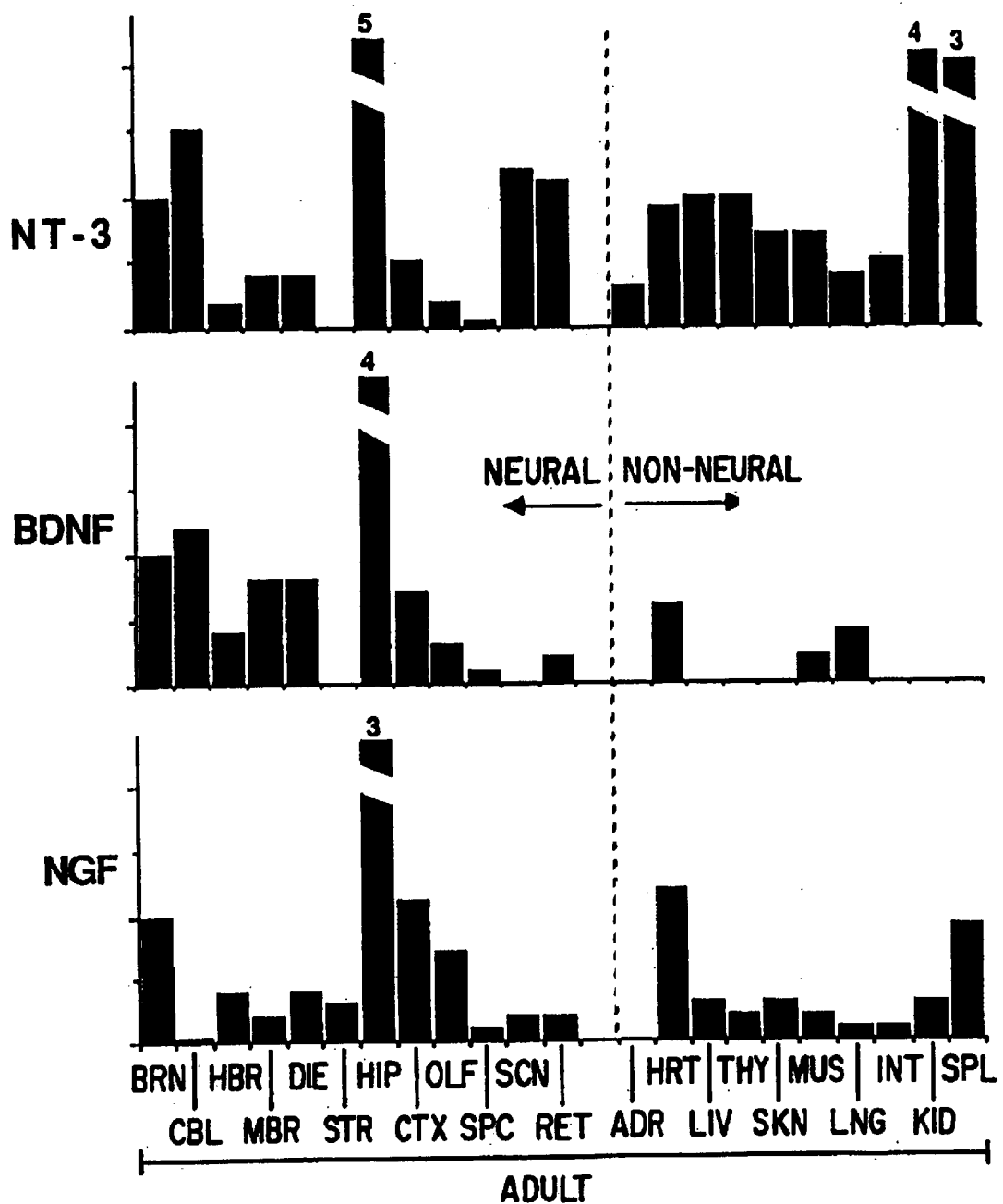

12.2.3. Comparison of NT-3, BDNF, NGF and NGFR Expression within the Newborn and Adult Nervous System To define the spatial distribution of neurotrophin gene expression within the rat nervous system, and to understand how the distinct developmental profiles in whole brains relate to developmental changes within discrete brain regions, we examined neurotrophin gene expression within newborn and adult brains. All three factors displayed discrete spatial and temporal differences in their expression patterns (FIG. 17). Quantitation of transcript levels, including those in peripheral tissues, is displayed in graphic form in FIG. 4. The major similarity shared by all three factors is their uniformly high level of expression in the adult hippocampus. In contrast to the situation in adult peripheral tissues, where NT-3 and NGF expression are more similar in their broad distributions (Maisonpierre et al., supra), NT-3 and BDNF display obvious parallels in their over-all expression patterns within the adult brain (FIGS. 17B, 18B); interestingly, both factors are strikingly absent from the striatum. However, NT-3 and BDNF also display the most interesting, and apparently reciprocal, differences when expression is compared between newborn and adult brains (FIGS. 17A,B and FIGS. 18A,B). NT-3 expression in the newborn is highest, and far higher than in the adult, in more immature regions of the brain (i.e., cerebellum, hippocampus and neocortex). BDNF expression is lowest in these regions and highest, and similar to adult levels, in more caudal brain regions that mature earlier (i.e., hindbrain, midbrain and diencephalon). As in the adult brain, NT-3 and BDNF transcripts are not detectable in the newborn striatum.

Compared to NT-3 and BDNF, NGF mRNA levels display less dramatic differences in the newborn versus adult brain comparison (FIGS. 17, 18); olfactory bulb NGF levels are higher in the newborn, while the hippocampus and neocortex NGF levels are higher in the adult. NGFR mRNA levels were generally higher within the newborn as opposed to the adult brain, with exceptionally high levels in the newborn cerebellum and hindbrain (FIGS. 17A,B).

12.2.4. Examination of NT-3, NGF and BDNF Expression During the Development of Discrete CNS Regions To further pursue the notion that NT-3 is expressed most notably early in the development of particular CNS regions, while BDNF is predominately expressed later in the development of the same regions, we analyzed neurotrophin gene expression during the development of three CNS regions whose maturation follows very different time courses. Neurogenesis, followed rapidly by a period of naturally occuring cel death, begins very early within the spinal cord (E12-E13) and is completed several days before birth (Altman and Bayer, 1984, supra). By contrast, most neurons in the cerebellum and hippocampus (accounted for by their granule cell populations) are born after birth (eg. Altman, 1966, J. Comp. Neur. 128:431–474; Schlessinger et al., 1975, J. Comp. Neurol. 159:149–176). In the later-developing cerebellum, there is extensive neurogenesis, neuroblast migration, and neuronal differentiation during the first three weeks of life (eg. Altman, 1966, supra). It has been reported that NGF mRNA levels in the hippocampus do not become readily detectable until about two weeks after birth (Large et al., 1986, Science 234:352–355); this increase occurs long after the peri-natal onset of extensive granule cell proliferation (eg. Altman, 1966, supra) and the invasion of fibers from the cholinergic neurons of the basal forebrain (Koh and Loy, 1989, J. Neurosci. 9:2999–3018), but coincides with further cholinergic differentiation of these neurons (Large et al., supra).

Our examination of developing spinal cord (FIGS. 5A,E) reveals high levels of NT-3 expression at E12–E13 (150–280 fg/ug total RNA) which decrease by birth and are almost undetectable in the adult. BDNF mRNA, which is barely detectable at E12–E13, peaks at birth (10–20 fg/ug total RNA), and then decreases in the adult. NGF mRNA is expressed at highest levels in E12–E13 spinal cord (15–25 fg/ug total RNA), but at levels 10-fold lower than the NT-3 mRNA levels at the same stage. Interestingly, the NGFR is expressed at highest levels in the early spinal cord; this expression has previously been correlated with the period of naturally occurring cell death of newly formed motor neurons in the early spinal cord (Ernfors et al., 1989, Neuron 2:1605–1613).

In the late-developing cerebellum (FIGS. 19B,F), remarkably high levels of NT-3 mRNA (500–820 fg/ug total RNA) persist throughout the first three weeks after birth, whereas BDNF expression begins to increase only late in this period; very low levels of NGF expression are detectable only in the early stages of cerebellar development. NGFR is expressed at high levels early in cerebellar development and then decreases prior to the observed decrease in NT-3 expression.

In the hippocampus (FIGS. 19C,G), both BDNF and NGF mRNA levels increase from low levels at E17 to intermediate levels at birth, and achieve highest levels in the adult. Although all three neurotrophin transcripts are expressed at similar levels in the adult hippocampus, NT-3 expression is strikingly higher than BDNF and NGF in the E17 and newborn hippocampus, NT-3 expression levels in the newborn hippocampus are as high as those seen in the peri-natal cerebellum (820 fg/ug total RNA). In contrast to the neurotrophins, NGFR expression decreases during the development of the hippocampus.

In all three CNS regions examined above, NT-3 expression is strikingly high during their development and then decreases to adult levels, while initially low BDNF mRNA levels increase to reach adult levels similar to those of NT-3. In contrast to the receiprocal profiles of NT-3 and BDNF, NGF expression does not display any consistent patterns; it is preferentially expressed (although at low levels) early in spinal cord and cerebellar development, but late in hippocampal development.

12.3. Discussion

Our analysis has revealed both similarities and differences in the spatio-temporal distributions of the three neurotrophin transcripts. NT-3, BDNF and NGF transcripts all display a simultaneous increase in their expression between the eleventh and twelfth day of rat embryogenesis, and are widely-distributed in twelve and thirteen day embryos. The timing of this common burst of expression approximately coincides with the developmental onset of neurogenesis (eq. Altman and Bayer, 1982, supra; Altman and Bayer, 1984, supra). This association supports the notion that the three neurotrophins play developmental roles of particular importance to the nervous system, and may mark the period when all of the neurotrophins first become generally required to maintain the survival of post-mitotic neurons. However, the timing of their expression could also be indicative of other roles for the neurotrophins in the developing nervous system (see below).

Although the onset of gene expression occurs simultaneously for the three neurotophins, the levels they achieve in early embryos differ greatly. NT-3 mRNA is by far the most abundant in embryos, while BDNF mRNA is expressed at the lowest levels. This contrast between NT-3 and BDNF expression continues in almost every instance examined. During development, NT-3 expression is most prominent in CNS regions in which proliferation, migration and differentiation of neurons and their precursors is ongoing, and generally decreases dramatically within CNS regions as they mature. By contrast BDNF expression in the newborn is most prominent in CNS regions in which neurogenesis has already occurred, and generally increases within CNS regions as they mature. Interestingly, the levels that the NT-3 and BDNF transcripts ultimately achieve in various adult CNS regions are quite similar. The reciprocal relationship between NT-3 and BDNF expression during development, coupled with their relatively similar profiles in the adult CNS, indicate that NT-3 and BDNF may in some cases act on the same neuronal populations in the CNS. If so, our data would suggest that NT-3 plays an important role in the development of these neurons (perhaps during the establishment of target innervation), while BDNF might predominately act later in the life of the same nurons (i.e., as a maturation or maintenance factor). NGF expression varies locally during development, but these variations do not follow a consistent pattern as do those of NT-3 and BDNF. NGFR mRNA levels do not specifically mirror the expression of any one of the three neurotrophin genes, consistent with the possibility that it might serve as a common component of the individual neurotrophin receptors (Rodriguez-Tebar et al., 1990, Neuron 4:487–492). NGFR expression does tend to be highest early in the development of CNS regions, and our studies reveal interesting developmentally regulated changes in NGFR expression which are the subject of further investigations.

In contrast to their similar distributions within the adult CNS, NT-3 and BDNF have dramatically different patterns of expression within adult peripheral tissues; the broader peripheral distribution of NT-3 transcripts may reflect activity on a wider (and different) range of (neural as well as non-neural) cells in the periphery than BDNF (Maisonpierre et al., supra).

Although there is considerable evidence suggesting that both NGF and BDNF play an important early role in the development of the nervous system, our analysis reveals a much more consistent and impressive correlation between remarkably high NT-3 expression and early neural development. NT-3 mRNA levels in the developing cerebellum and newborn hippocampus are several fold higher than the levels of any of the neurotrophins in any other tissue or brain region, and more than twenty-fold higher than the levels of any of the neurotrophins in the adult brain. The discovery of NT-3 as a novel NGF-related protein which can support at least some BDNF- and NGF-dependent neurons (Maisonpierre et al., supra), and whose temporal expression most clearly parallels critical periods of neural development, raises the possiblility that NT-3 is the physiological agent normally responsible for some of the developmentally important functions previously attributed to BDNF or NGF. A re-exploration of the true developmental roles of all the members of this family is further emphasized because of the possibility that antibodies to these related factors may cross-react (Whittemore and Seiger, 1987, Brain Res. Rev. 12:439–464).

Although we have previously demonstrated that NT-3 can act as a classical neuronal survival molecule (Maisonpierre et al., supra), allowing for the action of NT-3 as a target-derived factor whose limited expression results in neuronal selection and pruning, this by no means excludes other developmentally important roles for NT-3 (as well as for the other neurotrophins). The pattern of NT-3 expression within the developing nervous system shares remarkable similarities with that of nestin (a novel intermediate filament protein whose expression is characteristic of CNS regions undergoing neurogenesis—Lendahl et al., 1990) and SNAP (an antigenic marker of early neurite outgrowth—Yamamoto et al., 1986, J. Neurosci. 6:3576–3594). Unlike the case with NGF (Clegg et al., 1989, Devel. Biol. 134:30–37), high levels of NT-3 expression precede the arrival of sympathetic fibers to the heart. Thus, NT-3 might be particularly linked to developmental processes other than neuronal survival, including neuronal precursor proliferation/differentiation and/or the guidance of migrating cells or their axons; further suggestion of such potential physiological roles for NT-3 comes from recent findings that one of the neurotrophins (i.e., NGF) can play a role in neuronal precursor proliferation in vitro. Conversely BDNF, although present early in development, may have a more generally important role long after the initial period of neuronal death and selection.

The expression profiles of all three neurotrophins in the adult do share a striking similarity—all three neurotrophins are expressed at comparably high levels in the adult hippocampus. Disrupting the projections of basal forebrain cholinergic neurons to the hippocampus results in atrophy and decreased transmitter synthesis by these neurons (reviewed in Snider and Johnson, 1989, Ann. Neurol. 26:489–506). A similar atrophy is associated with poor performance in memory-specific tasks in aged rats and in humans with Alzheimer's disease. Atrophy of basal forebrain cholinergic neurons can be reversed in rat models by the administration of NGF. The data presented here is consistent with the possibility that the adult hippocampus may normally supply all three neurotrophins to the basal forebrain, suggesting that recent evidence for the complementary actions of NGF and BDNF on cultured cholinergic neurons reflects the true physiological roles for these molecules. However, NT-3 expression is remarkably high very early in hippocampal development, and then decreases to adult levels which are similar to those of NGF and BDNF. This high early expression agains suggests that NT-3 may be playing a unique role in the guidance or establishment of early connections from the basal forebrain or other hippocampal afferents, or in the proliferation of dentate granule cell precursors; relatively low levels of NGF during early hippocampal development have argued against such a role for NGF (Large et al., supra).

13. Deposit of Microorganisms

The following were deposited on Feb. 28, 1990 with the American Type Culture Collection, 12301 Parklawn Drive, Rockville, Md. 20852:

| | strain | ATCC Accession Number |
|---|---|---|
| bacteriophage DNA | φhN3 (G1) | 40763 |
| bacteriophage DNA | φrN3 (G1) | 40764 |
| plasmid | pC8-rN3 (P1) | 40766 |
| plasmid | pC8-hN3 (P1) | 40765 |

The present invention is not to be limited in scope by the specific embodi